US012562243B2

(12) United States Patent
Guaneri et al.

(10) Patent No.: US 12,562,243 B2
(45) Date of Patent: Feb. 24, 2026

(54) SYSTEM AND METHOD FOR PROCESSING MEDICAL CLAIMS USING BIOMETRIC SIGNATURES

(71) Applicant: ROM TECHNOLOGIES, INC., Brookfield, CT (US)

(72) Inventors: Joseph Guaneri, Brookfield, CT (US); Daniel Posnack, Brookfield, CT (US); Peter Arn, Brookfield, CT (US); Wendy Para, Brookfield, CT (US); S. Adam Hacking, Brookfield, CT (US); Micheal Mueller, Brookfield, CT (US); Jonathan Greene, Brookfield, CT (US); Steven Mason, Brookfield, CT (US)

(73) Assignee: ROM Technologies, Inc., Brookfield, CT (US)

( * ) Notice: Subject to any disclaimer, the term of this patent is extended or adjusted under 35 U.S.C. 154(b) by 966 days.

(21) Appl. No.: 17/147,593

(22) Filed: Jan. 13, 2021

(65) Prior Publication Data

US 2021/0134412 A1     May 6, 2021

Related U.S. Application Data

(63) Continuation-in-part of application No. 17/021,895, filed on Sep. 15, 2020, now Pat. No. 11,071,597.

(Continued)

(51) Int. Cl.
G16H 10/60          (2018.01)
G06F 21/64          (2013.01)
(Continued)

(52) U.S. Cl.
CPC ............. G16H 10/60 (2018.01); G06F 21/64 (2013.01); G16H 20/00 (2018.01); G16H 40/67 (2018.01)

(58) Field of Classification Search
None
See application file for complete search history.

(56)          References Cited

U.S. PATENT DOCUMENTS 4,822,032  A      4/1989  Whitmore et al.
4,860,763  A      8/1989  Schminke
              (Continued)

FOREIGN PATENT DOCUMENTS

CA          2698078  A1      3/2010
CA          3193419  A1      3/2022
              (Continued)

OTHER PUBLICATIONS

Joudaki et al., "Using Data Mining to Detect Health Care Fraud and Abuse: A Review of Literature", Global Journal of Health Science, vol. 7, No. 1, 2015 (Year: 2015).*

(Continued)

*Primary Examiner* — Anne-Marie K Alderson
(74) *Attorney, Agent, or Firm* — Dickinson Wright PLLC; Jonathan H. Harder; Stephen A. Mason

(57)          ABSTRACT

A computer-implemented system for processing medical claims is disclosed. The computer-implemented system includes a medical device configured to be manipulated by a user while the user performs a treatment plan; a patient interface associated with the medical device, the patient interface comprising an output configured to present tele-medicine information associated with a telemedicine session; and a processor. The processor is configured to, during the telemedicine session, receive device-generated information from the medical device; generate a first biometric signature; using the device-generated information, generate a second biometric signature; using the first and second biometric signatures, generate a signature comparison; using (Continued)

the signature comparison, generate a signature indicator; and transmit the signature indicator.

17 Claims, 11 Drawing Sheets

Related U.S. Application Data

(60) Provisional application No. 63/028,420, filed on May 21, 2020, provisional application No. 62/910,232, filed on Oct. 3, 2019.

(51) Int. Cl.
  *G16H 20/00* (2018.01)
  *G16H 40/67* (2018.01)

(56) References Cited

U.S. PATENT DOCUMENTS

| | | | |
|---|---|---|---|
| 4,932,650 | A | 6/1990 | Bingham et al. |
| 5,137,501 | A | 8/1992 | Mertesdorf |
| 5,240,417 | A | 8/1993 | Smithson et al. |
| 5,256,117 | A | 10/1993 | Potts et al. |
| 5,284,131 | A | 2/1994 | Gray |
| 5,318,487 | A | 6/1994 | Golen |
| 5,356,356 | A | 10/1994 | Hildebrandt |
| D359,777 | S | 6/1995 | Hildebrandt |
| 5,429,140 | A | 7/1995 | Burdea et al. |
| 5,738,636 | A | 4/1998 | Saringer et al. |
| 6,007,459 | A | 12/1999 | Burgess |
| D421,075 | S | 2/2000 | Hildebrandt |
| 6,110,130 | A | 8/2000 | Kramer |
| 6,162,189 | A | 12/2000 | Girone et al. |
| 6,182,029 | B1 | 1/2001 | Friedman |
| 6,267,735 | B1 | 7/2001 | Blanchard et al. |
| 6,273,863 | B1 | 8/2001 | Avni et al. |
| 6,413,190 | B1 | 7/2002 | Wood et al. |
| 6,436,058 | B1 | 8/2002 | Krahner et al. |
| 6,450,923 | B1 | 9/2002 | Vatti |
| 6,491,649 | B1 | 12/2002 | Ombrellaro |
| 6,514,085 | B2 | 2/2003 | Slattery et al. |
| 6,535,861 | B1 | 3/2003 | OConnor et al. |
| 6,601,016 | B1 | 7/2003 | Brown et al. |
| 6,602,191 | B2 | 8/2003 | Quy |
| 6,613,000 | B1 | 9/2003 | Reinkensmeyer et al. |
| 6,626,800 | B1 | 9/2003 | Casler |
| 6,626,805 | B1 | 9/2003 | Lightbody |
| 6,640,122 | B2 | 10/2003 | Manoli |
| 6,652,425 | B1 | 11/2003 | Martin et al. |
| 6,890,312 | B1 | 5/2005 | Priester et al. |
| 6,902,513 | B1 | 6/2005 | McClure |
| 7,058,453 | B2 | 6/2006 | Nelson et al. |
| 7,063,643 | B2 | 6/2006 | Arai |
| 7,156,665 | B1 | 1/2007 | OConnor et al. |
| 7,156,780 | B1 | 1/2007 | Fuchs et al. |
| 7,169,085 | B1 | 1/2007 | Killin et al. |
| 7,209,886 | B2* | 4/2007 | Kimmel ................. G06Q 30/06 |
| | | | 705/3 |
| 7,226,394 | B2 | 6/2007 | Johnson |
| RE39,904 | E | 10/2007 | Lee |
| 7,507,188 | B2 | 3/2009 | Nurre |
| 7,594,879 | B2 | 9/2009 | Johnson |
| 7,628,730 | B1 | 12/2009 | Watterson et al. |
| D610,635 | S | 2/2010 | Hildebrandt |
| 7,778,851 | B2 | 8/2010 | Schoenberg et al. |
| 7,809,601 | B2 | 10/2010 | Shaya et al. |
| 7,815,551 | B2 | 10/2010 | Merli |
| 7,833,135 | B2 | 11/2010 | Radow et al. |
| 7,837,472 | B1 | 11/2010 | Elsmore et al. |
| 7,890,342 | B1 | 2/2011 | Yruko |
| 7,955,219 | B2 | 6/2011 | Birrell et al. |
| 7,969,315 | B1 | 6/2011 | Ross et al. |
| 7,974,689 | B2 | 7/2011 | Volpe et al. |
| 7,988,599 | B2 | 8/2011 | Ainsworth et al. |

| | | | |
|---|---|---|---|
| 8,012,107 | B2 | 9/2011 | Einav et al. |
| 8,021,270 | B2 | 9/2011 | D'Eredita |
| 8,038,578 | B2 | 10/2011 | Olrik et al. |
| 8,079,937 | B2 | 12/2011 | Bedell et al. |
| 8,113,991 | B2 | 2/2012 | Kutliroff |
| 8,172,724 | B2 | 5/2012 | Solomon |
| 8,177,732 | B2 | 5/2012 | Einav et al. |
| 8,287,434 | B2 | 10/2012 | Zavadsky et al. |
| 8,298,123 | B2 | 10/2012 | Hickman |
| 8,371,990 | B2 | 2/2013 | Shea |
| 8,419,593 | B2 | 4/2013 | Ainsworth et al. |
| 8,465,398 | B2 | 6/2013 | Lee et al. |
| 8,503,086 | B2* | 8/2013 | French ............... A63B 24/0062 |
| | | | 73/379.04 |
| 8,506,458 | B2 | 8/2013 | Dugan |
| 8,515,777 | B1 | 8/2013 | Rajasenan |
| 8,540,515 | B2 | 9/2013 | Williams et al. |
| 8,540,516 | B2 | 9/2013 | Williams et al. |
| 8,556,778 | B1 | 10/2013 | Dugan |
| 8,607,465 | B1 | 12/2013 | Edwards |
| 8,613,689 | B2 | 12/2013 | Dyer et al. |
| 8,615,529 | B2 | 12/2013 | Reiner |
| 8,672,812 | B2 | 3/2014 | Dugan |
| 8,751,264 | B2 | 6/2014 | Beraja et al. |
| 8,784,273 | B2 | 7/2014 | Dugan |
| 8,818,496 | B2 | 8/2014 | Dziubinski et al. |
| 8,823,448 | B1 | 9/2014 | Shen |
| 8,845,493 | B2 | 9/2014 | Watterson et al. |
| 8,849,681 | B2 | 9/2014 | Hargrove et al. |
| 8,864,628 | B2 | 10/2014 | Boyette et al. |
| 8,893,287 | B2 | 11/2014 | Gjonej et al. |
| 8,911,327 | B1 | 12/2014 | Boyette |
| 8,979,711 | B2 | 3/2015 | Dugan |
| 9,004,598 | B2 | 4/2015 | Weber |
| 9,167,281 | B2 | 10/2015 | Petrov et al. |
| 9,248,071 | B1 | 2/2016 | Benda et al. |
| 9,256,711 | B2 | 2/2016 | Horseman |
| 9,272,091 | B2 | 3/2016 | Skelton |
| 9,272,185 | B2 | 3/2016 | Dugan |
| 9,283,434 | B1 | 3/2016 | Wu |
| 9,295,878 | B2 | 3/2016 | Corbalis et al. |
| 9,311,789 | B1 | 4/2016 | Gwin |
| 9,367,668 | B2 | 6/2016 | Flynt et al. |
| 9,409,054 | B2 | 8/2016 | Dugan |
| 9,443,205 | B2 | 9/2016 | Wall |
| 9,474,935 | B2 | 10/2016 | Abbondanza et al. |
| 9,481,428 | B2 | 11/2016 | Gros et al. |
| 9,514,277 | B2 | 12/2016 | Hassing et al. |
| 9,566,472 | B2 | 2/2017 | Dugan |
| 9,579,056 | B2 | 2/2017 | Rosenbek et al. |
| 9,629,558 | B2 | 4/2017 | Yuen et al. |
| 9,640,057 | B1 | 5/2017 | Ross |
| 9,707,147 | B2 | 7/2017 | Levital et al. |
| D794,142 | S | 8/2017 | Zhou |
| 9,717,947 | B2 | 8/2017 | Lin |
| 9,737,761 | B1 | 8/2017 | Govindarajan |
| 9,757,612 | B2 | 9/2017 | Weber |
| 9,773,330 | B1* | 9/2017 | Douglas ................. G06F 3/011 |
| 9,782,621 | B2 | 10/2017 | Chiang et al. |
| 9,802,076 | B2 | 10/2017 | Murray et al. |
| 9,802,081 | B2 | 10/2017 | Ridgel et al. |
| 9,813,239 | B2 | 11/2017 | Chee et al. |
| 9,827,445 | B2 | 11/2017 | Marcos et al. |
| 9,849,337 | B2 | 12/2017 | Roman et al. |
| 9,868,028 | B2 | 1/2018 | Shin |
| 9,872,087 | B2 | 1/2018 | DelloStritto et al. |
| 9,872,637 | B2 | 1/2018 | Kording et al. |
| 9,914,053 | B2 | 3/2018 | Dugan |
| 9,937,382 | B2 | 4/2018 | Dugan |
| 9,939,784 | B1 | 4/2018 | Berardinelli |
| 9,974,478 | B1 | 5/2018 | Brokaw |
| 9,977,587 | B2 | 5/2018 | Mountain |
| 9,993,181 | B2 | 6/2018 | Ross |
| 9,997,082 | B2 | 6/2018 | Kaleal |
| 10,004,946 | B2 | 6/2018 | Ross |
| 10,026,052 | B2 | 7/2018 | Brown et al. |
| D826,349 | S | 8/2018 | Oblamski |
| 10,055,550 | B2 | 8/2018 | Goetz |
| 10,058,473 | B2 | 8/2018 | Oshima et al. |

(56) References Cited

U.S. PATENT DOCUMENTS

| | | | |
|---|---|---|---|
| 10,074,148 | B2 | 9/2018 | Cashman et al. |
| 10,089,443 | B2 | 10/2018 | Miller et al. |
| 10,111,643 | B2 | 10/2018 | Shulhauser et al. |
| 10,130,298 | B2 | 11/2018 | Mokaya et al. |
| 10,130,311 | B1 | 11/2018 | De Sapio et al. |
| 10,137,328 | B2 | 11/2018 | Baudhuin |
| 10,143,395 | B2 | 12/2018 | Chakravarthy et al. |
| 10,155,134 | B2 | 12/2018 | Dugan |
| 10,159,872 | B2 | 12/2018 | Sasaki et al. |
| 10,173,094 | B2 | 1/2019 | Gomberg et al. |
| 10,173,095 | B2 | 1/2019 | Gomberg et al. |
| 10,173,096 | B2 | 1/2019 | Gomberg et al. |
| 10,173,097 | B2 | 1/2019 | Gomberg et al. |
| 10,198,928 | B1 | 2/2019 | Ross et al. |
| 10,226,663 | B2 | 3/2019 | Gomberg et al. |
| 10,231,664 | B2 | 3/2019 | Ganesh |
| 10,244,990 | B2 | 4/2019 | Hu et al. |
| 10,258,823 | B2 | 4/2019 | Cole |
| 10,322,315 | B2 | 6/2019 | Foley et al. |
| 10,325,070 | B2 | 6/2019 | Beale et al. |
| 10,327,697 | B1 | 6/2019 | Stein et al. |
| 10,362,940 | B2 | 7/2019 | Tran |
| 10,369,021 | B2 | 8/2019 | Zoss et al. |
| 10,380,866 | B1 | 8/2019 | Ross et al. |
| 10,413,222 | B1 * | 9/2019 | Kayyali .............. A61B 5/4809 |
| 10,413,238 | B1 | 9/2019 | Cooper |
| 10,424,033 | B2 | 9/2019 | Romeo |
| 10,430,552 | B2 | 10/2019 | Mihai |
| D866,957 | S | 11/2019 | Ross et al. |
| 10,468,131 | B2 | 11/2019 | Macoviak et al. |
| 10,475,323 | B1 | 11/2019 | Ross |
| 10,475,537 | B2 | 11/2019 | Purdie et al. |
| 10,492,977 | B2 | 12/2019 | Kapure et al. |
| 10,507,358 | B2 | 12/2019 | Kinnunen et al. |
| 10,542,914 | B2 | 1/2020 | Forth et al. |
| 10,546,467 | B1 | 1/2020 | Luciano, Jr. et al. |
| 10,569,122 | B2 | 2/2020 | Johnson |
| 10,572,626 | B2 | 2/2020 | Balram |
| 10,576,331 | B2 | 3/2020 | Kuo |
| 10,581,896 | B2 | 3/2020 | Nachenberg |
| 10,625,114 | B2 | 4/2020 | Ercanbrack |
| 10,646,746 | B1 | 5/2020 | Gomberg et al. |
| 10,660,534 | B2 | 5/2020 | Lee et al. |
| 10,678,890 | B2 | 6/2020 | Bitran et al. |
| 10,685,092 | B2 | 6/2020 | Paparella et al. |
| 10,741,285 | B2 | 8/2020 | Moturu |
| 10,777,200 | B2 | 9/2020 | Will et al. |
| D899,605 | S | 10/2020 | Ross et al. |
| 10,792,495 | B2 | 10/2020 | Izvorski et al. |
| 10,814,170 | B2 | 10/2020 | Wang et al. |
| 10,857,426 | B1 | 12/2020 | Neumann |
| 10,867,695 | B2 | 12/2020 | Neagle |
| 10,874,905 | B2 | 12/2020 | Belson et al. |
| D907,143 | S | 1/2021 | Ach et al. |
| 10,881,911 | B2 | 1/2021 | Kwon et al. |
| 10,918,332 | B2 | 2/2021 | Belson et al. |
| 10,931,643 | B1 | 2/2021 | Neumann |
| 10,987,176 | B2 | 4/2021 | Poltaretskyi et al. |
| 10,991,463 | B2 | 4/2021 | Kutzko et al. |
| 11,000,735 | B2 | 5/2021 | Orady et al. |
| 11,045,709 | B2 | 6/2021 | Putnam |
| 11,065,170 | B2 | 7/2021 | Yang et al. |
| 11,065,527 | B2 | 7/2021 | Putnam |
| 11,069,436 | B2 | 7/2021 | Mason et al. |
| 11,071,597 | B2 | 7/2021 | Posnack et al. |
| 11,075,000 | B2 | 7/2021 | Mason et al. |
| D928,635 | S | 8/2021 | Hacking et al. |
| 11,087,865 | B2 | 8/2021 | Mason et al. |
| 11,094,400 | B2 | 8/2021 | Riley et al. |
| 11,101,028 | B2 | 8/2021 | Mason et al. |
| 11,107,591 | B1 | 8/2021 | Mason |
| 11,139,060 | B2 | 10/2021 | Mason et al. |
| 11,185,735 | B2 | 11/2021 | Arn et al. |
| 11,185,738 | B1 * | 11/2021 | McKirdy ........... A63B 24/0075 |
| D939,096 | S | 12/2021 | Lee |
| D939,644 | S | 12/2021 | Ach et al. |
| D940,797 | S | 1/2022 | Ach et al. |
| D940,891 | S | 1/2022 | Lee |
| 11,229,727 | B2 | 1/2022 | Tatonetti |
| 11,229,788 | B1 | 1/2022 | John |
| 11,265,234 | B2 | 3/2022 | Guaneri et al. |
| 11,270,795 | B2 | 3/2022 | Mason et al. |
| 11,272,879 | B2 | 3/2022 | Wiedenhoefer et al. |
| 11,278,766 | B2 | 3/2022 | Lee |
| 11,282,599 | B2 | 3/2022 | Mason et al. |
| 11,282,604 | B2 | 3/2022 | Mason et al. |
| 11,282,608 | B2 | 3/2022 | Mason et al. |
| 11,284,797 | B2 | 3/2022 | Mason et al. |
| D948,639 | S | 4/2022 | Ach et al. |
| 11,295,848 | B2 | 4/2022 | Mason et al. |
| 11,298,284 | B2 | 4/2022 | Bayerlein |
| 11,309,085 | B2 | 4/2022 | Mason et al. |
| 11,317,975 | B2 | 5/2022 | Mason et al. |
| 11,325,005 | B2 | 5/2022 | Mason et al. |
| 11,328,807 | B2 | 5/2022 | Mason et al. |
| 11,337,648 | B2 | 5/2022 | Mason |
| 11,347,829 | B1 | 5/2022 | Sclar et al. |
| 11,348,683 | B2 | 5/2022 | Guaneri et al. |
| 11,370,328 | B2 | 6/2022 | Main |
| 11,376,470 | B2 | 7/2022 | Weldemariam |
| 11,404,150 | B2 | 8/2022 | Guaneri et al. |
| 11,410,768 | B2 | 8/2022 | Mason et al. |
| 11,422,841 | B2 | 8/2022 | Jeong |
| 11,437,137 | B1 | 9/2022 | Harris |
| 11,495,355 | B2 | 11/2022 | McNutt et al. |
| 11,508,258 | B2 | 11/2022 | Nakashima et al. |
| 11,508,482 | B2 | 11/2022 | Mason et al. |
| 11,515,021 | B2 | 11/2022 | Mason |
| 11,515,028 | B2 | 11/2022 | Mason |
| 11,524,210 | B2 | 12/2022 | Kim et al. |
| 11,527,326 | B2 | 12/2022 | McNair et al. |
| 11,532,402 | B2 | 12/2022 | Farley et al. |
| 11,534,654 | B2 | 12/2022 | Silcock et al. |
| D976,339 | S | 1/2023 | Li |
| 11,541,274 | B2 | 1/2023 | Hacking |
| 11,553,969 | B1 | 1/2023 | Lang et al. |
| 11,621,067 | B1 | 4/2023 | Nolan |
| 11,636,944 | B2 | 4/2023 | Hanrahan et al. |
| 11,654,327 | B2 | 5/2023 | Phillips et al. |
| 11,663,673 | B2 | 5/2023 | Pyles |
| 11,673,024 | B2 | 6/2023 | Omid-Zohoor |
| 11,701,548 | B2 | 7/2023 | Posnack et al. |
| 11,776,676 | B2 | 10/2023 | Savolainen |
| 11,944,579 | B2 | 4/2024 | Sankai |
| 11,957,960 | B2 | 4/2024 | Bissonnette et al. |
| 12,004,871 | B1 | 6/2024 | Fazeli |
| 12,057,210 | B2 | 8/2024 | Akinola et al. |
| 12,205,704 | B2 | 1/2025 | Hosoi et al. |
| 2001/0044573 | A1 | 11/2001 | Manoli |
| 2002/0010596 | A1 | 1/2002 | Matory |
| 2002/0072452 | A1 | 6/2002 | Torkelson |
| 2002/0143279 | A1 | 10/2002 | Porter et al. |
| 2002/0160883 | A1 | 10/2002 | Dugan |
| 2002/0183599 | A1 | 12/2002 | Castellanos |
| 2003/0013072 | A1 | 1/2003 | Thomas |
| 2003/0036683 | A1 | 2/2003 | Kehr et al. |
| 2003/0064860 | A1 | 4/2003 | Yamashita et al. |
| 2003/0064863 | A1 | 4/2003 | Chen |
| 2003/0083596 | A1 | 5/2003 | Kramer et al. |
| 2003/0181832 | A1 | 9/2003 | Carnahan et al. |
| 2004/0072652 | A1 | 4/2004 | Alessandri et al. |
| 2004/0102931 | A1 | 5/2004 | Ellis et al. |
| 2004/0147969 | A1 | 7/2004 | Mann et al. |
| 2004/0197727 | A1 | 10/2004 | Sachdeva et al. |
| 2004/0204959 | A1 | 10/2004 | Moreano et al. |
| 2005/0043153 | A1 | 2/2005 | Krietzman |
| 2005/0049122 | A1 | 3/2005 | Vallone et al. |
| 2005/0115561 | A1 | 6/2005 | Stahmann |
| 2005/0143641 | A1 | 6/2005 | Tashiro |
| 2006/0046905 | A1 | 3/2006 | Doody, Jr. et al. |
| 2006/0058648 | A1 | 3/2006 | Meier |
| 2006/0064136 | A1 | 3/2006 | Wang |
| 2006/0064329 | A1 | 3/2006 | Abolfathi et al. |
| 2006/0129432 | A1 | 6/2006 | Choi et al. |

(56) References Cited

U.S. PATENT DOCUMENTS

| | | |
|---|---|---|
| 2006/0199700 A1 | 9/2006 | LaStayo et al. |
| 2006/0277074 A1 | 12/2006 | Einav |
| 2007/0042868 A1 | 2/2007 | Fisher et al. |
| 2007/0118389 A1 | 5/2007 | Shipon |
| 2007/0118406 A1 | 5/2007 | Killin et al. |
| 2007/0137307 A1 | 6/2007 | Gruben et al. |
| 2007/0173392 A1 | 7/2007 | Stanford |
| 2007/0184414 A1 | 8/2007 | Perez |
| 2007/0194939 A1 | 8/2007 | Alvarez et al. |
| 2007/0219059 A1 | 9/2007 | Schwartz |
| 2007/0271065 A1 | 11/2007 | Gupta et al. |
| 2007/0287597 A1 | 12/2007 | Cameron |
| 2008/0021834 A1 | 1/2008 | Holla et al. |
| 2008/0077619 A1 | 3/2008 | Gilley et al. |
| 2008/0082356 A1 | 4/2008 | Friedlander et al. |
| 2008/0096726 A1 | 4/2008 | Riley et al. |
| 2008/0153592 A1 | 6/2008 | James-Herbert |
| 2008/0161733 A1 | 7/2008 | Einav et al. |
| 2008/0183500 A1 | 7/2008 | Banigan |
| 2008/0281633 A1 | 11/2008 | Burdea et al. |
| 2008/0300914 A1 | 12/2008 | Karkanias et al. |
| 2008/0312040 A1 | 12/2008 | Ochi |
| 2009/0011907 A1 | 1/2009 | Radow et al. |
| 2009/0037334 A1 | 2/2009 | Hsu |
| 2009/0058635 A1 | 3/2009 | LaLonde et al. |
| 2009/0070138 A1 | 3/2009 | Langheier et al. |
| 2009/0157617 A1 | 6/2009 | Herlocker |
| 2009/0270227 A1 | 10/2009 | Ashby et al. |
| 2009/0287503 A1 | 11/2009 | Angell et al. |
| 2009/0299766 A1 | 12/2009 | Friedlander et al. |
| 2010/0048358 A1 | 2/2010 | Tchao et al. |
| 2010/0062818 A1 | 3/2010 | Haughay, Jr. |
| 2010/0076786 A1 | 3/2010 | Dalton et al. |
| 2010/0121160 A1 | 5/2010 | Stark et al. |
| 2010/0173747 A1 | 7/2010 | Chen et al. |
| 2010/0216168 A1 | 8/2010 | Heinzman et al. |
| 2010/0234184 A1 | 9/2010 | Le Page et al. |
| 2010/0248899 A1 | 9/2010 | Bedell et al. |
| 2010/0262052 A1 | 10/2010 | Lunau et al. |
| 2010/0268304 A1 | 10/2010 | Matos |
| 2010/0293003 A1 | 11/2010 | Abbo |
| 2010/0298102 A1 | 11/2010 | Bosecker et al. |
| 2010/0326207 A1 | 12/2010 | Topel |
| 2010/0332583 A1 | 12/2010 | Szabo |
| 2011/0010188 A1 | 1/2011 | Yoshikawa et al. |
| 2011/0047108 A1 | 2/2011 | Chakrabarty et al. |
| 2011/0082007 A1 | 4/2011 | Birrell |
| 2011/0087137 A1 | 4/2011 | Hanoun |
| 2011/0119212 A1 | 5/2011 | De Bruin et al. |
| 2011/0172059 A1 | 7/2011 | Watterson et al. |
| 2011/0195819 A1 | 8/2011 | Shaw et al. |
| 2011/0218462 A1* | 9/2011 | Smith .................. A61B 5/6831 |
| | | 600/595 |
| 2011/0218814 A1 | 9/2011 | Coats |
| 2011/0275483 A1 | 11/2011 | Dugan |
| 2011/0281249 A1 | 11/2011 | Gammell et al. |
| 2011/0306846 A1 | 12/2011 | Osorio |
| 2012/0041771 A1 | 2/2012 | Cosentino et al. |
| 2012/0065987 A1 | 3/2012 | Farooq et al. |
| 2012/0116258 A1 | 5/2012 | Lee |
| 2012/0130196 A1 | 5/2012 | Jain et al. |
| 2012/0130197 A1* | 5/2012 | Kugler .................. A61B 5/742 |
| | | 600/300 |
| 2012/0183939 A1 | 7/2012 | Aragones et al. |
| 2012/0190502 A1 | 7/2012 | Paulus et al. |
| 2012/0232438 A1 | 9/2012 | Cataldi et al. |
| 2012/0259648 A1 | 10/2012 | Mallon et al. |
| 2012/0259649 A1 | 10/2012 | Mallon et al. |
| 2012/0278759 A1 | 11/2012 | Curl et al. |
| 2012/0295240 A1 | 11/2012 | Walker et al. |
| 2012/0296455 A1 | 11/2012 | Ohnemus et al. |
| 2012/0310667 A1 | 12/2012 | Altman et al. |
| 2013/0066647 A1 | 3/2013 | Andrie |
| 2013/0079925 A1 | 3/2013 | Alaklabi et al. |
| 2013/0083054 A1 | 4/2013 | Bayouk |
| 2013/0108594 A1 | 5/2013 | Martin-Rendon et al. |
| 2013/0110545 A1 | 5/2013 | Smallwood |
| 2013/0123667 A1 | 5/2013 | Komatireddy et al. |
| 2013/0137550 A1 | 5/2013 | Skinner et al. |
| 2013/0137552 A1 | 5/2013 | Kemp et al. |
| 2013/0158368 A1 | 6/2013 | Pacione |
| 2013/0165195 A1 | 6/2013 | Watterson |
| 2013/0178334 A1 | 7/2013 | Brammer |
| 2013/0211281 A1 | 8/2013 | Ross et al. |
| 2013/0253943 A1 | 9/2013 | Lee et al. |
| 2013/0274069 A1 | 10/2013 | Watterson et al. |
| 2013/0296987 A1 | 11/2013 | Rogers et al. |
| 2013/0318027 A1 | 11/2013 | Almogy et al. |
| 2013/0332616 A1 | 12/2013 | Landwehr |
| 2013/0345025 A1 | 12/2013 | van der Merwe |
| 2014/0006042 A1 | 1/2014 | Keefe et al. |
| 2014/0011640 A1 | 1/2014 | Dugan |
| 2014/0031174 A1 | 1/2014 | Huang |
| 2014/0038781 A1 | 2/2014 | Foley et al. |
| 2014/0062900 A1 | 3/2014 | Kaula et al. |
| 2014/0074179 A1 | 3/2014 | Heldman et al. |
| 2014/0089836 A1 | 3/2014 | Damani et al. |
| 2014/0108035 A1 | 4/2014 | Akbay |
| 2014/0113261 A1 | 4/2014 | Akiba |
| 2014/0113768 A1 | 4/2014 | Lin et al. |
| 2014/0135173 A1 | 5/2014 | Watterson |
| 2014/0149129 A1* | 5/2014 | Getchius ............... G06Q 40/08 |
| | | 705/2 |
| 2014/0155129 A1 | 6/2014 | Dugan |
| 2014/0163439 A1 | 6/2014 | Uryash et al. |
| 2014/0172442 A1 | 6/2014 | Broderick |
| 2014/0172460 A1 | 6/2014 | Kohli |
| 2014/0172514 A1 | 6/2014 | Schumann et al. |
| 2014/0188009 A1 | 7/2014 | Lange et al. |
| 2014/0194250 A1 | 7/2014 | Reich et al. |
| 2014/0194251 A1 | 7/2014 | Reich et al. |
| 2014/0200414 A1 | 7/2014 | Osorio |
| 2014/0207264 A1 | 7/2014 | Quy |
| 2014/0207486 A1 | 7/2014 | Carty et al. |
| 2014/0228649 A1 | 8/2014 | Rayner et al. |
| 2014/0246499 A1 | 9/2014 | Proud et al. |
| 2014/0256511 A1 | 9/2014 | Smith |
| 2014/0257837 A1 | 9/2014 | Walker et al. |
| 2014/0274565 A1 | 9/2014 | Boyette et al. |
| 2014/0274622 A1 | 9/2014 | Leonhard |
| 2014/0275816 A1 | 9/2014 | Sandmore |
| 2014/0303540 A1 | 10/2014 | Baym |
| 2014/0309083 A1 | 10/2014 | Dugan |
| 2014/0315689 A1 | 10/2014 | Vauquelin et al. |
| 2014/0322686 A1 | 10/2014 | Kang |
| 2014/0347265 A1 | 11/2014 | Aimone et al. |
| 2014/0371816 A1 | 12/2014 | Matos |
| 2014/0372133 A1 | 12/2014 | Austrum et al. |
| 2015/0025816 A1 | 1/2015 | Ross |
| 2015/0045700 A1 | 2/2015 | Cavanagh et al. |
| 2015/0046192 A1 | 2/2015 | Raduchel |
| 2015/0051721 A1 | 2/2015 | Cheng |
| 2015/0065213 A1 | 3/2015 | Dugan |
| 2015/0073814 A1* | 3/2015 | Linebaugh ............. G16H 20/30 |
| | | 705/2 |
| 2015/0088544 A1 | 3/2015 | Goldberg |
| 2015/0094192 A1 | 4/2015 | Skwortsow et al. |
| 2015/0099458 A1 | 4/2015 | Weisner et al. |
| 2015/0099952 A1 | 4/2015 | Lain et al. |
| 2015/0111644 A1 | 4/2015 | Larson |
| 2015/0112230 A1 | 4/2015 | Iglesias |
| 2015/0112702 A1 | 4/2015 | Joao et al. |
| 2015/0130830 A1 | 5/2015 | Nagasaki |
| 2015/0141200 A1 | 5/2015 | Murray et al. |
| 2015/0142142 A1 | 5/2015 | Aguilera et al. |
| 2015/0149217 A1 | 5/2015 | Kaburagi |
| 2015/0151162 A1 | 6/2015 | Dugan |
| 2015/0157938 A1 | 6/2015 | Domansky et al. |
| 2015/0158549 A1 | 6/2015 | Gros et al. |
| 2015/0161331 A1 | 6/2015 | Oleynik |
| 2015/0161876 A1* | 6/2015 | Castillo .............. G08B 21/0446 |
| | | 340/539.11 |
| 2015/0174446 A1 | 6/2015 | Chiang |
| 2015/0196804 A1 | 7/2015 | Koduri |

(56) References Cited

U.S. PATENT DOCUMENTS

| | | | |
|---|---|---|---|
| 2015/0196805 A1 | 7/2015 | Koduri | |
| 2015/0199494 A1 | 7/2015 | Koduri | |
| 2015/0217056 A1 | 8/2015 | Kadavy et al. | |
| 2015/0251074 A1 | 9/2015 | Ahmed et al. | |
| 2015/0257679 A1 | 9/2015 | Ross | |
| 2015/0265209 A1 | 9/2015 | Zhang | |
| 2015/0290061 A1 | 10/2015 | Stafford et al. | |
| 2015/0331997 A1 | 11/2015 | Joao | |
| 2015/0335950 A1 | 11/2015 | Eder | |
| 2015/0335951 A1 | 11/2015 | Eder | |
| 2015/0339442 A1 | 11/2015 | Oleynik | |
| 2015/0341812 A1 | 11/2015 | Dion et al. | |
| 2015/0351664 A1 | 12/2015 | Ross | |
| 2015/0351665 A1 | 12/2015 | Ross | |
| 2015/0360069 A1 | 12/2015 | Marti et al. | |
| 2015/0379232 A1 | 12/2015 | Mainwaring et al. | |
| 2015/0379430 A1 | 12/2015 | Dirac et al. | |
| 2016/0004820 A1* | 1/2016 | Moore | G16H 15/00 |
| | | | 705/3 |
| 2016/0007885 A1 | 1/2016 | Basta et al. | |
| 2016/0015995 A1 | 1/2016 | Leung et al. | |
| 2016/0045170 A1 | 2/2016 | Migita | |
| 2016/0081594 A1 | 3/2016 | Gaddipati | |
| 2016/0086500 A1 | 3/2016 | Kaleal, III | |
| 2016/0096073 A1 | 4/2016 | Rahman et al. | |
| 2016/0117471 A1 | 4/2016 | Belt et al. | |
| 2016/0132643 A1* | 5/2016 | Radhakrishna | G16H 70/60 |
| | | | 705/3 |
| 2016/0140319 A1 | 5/2016 | Stark et al. | |
| 2016/0143593 A1 | 5/2016 | Fu et al. | |
| 2016/0151670 A1 | 6/2016 | Dugan | |
| 2016/0158534 A1* | 6/2016 | Guarraia | A61N 1/0456 |
| | | | 607/134 |
| 2016/0166833 A1 | 6/2016 | Bum | |
| 2016/0166881 A1 | 6/2016 | Ridgel et al. | |
| 2016/0193306 A1 | 7/2016 | Rabovsky et al. | |
| 2016/0197918 A1* | 7/2016 | Turgeman | G06F 21/316 |
| | | | 726/4 |
| 2016/0213924 A1 | 7/2016 | Coleman | |
| 2016/0250519 A1 | 9/2016 | Watterson | |
| 2016/0275259 A1 | 9/2016 | Nolan et al. | |
| 2016/0287166 A1 | 10/2016 | Tran | |
| 2016/0302666 A1 | 10/2016 | Shaya | |
| 2016/0302721 A1 | 10/2016 | Wiedenhoefer et al. | |
| 2016/0317869 A1 | 11/2016 | Dugan | |
| 2016/0322078 A1 | 11/2016 | Bose et al. | |
| 2016/0325140 A1 | 11/2016 | Wu | |
| 2016/0332028 A1 | 11/2016 | Melnik | |
| 2016/0345841 A1 | 12/2016 | Jang et al. | |
| 2016/0354636 A1 | 12/2016 | Jang | |
| 2016/0361025 A1 | 12/2016 | Reicher et al. | |
| 2016/0361597 A1 | 12/2016 | Cole et al. | |
| 2016/0373477 A1 | 12/2016 | Moyle | |
| 2017/0004260 A1 | 1/2017 | Moturu et al. | |
| 2017/0011179 A1 | 1/2017 | Arshad et al. | |
| 2017/0017760 A1* | 1/2017 | Freese | G16H 40/63 |
| 2017/0032092 A1 | 2/2017 | Mink et al. | |
| 2017/0033375 A1 | 2/2017 | Ohmori et al. | |
| 2017/0042467 A1 | 2/2017 | Herr et al. | |
| 2017/0043160 A1 | 2/2017 | Goodall et al. | |
| 2017/0046488 A1 | 2/2017 | Pereira | |
| 2017/0065851 A1 | 3/2017 | Deluca et al. | |
| 2017/0069223 A1 | 3/2017 | Cramer et al. | |
| 2017/0080320 A1 | 3/2017 | Smith | |
| 2017/0091422 A1 | 3/2017 | Kumar et al. | |
| 2017/0095670 A1 | 4/2017 | Ghaffari et al. | |
| 2017/0095692 A1 | 4/2017 | Chang et al. | |
| 2017/0095693 A1 | 4/2017 | Chang et al. | |
| 2017/0100637 A1 | 4/2017 | Princen et al. | |
| 2017/0106242 A1 | 4/2017 | Dugan | |
| 2017/0128769 A1 | 5/2017 | Long et al. | |
| 2017/0132947 A1 | 5/2017 | Maeda et al. | |
| 2017/0136296 A1 | 5/2017 | Barrera et al. | |
| 2017/0136298 A1 | 5/2017 | Bae | |
| 2017/0143261 A1 | 5/2017 | Wiedenhoefer et al. | |
| 2017/0147752 A1 | 5/2017 | Toru | |
| 2017/0147789 A1 | 5/2017 | Wiedenhoefer et al. | |
| 2017/0148297 A1 | 5/2017 | Ross | |
| 2017/0168555 A1 | 6/2017 | Munoz et al. | |
| 2017/0169177 A1 | 6/2017 | Beale | |
| 2017/0173391 A1 | 6/2017 | Wiebe | |
| 2017/0181698 A1 | 6/2017 | Wiedenhoefer et al. | |
| 2017/0190052 A1 | 7/2017 | Jaekel et al. | |
| 2017/0202724 A1 | 7/2017 | De Rossi | |
| 2017/0209766 A1 | 7/2017 | Riley et al. | |
| 2017/0220751 A1 | 8/2017 | Davis | |
| 2017/0228517 A1 | 8/2017 | Saliman et al. | |
| 2017/0235882 A1 | 8/2017 | Orlov et al. | |
| 2017/0235906 A1 | 8/2017 | Dorris et al. | |
| 2017/0243028 A1 | 8/2017 | LaFever et al. | |
| 2017/0258370 A1 | 9/2017 | Plotnik-Peleg et al. | |
| 2017/0262604 A1* | 9/2017 | Francois | G16H 10/60 |
| 2017/0266501 A1 | 9/2017 | Sanders et al. | |
| 2017/0270260 A1 | 9/2017 | Shetty | |
| 2017/0278209 A1 | 9/2017 | Olsen et al. | |
| 2017/0282015 A1 | 10/2017 | Wicks et al. | |
| 2017/0283508 A1 | 10/2017 | Demopulos et al. | |
| 2017/0286621 A1 | 10/2017 | Cox | |
| 2017/0296861 A1* | 10/2017 | Burkinshaw | A63B 71/02 |
| 2017/0300654 A1 | 10/2017 | Stein et al. | |
| 2017/0304024 A1 | 10/2017 | Nobrega | |
| 2017/0312614 A1 | 11/2017 | Tran et al. | |
| 2017/0323481 A1 | 11/2017 | Tran et al. | |
| 2017/0329917 A1 | 11/2017 | McRaith et al. | |
| 2017/0329933 A1 | 11/2017 | Brust | |
| 2017/0333755 A1 | 11/2017 | Rider | |
| 2017/0337033 A1 | 11/2017 | Duyan et al. | |
| 2017/0337334 A1 | 11/2017 | Stanczak | |
| 2017/0344726 A1 | 11/2017 | Duffy et al. | |
| 2017/0347923 A1 | 12/2017 | Roh | |
| 2017/0352157 A1 | 12/2017 | Madabhushi | |
| 2017/0360586 A1 | 12/2017 | Dempers et al. | |
| 2017/0361165 A1 | 12/2017 | Miller et al. | |
| 2017/0367606 A1 | 12/2017 | Lee | |
| 2017/0368413 A1 | 12/2017 | Shavit | |
| 2018/0017806 A1 | 1/2018 | Wang et al. | |
| 2018/0036591 A1 | 2/2018 | King et al. | |
| 2018/0036593 A1 | 2/2018 | Ridgel et al. | |
| 2018/0052962 A1 | 2/2018 | Van Der Koijk et al. | |
| 2018/0052968 A1 | 2/2018 | Hickle et al. | |
| 2018/0056104 A1 | 3/2018 | Cromie et al. | |
| 2018/0056130 A1 | 3/2018 | Bitran et al. | |
| 2018/0060494 A1 | 3/2018 | Dias et al. | |
| 2018/0070864 A1 | 3/2018 | Schuster | |
| 2018/0071572 A1 | 3/2018 | Gomberg et al. | |
| 2018/0075205 A1 | 3/2018 | Moturu et al. | |
| 2018/0078182 A1 | 3/2018 | Chen | |
| 2018/0078843 A1 | 3/2018 | Tran et al. | |
| 2018/0085615 A1 | 3/2018 | Astolfi et al. | |
| 2018/0089385 A1 | 3/2018 | Gupta | |
| 2018/0096111 A1 | 4/2018 | Wells et al. | |
| 2018/0099178 A1 | 4/2018 | Schaefer et al. | |
| 2018/0102190 A1 | 4/2018 | Jogue et al. | |
| 2018/0103859 A1 | 4/2018 | Provenzano | |
| 2018/0113985 A1 | 4/2018 | Gandy et al. | |
| 2018/0116741 A1 | 5/2018 | Garcia Kilroy et al. | |
| 2018/0117417 A1* | 5/2018 | Davis | A63B 24/0075 |
| 2018/0130555 A1* | 5/2018 | Chronis | G06V 20/64 |
| 2018/0133551 A1 | 5/2018 | Chang | |
| 2018/0140927 A1 | 5/2018 | Kito | |
| 2018/0146870 A1 | 5/2018 | Shemesh | |
| 2018/0177612 A1 | 6/2018 | Trabish et al. | |
| 2018/0178061 A1 | 6/2018 | O'larte et al. | |
| 2018/0199855 A1 | 7/2018 | Odame et al. | |
| 2018/0200577 A1 | 7/2018 | Dugan | |
| 2018/0220935 A1 | 8/2018 | Tadano et al. | |
| 2018/0228682 A1 | 8/2018 | Bayerlein et al. | |
| 2018/0232492 A1 | 8/2018 | Al-Alul et al. | |
| 2018/0236307 A1 | 8/2018 | Hyde et al. | |
| 2018/0240552 A1 | 8/2018 | Tuyl et al. | |
| 2018/0253991 A1 | 9/2018 | Tang et al. | |
| 2018/0255110 A1 | 9/2018 | Dowlatkhah et al. | |
| 2018/0256079 A1 | 9/2018 | Yang et al. | |
| 2018/0263530 A1 | 9/2018 | Jung | |

(56) References Cited

U.S. PATENT DOCUMENTS

| | | |
|---|---|---|
| 2018/0263535 A1 | 9/2018 | Cramer |
| 2018/0263552 A1 | 9/2018 | Graman et al. |
| 2018/0264312 A1 | 9/2018 | Pompile et al. |
| 2018/0271432 A1 | 9/2018 | Auchinleck et al. |
| 2018/0272184 A1 | 9/2018 | Vassilaros et al. |
| 2018/0280784 A1 | 10/2018 | Romeo et al. |
| 2018/0290017 A1 | 10/2018 | Fung |
| 2018/0296143 A1 | 10/2018 | Anderson et al. |
| 2018/0296157 A1 | 10/2018 | Bleich et al. |
| 2018/0318122 A1 | 11/2018 | LeCursi et al. |
| 2018/0326243 A1 | 11/2018 | Badi et al. |
| 2018/0330058 A1 | 11/2018 | Bates |
| 2018/0330810 A1 | 11/2018 | Gamarnik |
| 2018/0330824 A1 | 11/2018 | Athey et al. |
| 2018/0353812 A1 | 12/2018 | Lannon et al. |
| 2018/0360340 A1 | 12/2018 | Rehse et al. |
| 2018/0366225 A1 | 12/2018 | Mansi et al. |
| 2018/0373844 A1 | 12/2018 | Ferrandez-Escamez et al. |
| 2019/0005195 A1 | 1/2019 | Peterson |
| 2019/0009135 A1 | 1/2019 | Wu |
| 2019/0019163 A1 | 1/2019 | Batey et al. |
| 2019/0019573 A1 | 1/2019 | Lake et al. |
| 2019/0019578 A1 | 1/2019 | Vaccaro |
| 2019/0030415 A1 | 1/2019 | Volpe, Jr. |
| 2019/0031284 A1 | 1/2019 | Fuchs |
| 2019/0046794 A1 | 2/2019 | Goodall et al. |
| 2019/0060708 A1 | 2/2019 | Fung |
| 2019/0065970 A1* | 2/2019 | Bonutti ................. G16H 20/10 |
| 2019/0066832 A1 | 2/2019 | Kang et al. |
| 2019/0076701 A1 | 3/2019 | Dugan |
| 2019/0080802 A1* | 3/2019 | Ziobro ................. G16H 50/30 |
| 2019/0083846 A1 | 3/2019 | Eder |
| 2019/0088356 A1 | 3/2019 | Oliver et al. |
| 2019/0090744 A1 | 3/2019 | Mahfouz |
| 2019/0096534 A1 | 3/2019 | Joao |
| 2019/0105551 A1* | 4/2019 | Ray ..................... G06V 40/197 |
| 2019/0108912 A1 | 4/2019 | Spurlock, III |
| 2019/0111299 A1 | 4/2019 | Radcliffe et al. |
| 2019/0115097 A1 | 4/2019 | Macoviak et al. |
| 2019/0117156 A1 | 4/2019 | Howard et al. |
| 2019/0118038 A1 | 4/2019 | Tana et al. |
| 2019/0118066 A1 | 4/2019 | Cardona |
| 2019/0126099 A1 | 5/2019 | Hoang |
| 2019/0132948 A1 | 5/2019 | Longinotti-Buitoni et al. |
| 2019/0134454 A1 | 5/2019 | Mahoney et al. |
| 2019/0137988 A1 | 5/2019 | Cella et al. |
| 2019/0143191 A1 | 5/2019 | Ran et al. |
| 2019/0143193 A1 | 5/2019 | Kim |
| 2019/0145774 A1* | 5/2019 | Ellis ...................... G16H 10/20 |
| | | 482/8 |
| 2019/0163876 A1 | 5/2019 | Remme et al. |
| 2019/0167988 A1 | 6/2019 | Shahriari et al. |
| 2019/0172587 A1 | 6/2019 | Park et al. |
| 2019/0175988 A1 | 6/2019 | Volterrani et al. |
| 2019/0183715 A1 | 6/2019 | Kapure et al. |
| 2019/0200920 A1 | 7/2019 | Tien et al. |
| 2019/0209891 A1 | 7/2019 | Fung |
| 2019/0214119 A1 | 7/2019 | Wachira et al. |
| 2019/0223797 A1 | 7/2019 | Tran |
| 2019/0224528 A1 | 7/2019 | Omid-Zohoor et al. |
| 2019/0228856 A1 | 7/2019 | Leifer |
| 2019/0232108 A1 | 8/2019 | Kovach et al. |
| 2019/0240103 A1 | 8/2019 | Hepler et al. |
| 2019/0240541 A1 | 8/2019 | Denton et al. |
| 2019/0244540 A1 | 8/2019 | Errante et al. |
| 2019/0247718 A1 | 8/2019 | Blevins |
| 2019/0251456 A1 | 8/2019 | Constantin |
| 2019/0261959 A1 | 8/2019 | Frankel |
| 2019/0262084 A1 | 8/2019 | Roh |
| 2019/0269343 A1 | 9/2019 | Ramos Murguialday et al. |
| 2019/0274523 A1 | 9/2019 | Bates et al. |
| 2019/0275368 A1 | 9/2019 | Maroldi |
| 2019/0283247 A1 | 9/2019 | Chang |
| 2019/0290964 A1 | 9/2019 | Pren |
| 2019/0304584 A1 | 10/2019 | Savolainen |
| 2019/0307983 A1 | 10/2019 | Goldman |
| 2019/0314681 A1 | 10/2019 | Yang |
| 2019/0344123 A1 | 11/2019 | Rubin et al. |
| 2019/0354632 A1 | 11/2019 | Mital et al. |
| 2019/0362242 A1 | 11/2019 | Pillai et al. |
| 2019/0366146 A1 | 12/2019 | Tong et al. |
| 2019/0371472 A1 | 12/2019 | Blanchard |
| 2019/0385199 A1 | 12/2019 | Bender et al. |
| 2019/0388728 A1 | 12/2019 | Wang et al. |
| 2019/0392936 A1 | 12/2019 | Arric et al. |
| 2019/0392939 A1 | 12/2019 | Basta et al. |
| 2020/0005928 A1 | 1/2020 | Daniel |
| 2020/0015736 A1* | 1/2020 | Alhathal .................. A61B 5/11 |
| 2020/0034665 A1 | 1/2020 | Ghanta |
| 2020/0034707 A1* | 1/2020 | Kivatinos .............. G06Q 30/04 |
| 2020/0038703 A1 | 2/2020 | Cleary et al. |
| 2020/0051446 A1 | 2/2020 | Rubinstein |
| 2020/0054922 A1 | 2/2020 | Azaria |
| 2020/0066390 A1 | 2/2020 | Svendrys et al. |
| 2020/0085300 A1 | 3/2020 | Kwatra et al. |
| 2020/0090802 A1 | 3/2020 | Maron |
| 2020/0093418 A1 | 3/2020 | Kluger et al. |
| 2020/0121987 A1 | 4/2020 | Loh |
| 2020/0129808 A1 | 4/2020 | Fomin |
| 2020/0139194 A1 | 5/2020 | Min |
| 2020/0143922 A1 | 5/2020 | Chekroud et al. |
| 2020/0151595 A1 | 5/2020 | Jayalath et al. |
| 2020/0151646 A1 | 5/2020 | De La Fuente Sanchez |
| 2020/0152339 A1 | 5/2020 | Pulitzer et al. |
| 2020/0160198 A1 | 5/2020 | Reeves et al. |
| 2020/0170876 A1 | 6/2020 | Kapure et al. |
| 2020/0176098 A1 | 6/2020 | Lucas et al. |
| 2020/0188774 A1 | 6/2020 | Fung |
| 2020/0197744 A1 | 6/2020 | Schweighofer |
| 2020/0221975 A1 | 7/2020 | Basta et al. |
| 2020/0237291 A1 | 7/2020 | Raja |
| 2020/0237452 A1 | 7/2020 | Wolf et al. |
| 2020/0261763 A1 | 8/2020 | Park |
| 2020/0267487 A1 | 8/2020 | Siva |
| 2020/0275886 A1 | 9/2020 | Mason |
| 2020/0289045 A1 | 9/2020 | Hacking et al. |
| 2020/0289046 A1 | 9/2020 | Hacking et al. |
| 2020/0289879 A1 | 9/2020 | Hacking et al. |
| 2020/0289880 A1 | 9/2020 | Hacking et al. |
| 2020/0289881 A1 | 9/2020 | Hacking et al. |
| 2020/0289889 A1 | 9/2020 | Hacking et al. |
| 2020/0293712 A1 | 9/2020 | Potts et al. |
| 2020/0303063 A1 | 9/2020 | Sharma et al. |
| 2020/0312447 A1 | 10/2020 | Bohn et al. |
| 2020/0320454 A1 | 10/2020 | Almashor |
| 2020/0334972 A1 | 10/2020 | Gopalakrishnan |
| 2020/0346072 A1 | 11/2020 | Shah |
| 2020/0353314 A1 | 11/2020 | Messinger |
| 2020/0357299 A1 | 11/2020 | Patel et al. |
| 2020/0365256 A1 | 11/2020 | Hayashitani et al. |
| 2020/0391080 A1 | 12/2020 | Powers |
| 2020/0395112 A1 | 12/2020 | Ronner |
| 2020/0398083 A1 | 12/2020 | Adelsheim |
| 2020/0401224 A1 | 12/2020 | Cotton |
| 2020/0402662 A1 | 12/2020 | Esmailian et al. |
| 2020/0410374 A1 | 12/2020 | White |
| 2020/0410385 A1 | 12/2020 | Otsuki |
| 2020/0410893 A1 | 12/2020 | Ridington |
| 2020/0411162 A1 | 12/2020 | Lien et al. |
| 2020/0411170 A1 | 12/2020 | Brown |
| 2021/0005224 A1 | 1/2021 | Rothschild et al. |
| 2021/0005319 A1 | 1/2021 | Otsuki et al. |
| 2021/0008413 A1 | 1/2021 | Asikainen et al. |
| 2021/0015560 A1 | 1/2021 | Boddington et al. |
| 2021/0027889 A1 | 1/2021 | Neil et al. |
| 2021/0035674 A1 | 2/2021 | Volosin et al. |
| 2021/0050086 A1 | 2/2021 | Rose et al. |
| 2021/0065855 A1 | 3/2021 | Pepin et al. |
| 2021/0074178 A1 | 3/2021 | Lan et al. |
| 2021/0076981 A1 | 3/2021 | Hacking et al. |
| 2021/0077860 A1 | 3/2021 | Posnack et al. |
| 2021/0077884 A1 | 3/2021 | De Las Casas Zolezzi et al. |
| 2021/0082554 A1 | 3/2021 | Kalia et al. |
| 2021/0093891 A1 | 4/2021 | Sheng |

(56) References Cited

U.S. PATENT DOCUMENTS

| 2021/0098099 A1 | 4/2021 | Neumann |
| 2021/0098129 A1 | 4/2021 | Neumann |
| 2021/0101051 A1 | 4/2021 | Posnack et al. |
| 2021/0113890 A1 | 4/2021 | Posnack et al. |
| 2021/0125696 A1 | 4/2021 | Liu et al. |
| 2021/0127974 A1 | 5/2021 | Mason et al. |
| 2021/0128080 A1 | 5/2021 | Mason et al. |
| 2021/0128255 A1 | 5/2021 | Mason et al. |
| 2021/0128978 A1 | 5/2021 | Gilstrom et al. |
| 2021/0134425 A1 | 5/2021 | Mason et al. |
| 2021/0134428 A1 | 5/2021 | Mason |
| 2021/0134429 A1 | 5/2021 | Mason |
| 2021/0134430 A1 | 5/2021 | Mason et al. |
| 2021/0134432 A1 | 5/2021 | Mason et al. |
| 2021/0134456 A1 | 5/2021 | Posnack et al. |
| 2021/0134457 A1 | 5/2021 | Mason et al. |
| 2021/0134458 A1 | 5/2021 | Mason et al. |
| 2021/0134463 A1 | 5/2021 | Mason et al. |
| 2021/0138304 A1 | 5/2021 | Mason et al. |
| 2021/0142875 A1 | 5/2021 | Mason et al. |
| 2021/0142893 A1 | 5/2021 | Guaneri et al. |
| 2021/0142898 A1 | 5/2021 | Mason et al. |
| 2021/0142903 A1 | 5/2021 | Mason et al. |
| 2021/0144074 A1 | 5/2021 | Guaneri et al. |
| 2021/0186419 A1 | 6/2021 | Van Ee et al. |
| 2021/0187348 A1* | 6/2021 | Phillips ................ A63B 22/025 |
| 2021/0202090 A1 | 7/2021 | ODonovan et al. |
| 2021/0202103 A1 | 7/2021 | Bostic et al. |
| 2021/0205660 A1 | 7/2021 | Shavit |
| 2021/0217516 A1 | 7/2021 | Nash |
| 2021/0236020 A1 | 8/2021 | Matijevich et al. |
| 2021/0240853 A1 | 8/2021 | Carlson |
| 2021/0241137 A1 | 8/2021 | Jain et al. |
| 2021/0244998 A1 | 8/2021 | Hacking et al. |
| 2021/0245003 A1 | 8/2021 | Turner |
| 2021/0251562 A1 | 8/2021 | Jain |
| 2021/0272677 A1 | 9/2021 | Barbee |
| 2021/0338469 A1 | 11/2021 | Dempers |
| 2021/0343384 A1 | 11/2021 | Purushothaman et al. |
| 2021/0345879 A1 | 11/2021 | Mason et al. |
| 2021/0345975 A1 | 11/2021 | Mason et al. |
| 2021/0350888 A1 | 11/2021 | Guaneri et al. |
| 2021/0350898 A1 | 11/2021 | Mason et al. |
| 2021/0350899 A1 | 11/2021 | Mason et al. |
| 2021/0350901 A1 | 11/2021 | Mason et al. |
| 2021/0350902 A1 | 11/2021 | Mason et al. |
| 2021/0350914 A1 | 11/2021 | Guaneri et al. |
| 2021/0350926 A1 | 11/2021 | Mason et al. |
| 2021/0354002 A1 | 11/2021 | Schaefer |
| 2021/0361514 A1 | 11/2021 | Choi et al. |
| 2021/0366587 A1 | 11/2021 | Mason et al. |
| 2021/0375425 A1 | 12/2021 | Zhang |
| 2021/0383909 A1 | 12/2021 | Mason et al. |
| 2021/0391091 A1 | 12/2021 | Mason |
| 2021/0394011 A1 | 12/2021 | Neuhaus et al. |
| 2021/0398668 A1 | 12/2021 | Chock et al. |
| 2021/0406738 A1 | 12/2021 | O'Donncha et al. |
| 2021/0407670 A1 | 12/2021 | Mason et al. |
| 2021/0407681 A1 | 12/2021 | Mason et al. |
| 2022/0000556 A1 | 1/2022 | Casey et al. |
| 2022/0015838 A1 | 1/2022 | Posnack |
| 2022/0016480 A1 | 1/2022 | Bissonnette et al. |
| 2022/0016482 A1 | 1/2022 | Bissonnette |
| 2022/0016484 A1 | 1/2022 | Bissonnette et al. |
| 2022/0016485 A1 | 1/2022 | Bissonnette |
| 2022/0016486 A1 | 1/2022 | Bissonnette et al. |
| 2022/0020469 A1 | 1/2022 | Tanner |
| 2022/0044806 A1 | 2/2022 | Sanders et al. |
| 2022/0047921 A1 | 2/2022 | Bissonnette |
| 2022/0066548 A1 | 3/2022 | Helot |
| 2022/0079690 A1 | 3/2022 | Mason et al. |
| 2022/0080256 A1 | 3/2022 | Arn et al. |
| 2022/0080265 A1 | 3/2022 | Watterson |
| 2022/0096006 A1 | 3/2022 | Wu et al. |
| 2022/0105384 A1 | 4/2022 | Hacking et al. |
| 2022/0105385 A1 | 4/2022 | Hacking et al. |
| 2022/0105390 A1 | 4/2022 | Yuasa |
| 2022/0115133 A1 | 4/2022 | Mason et al. |
| 2022/0117514 A1 | 4/2022 | Kuhn et al. |
| 2022/0118218 A1 | 4/2022 | Bense et al. |
| 2022/0122724 A1 | 4/2022 | Durlach et al. |
| 2022/0126169 A1 | 4/2022 | Mason |
| 2022/0133576 A1 | 5/2022 | Choi et al. |
| 2022/0148725 A1 | 5/2022 | Mason et al. |
| 2022/0158916 A1 | 5/2022 | Mason et al. |
| 2022/0165398 A1 | 5/2022 | Avila-Hernandez et al. |
| 2022/0176039 A1 | 6/2022 | Lintereur et al. |
| 2022/0181004 A1 | 6/2022 | Zilca et al. |
| 2022/0193491 A1 | 6/2022 | Mason |
| 2022/0230729 A1 | 7/2022 | Mason |
| 2022/0238222 A1 | 7/2022 | Neuberg |
| 2022/0238223 A1 | 7/2022 | Mason |
| 2022/0258935 A1 | 8/2022 | Kraft |
| 2022/0262483 A1 | 8/2022 | Rosenberg et al. |
| 2022/0262504 A1 | 8/2022 | Bratty et al. |
| 2022/0266094 A1 | 8/2022 | Mason et al. |
| 2022/0270738 A1 | 8/2022 | Mason et al. |
| 2022/0273985 A1 | 9/2022 | Jeong et al. |
| 2022/0273986 A1 | 9/2022 | Mason |
| 2022/0288460 A1 | 9/2022 | Mason |
| 2022/0288461 A1 | 9/2022 | Ashley et al. |
| 2022/0288462 A1 | 9/2022 | Ashley et al. |
| 2022/0293257 A1 | 9/2022 | Guaneri et al. |
| 2022/0300787 A1 | 9/2022 | Wall et al. |
| 2022/0304881 A1 | 9/2022 | Choi et al. |
| 2022/0304882 A1 | 9/2022 | Choi |
| 2022/0305291 A1 | 9/2022 | Hibbard |
| 2022/0305328 A1 | 9/2022 | Choi et al. |
| 2022/0314072 A1 | 10/2022 | Bissonnette et al. |
| 2022/0314075 A1 | 10/2022 | Mason et al. |
| 2022/0323826 A1 | 10/2022 | Khurana |
| 2022/0327714 A1 | 10/2022 | Cook et al. |
| 2022/0327807 A1 | 10/2022 | Cook et al. |
| 2022/0328181 A1 | 10/2022 | Mason et al. |
| 2022/0330823 A1 | 10/2022 | Janssen |
| 2022/0331663 A1 | 10/2022 | Mason |
| 2022/0336077 A1 | 10/2022 | Chen et al. |
| 2022/0338761 A1 | 10/2022 | Maddahi et al. |
| 2022/0339052 A1 | 10/2022 | Kim |
| 2022/0339501 A1 | 10/2022 | Mason et al. |
| 2022/0370851 A1 | 11/2022 | Guidarelli et al. |
| 2022/0384010 A1 | 12/2022 | Kanayama |
| 2022/0384012 A1 | 12/2022 | Mason |
| 2022/0392591 A1 | 12/2022 | Guaneri et al. |
| 2022/0395232 A1 | 12/2022 | Locke |
| 2022/0401783 A1 | 12/2022 | Choi |
| 2022/0415469 A1 | 12/2022 | Mason |
| 2022/0415471 A1 | 12/2022 | Mason |
| 2023/0001268 A1 | 1/2023 | Bissonnette et al. |
| 2023/0013530 A1 | 1/2023 | Mason |
| 2023/0014598 A1 | 1/2023 | Mason et al. |
| 2023/0029639 A1 | 2/2023 | Roy |
| 2023/0047253 A1 | 2/2023 | Gnanasambandam et al. |
| 2023/0048040 A1 | 2/2023 | Hacking et al. |
| 2023/0051751 A1 | 2/2023 | Hacking et al. |
| 2023/0055078 A1 | 2/2023 | Malcolm |
| 2023/0058605 A1 | 2/2023 | Mason |
| 2023/0060039 A1 | 2/2023 | Mason |
| 2023/0072368 A1 | 3/2023 | Mason |
| 2023/0078793 A1 | 3/2023 | Mason |
| 2023/0119461 A1 | 4/2023 | Mason |
| 2023/0190100 A1 | 6/2023 | Stump |
| 2023/0197240 A1 | 6/2023 | Rosenberg |
| 2023/0201656 A1 | 6/2023 | Hacking et al. |
| 2023/0207097 A1 | 6/2023 | Mason |
| 2023/0207124 A1 | 6/2023 | Walsh et al. |
| 2023/0215539 A1 | 7/2023 | Rosenberg et al. |
| 2023/0215552 A1 | 7/2023 | Khotilovich et al. |
| 2023/0218950 A1 | 7/2023 | Belson et al. |
| 2023/0245747 A1 | 8/2023 | Rosenberg et al. |
| 2023/0245748 A1 | 8/2023 | Rosenberg et al. |
| 2023/0245750 A1 | 8/2023 | Rosenberg et al. |
| 2023/0245751 A1 | 8/2023 | Rosenberg et al. |
| 2023/0249599 A1 | 8/2023 | Nicola |

(56) References Cited

U.S. PATENT DOCUMENTS

| 2023/0253089 A1 | 8/2023 | Rosenberg et al. |
|---|---|---|
| 2023/0255555 A1 | 8/2023 | Sundaram et al. |
| 2023/0263428 A1 | 8/2023 | Hull et al. |
| 2023/0274813 A1 | 8/2023 | Rosenberg et al. |
| 2023/0282329 A1 | 9/2023 | Mason et al. |
| 2023/0364472 A1 | 11/2023 | Posnack |
| 2023/0368886 A1 | 11/2023 | Rosenberg |
| 2023/0377710 A1 | 11/2023 | Chen et al. |
| 2023/0377711 A1 | 11/2023 | Rosenberg |
| 2023/0377712 A1 | 11/2023 | Rosenberg |
| 2023/0386639 A1 | 11/2023 | Rosenberg |
| 2023/0390627 A1 | 12/2023 | Bolton |
| 2023/0395231 A1 | 12/2023 | Rosenberg |
| 2023/0395232 A1 | 12/2023 | Rosenberg |
| 2024/0029856 A1 | 1/2024 | Rosenberg |
| 2024/0058651 A1 | 2/2024 | Bissonnette |
| 2024/0177846 A1 | 5/2024 | Gnanasambandam |
| 2024/0203580 A1 | 6/2024 | Mason |

FOREIGN PATENT DOCUMENTS

| CN | 2885238 Y | 4/2007 |
|---|---|---|
| CN | 101964151 A | 2/2011 |
| CN | 201889024 U | 7/2011 |
| CN | 102670381 A | 9/2012 |
| CN | 103263336 A | 8/2013 |
| CN | 103390357 A | 11/2013 |
| CN | 103473631 A | 12/2013 |
| CN | 103488880 A | 1/2014 |
| CN | 103501328 A | 1/2014 |
| CN | 103721343 A | 4/2014 |
| CN | 203677851 U | 7/2014 |
| CN | 104335211 A | 2/2015 |
| CN | 105263448 A | 1/2016 |
| CN | 105683977 A | 6/2016 |
| CN | 103136447 B | 8/2016 |
| CN | 105894088 A | 8/2016 |
| CN | 105930668 A | 9/2016 |
| CN | 205626871 U | 10/2016 |
| CN | 106127646 A | 11/2016 |
| CN | 106236502 A | 12/2016 |
| CN | 106510985 A | 3/2017 |
| CN | 106621195 A | 5/2017 |
| CN | 107066819 A | 8/2017 |
| CN | 107430641 A | 12/2017 |
| CN | 107551475 A | 1/2018 |
| CN | 107736982 A | 2/2018 |
| CN | 107930021 A | 4/2018 |
| CN | 108078737 A | 5/2018 |
| CN | 208224811 A | 12/2018 |
| CN | 109191954 A | 1/2019 |
| CN | 109363887 A | 2/2019 |
| CN | 208573971 U | 3/2019 |
| CN | 110148472 A | 8/2019 |
| CN | 110201358 A | 9/2019 |
| CN | 110215188 A | 9/2019 |
| CN | 110322957 A | 10/2019 |
| CN | 110808092 A | 2/2020 |
| CN | 110931103 A | 3/2020 |
| CN | 110993057 A | 4/2020 |
| CN | 111105859 A | 5/2020 |
| CN | 111111110 A | 5/2020 |
| CN | 111370088 A | 7/2020 |
| CN | 111460305 A | 7/2020 |
| CN | 111790111 A | 10/2020 |
| CN | 112071393 A | 12/2020 |
| CN | 212141371 U | 12/2020 |
| CN | 112289425 A | 1/2021 |
| CN | 212624809 U | 2/2021 |
| CN | 112603295 A | 4/2021 |
| CN | 213190965 U | 5/2021 |
| CN | 113384850 A | 9/2021 |
| CN | 113499572 A | 10/2021 |
| CN | 215136488 U | 12/2021 |
| CN | 113885361 A | 1/2022 |
| CN | 114049961 A | 2/2022 |
| CN | 114203274 A | 3/2022 |
| CN | 216258145 U | 4/2022 |
| CN | 114632302 A | 6/2022 |
| CN | 114694824 A | 7/2022 |
| CN | 114898832 A | 8/2022 |
| CN | 114983760 A | 9/2022 |
| CN | 217472652 U | 9/2022 |
| CN | 110270062 B | 10/2022 |
| CN | 218420859 U | 2/2023 |
| CN | 115954081 A | 4/2023 |
| DE | 102018202497 A1 | 8/2018 |
| DE | 102018211212 A1 | 1/2019 |
| DE | 102019108425 B3 | 8/2020 |
| EP | 0383137 A2 | 8/1990 |
| EP | 0919259 A1 | 6/1999 |
| EP | 1159989 A1 | 12/2001 |
| EP | 1391179 A1 | 2/2004 |
| EP | 1968028 | 9/2008 |
| EP | 2575064 A1 | 4/2013 |
| EP | 1909730 B1 | 4/2014 |
| EP | 2815242 A4 | 12/2014 |
| EP | 2869805 A | 5/2015 |
| EP | 2997951 A1 | 3/2016 |
| EP | 2688472 B1 | 4/2016 |
| EP | 3323473 A1 | 5/2018 |
| EP | 3547322 A1 | 10/2019 |
| EP | 3627514 A1 | 3/2020 |
| EP | 3671700 A1 | 6/2020 |
| EP | 3688537 A1 | 8/2020 |
| EP | 3731733 A1 | 11/2020 |
| EP | 3984508 A1 | 4/2022 |
| EP | 3984509 A1 | 4/2022 |
| EP | 3984510 A1 | 4/2022 |
| EP | 3984511 A1 | 4/2022 |
| EP | 3984512 A1 | 4/2022 |
| EP | 3984513 A1 | 4/2022 |
| EP | 4054699 A1 | 9/2022 |
| EP | 4112033 A1 | 1/2023 |
| FR | 3127393 A1 | 3/2023 |
| GB | 2512431 A | 10/2014 |
| GB | 2591542 B | 3/2022 |
| IN | 201811043670 A | 7/2018 |
| JP | 2000005339 A | 1/2000 |
| JP | 2003225875 A | 8/2003 |
| JP | 2005227928 A | 8/2005 |
| JP | 2005227928 A1 | 8/2005 |
| JP | 2009112336 A | 5/2009 |
| JP | 2013515995 A | 5/2013 |
| JP | 2014104139 A | 6/2014 |
| JP | 3193662 U | 10/2014 |
| JP | 3198173 U | 6/2015 |
| JP | 5804063 B2 | 11/2015 |
| JP | 6659831 B2 | 10/2017 |
| JP | 2018102842 A | 7/2018 |
| JP | 2019028647 A | 2/2019 |
| JP | 2019134909 A | 8/2019 |
| JP | 6573739 B1 | 9/2019 |
| JP | 2020057082 A | 4/2020 |
| JP | 6710357 B1 | 6/2020 |
| JP | 6775757 B1 | 10/2020 |
| JP | 2021026768 A | 2/2021 |
| JP | 2021027917 A | 2/2021 |
| JP | 6871379 B2 | 5/2021 |
| JP | 2022521378 A | 4/2022 |
| JP | 3238491 U | 7/2022 |
| JP | 7198364 B2 | 12/2022 |
| JP | 7202474 B2 | 1/2023 |
| JP | 7231750 B2 | 3/2023 |
| JP | 7231751 B2 | 3/2023 |
| JP | 7231752 B2 | 3/2023 |
| KR | 20020009724 A | 2/2002 |
| KR | 200276919 Y1 | 5/2002 |
| KR | 20020065253 A | 8/2002 |
| KR | 100582596 B1 | 5/2006 |
| KR | 101042258 B1 | 6/2011 |
| KR | 101258250 B1 | 4/2013 |
| KR | 101325581 B1 | 11/2013 |
| KR | 20140128630 A | 11/2014 |

(56)  References Cited

FOREIGN PATENT DOCUMENTS

| | | | |
|---|---|---|---|
| KR | 20150017693 A | 2/2015 |
| KR | 20150078191 A | 7/2015 |
| KR | 101580071 B1 | 12/2015 |
| KR | 101647620 B1 | 8/2016 |
| KR | 20160093990 A | 8/2016 |
| KR | 20170038837 A | 4/2017 |
| KR | 20180004928 A | 1/2018 |
| KR | 20190011885 A | 2/2019 |
| KR | 20190029175 A | 3/2019 |
| KR | 101988167 B1 | 6/2019 |
| KR | 102116664 B1 | 7/2019 |
| KR | 101969392 B1 | 8/2019 |
| KR | 102055279 B1 | 12/2019 |
| KR | 20200019548 A | 2/2020 |
| KR | 102088333 B1 | 3/2020 |
| KR | 102116968 B1 | 3/2020 |
| KR | 20200025290 A | 3/2020 |
| KR | 20200029180 A | 3/2020 |
| KR | 102097190 B1 | 4/2020 |
| KR | 102162522 B1 | 4/2020 |
| KR | 102142713 B1 | 5/2020 |
| KR | 20200056233 A | 5/2020 |
| KR | 102120828 B1 | 6/2020 |
| KR | 102121586 B1 | 6/2020 |
| KR | 20200119665 A | 10/2020 |
| KR | 102173553 B1 | 11/2020 |
| KR | 102180079 B1 | 11/2020 |
| KR | 102224618 B1 | 11/2020 |
| KR | 102188766 B1 | 12/2020 |
| KR | 102196793 B1 | 12/2020 |
| KR | 20210006212 A | 1/2021 |
| KR | 102224188 B1 | 3/2021 |
| KR | 102246049 B1 | 4/2021 |
| KR | 102246050 B1 | 4/2021 |
| KR | 102246051 B1 | 4/2021 |
| KR | 102246052 B1 | 4/2021 |
| KR | 20210052028 A | 5/2021 |
| KR | 102264498 B1 | 6/2021 |
| KR | 102352602 B1 | 1/2022 |
| KR | 102352603 B1 | 1/2022 |
| KR | 102352604 B1 | 1/2022 |
| KR | 20220004639 A | 1/2022 |
| KR | 102387577 B1 | 4/2022 |
| KR | 102421437 B1 | 7/2022 |
| KR | 20220102207 A | 7/2022 |
| KR | 102427545 B1 | 8/2022 |
| KR | 102467495 B1 | 11/2022 |
| KR | 102467496 B1 | 11/2022 |
| KR | 102469723 B1 | 11/2022 |
| KR | 102471990 B1 | 11/2022 |
| KR | 20220145989 A | 11/2022 |
| KR | 20220156134 A | 11/2022 |
| KR | 102502744 B1 | 2/2023 |
| KR | 20230019349 A | 2/2023 |
| KR | 20230019350 A | 2/2023 |
| KR | 20230026556 A | 2/2023 |
| KR | 20230026668 A | 2/2023 |
| KR | 20230040526 | 3/2023 |
| KR | 20230050506 A | 4/2023 |
| KR | 20230056118 A | 4/2023 |
| KR | 102528503 B1 | 5/2023 |
| KR | 102531930 B1 | 5/2023 |
| KR | 102532766 B1 | 5/2023 |
| KR | 102539190 B1 | 6/2023 |
| NO | 2012128801 A1 | 9/2012 |
| NO | 2022212921 A1 | 10/2022 |
| RU | 2014131288 A | 2/2016 |
| RU | 2607953 C2 | 1/2017 |
| TW | M474545 U | 3/2014 |
| TW | M638437 U | 3/2023 |
| WO | 0149235 A2 | 7/2001 |
| WO | 0151083 A2 | 7/2001 |
| WO | 2001050387 A1 | 7/2001 |
| WO | 2001056465 A1 | 8/2001 |
| WO | 02062211 A2 | 8/2002 |
| WO | 02093312 A2 | 11/2002 |
| WO | 2003043494 | 5/2003 |
| WO | 2005018453 A1 | 3/2005 |
| WO | 2005074369 A2 | 8/2005 |
| WO | 2006004430 A2 | 1/2006 |
| WO | 2007102709 A1 | 9/2007 |
| WO | 2008114291 A1 | 9/2008 |
| WO | 2008140780 A1 | 11/2008 |
| WO | 2009003170 A1 | 12/2008 |
| WO | 2009008968 A1 | 1/2009 |
| WO | 2011025322 A2 | 3/2011 |
| WO | 2013002568 A2 | 1/2013 |
| WO | 2023164292 A1 | 3/2013 |
| WO | 2013122839 A1 | 8/2013 |
| WO | 2014011447 A1 | 1/2014 |
| WO | 2014163976 A1 | 10/2014 |
| WO | 2015026744 A1 | 2/2015 |
| WO | 2015065298 A1 | 5/2015 |
| WO | 2015082555 A1 | 6/2015 |
| WO | 2016151364 A1 | 9/2016 |
| WO | 2016154318 A1 | 9/2016 |
| WO | 2017030781 A1 | 2/2017 |
| WO | 2017166074 A1 | 5/2017 |
| WO | 2017091691 A1 | 6/2017 |
| WO | 2017165238 A1 | 9/2017 |
| WO | 2018027080 A1 | 2/2018 |
| WO | 2018081795 A1 | 5/2018 |
| WO | 2018171853 A1 | 9/2018 |
| WO | 2019022706 A1 | 1/2019 |
| WO | 2019204876 A1 | 4/2019 |
| WO | 2019143940 A1 | 7/2019 |
| WO | WO-2020014710 A2 * | 1/2020 | ......... A63B 22/0046 |
| WO | 2020185769 A1 | 3/2020 |
| WO | 2020075190 A1 | 4/2020 |
| WO | 2020130979 A1 | 6/2020 |
| WO | 2020149815 A2 | 7/2020 |
| WO | 2020229705 A1 | 11/2020 |
| WO | 2020245727 A1 | 12/2020 |
| WO | 2020249855 A1 | 12/2020 |
| WO | 2020252599 A1 | 12/2020 |
| WO | 2020256577 A1 | 12/2020 |
| WO | 2021021447 A1 | 2/2021 |
| WO | 2021022003 A1 | 2/2021 |
| WO | 2021038980 A1 | 3/2021 |
| WO | 2021055427 A1 | 3/2021 |
| WO | 2021055491 A1 | 3/2021 |
| WO | 2021061061 A1 | 4/2021 |
| WO | 2021081094 A1 | 4/2021 |
| WO | 2021090267 A1 | 5/2021 |
| WO | 2021138620 A1 | 7/2021 |
| WO | 2021216881 A1 | 10/2021 |
| WO | 2021236542 A1 | 11/2021 |
| WO | 2021236961 A1 | 11/2021 |
| WO | 2021262809 A1 | 12/2021 |
| WO | 2022047006 A1 | 3/2022 |
| WO | 2022092493 A1 | 5/2022 |
| WO | 2022092494 A1 | 5/2022 |
| WO | 2022212883 A1 | 10/2022 |
| WO | 2022216498 A1 | 10/2022 |
| WO | 2022251420 A1 | 12/2022 |
| WO | 2023008680 A1 | 2/2023 |
| WO | 2023008681 A1 | 2/2023 |
| WO | 2023022319 A1 | 2/2023 |
| WO | 2023022320 A1 | 2/2023 |
| WO | 2023052695 A1 | 4/2023 |
| WO | 2023091496 A1 | 5/2023 |
| WO | 2023215155 A1 | 11/2023 |
| WO | 2023230075 A1 | 11/2023 |
| WO | 2024013267 A1 | 1/2024 |
| WO | 2024107807 A1 | 5/2024 |

OTHER PUBLICATIONS

Davenport et al., "The Potential for Artificial Intelligence in Health-care", 2019, Future Healthcare Journal 2019, vol. 6, No. 2: Year: 2019, pp. 1-5.

Ahmed et al., "Artificial Intelligence With Multi-Functional Machine Learning Platform Development for Better Healthcare and Precision

(56) References Cited

OTHER PUBLICATIONS

Medicine", 2020, Database (Oxford), 2020:baaa010. doi: 10.1093/database/baaa010 (Year: 2020), pp. 1-35.

Ruiz Ivan et al., "Towards a physical rehabilitation system using a telemedicine approach", Computer Methods in Biomechanics and Biomedical Engineering: Imaging & Visualization, vol. 8, No. 6, Jul. 28, 2020, pp. 671-680, XP055914810.

De Canniere Helene et al., "Wearable Monitoring and Interpretable Machine Learning Can Objectively Track Progression in Patients during Cardiac Rehabilitation", Sensors, vol. 20, No. 12, Jun. 26, 2020, XP055914617, pp. 1-15.

Boulanger Pierre et al., "A Low-cost Virtual Reality Bike for Remote Cardiac Rehabilitation", Dec. 7, 2017, Advances in Biometrics: International Conference, ICB 2007, Seoul, Korea, pp. 155-166.

Yin Chieh et al., "A Virtual Reality-Cycling Training System for Lower Limb Balance Improvement", BioMed Research International, vol. 2016, pp. 1-10.

International Search Report and Written Opinion for International Application No. PCT/US2021/032807, Date of Mailing Sep. 6, 2021, 11 pages.

International Search Report and Written Opinion for PCT/US2023/014137, dated Jun. 9, 2023, 13 pages.

Website for "Esino 2022 Physical Therapy Equipments Arm Fitness Indoor Trainer Leg Spin Cycle Machine Exercise Bike for Elderly," https://www.made-in-china.com/showroom/esinogroup/product-detailYdZlwGhCMKVR/China-Esino-2022-Physical-Therapy-Equipments-Arm-Fitness-Indoor-Trainer-Leg-Spin-Cycle-Machine-Exercise-Bike-for-Elderly.html, retrieved on Aug. 29, 2023, 5 pages.

Abedtash, "An Interoperable Electronic Medical Record-Based Platform for Personalized Predictive Analytics", ProQuest LLC, Jul. 2017, 185 pages.

Malloy, Online Article "AI-enabled EKGs find difference between numerical age and biological age significantly affects health, longevity", Website: https://newsnetwork.mayoclinic.org/discussion/ai-enabled-ekgs-find-difference-between-numerical-age-and-biological-age-significantly-affects-health-longevity/, Mayo Clinic News Network, May 20, 2021, retrieved: Jan. 23, 2023, p. 1-4.

Chrif et al., "Control design for a lower-limb paediatric therapy device using linear motor technology," Article, 2017, pp. 119-127, Science Direct, Switzerland.

Robben et al., "Delta Features From Ambient Sensor Data are Good Predictors of Change in Functional Health," Article, 2016, pp. 2168-2194, vol. 21, No. 4, IEEE Journal of Biomedical and Health Informatics.

Kantoch et al., "Recognition of Sedentary Behavior by Machine Learning Analysis of Wearable Sensors during Activities of Daily Living for Telemedical Assessment of Cardiovascular Risk," Article, 2018, 17 pages, Sensors, Poland.

Warburton et al., "International Launch of the PAR-•Q+ and ePARmed-•X+ Validation of the PAR-•Q+ and ePARmed••X+," Health & Fitness Journal of Canada, 2011, 9 pages, vol. 4, No. 2.

Jeong et al., "Computer-assisted upper extremity training using interactive biking exercise (iBikE) platform," Sep. 2012, pp. 1-5, 34th Annual International Conference of the IEEE EMBS.

Jennifer Bresnick, "What is the Role of Natural Language Processing in Healthcare?", pp. 1-7, published Aug. 18, 2016, retrieved on Feb. 1, 2022 from https://healthitanalytics.com/ featu res/what-is-the-role-of-natural-language-processing-in-healthcare.

Alex Bellec, "Part-of-Speech tagging tutorial with the Keras Deep Learning library," pp. 1-16, published Mar. 27, 2018, retrieved on Feb. 1, 2022 from https://becominghuman.ai/part-of-speech-tagging-tutorial-with-the-keras-deep-learning-library-d7f93fa05537.

Kavita Ganesan, All you need to know about text preprocessing for NLP and Machine Learning, pp. 1-14, published Feb. 23, 2019, retrieved on Feb. 1, 2022 from https:// towardsdatascience.com/all-you-need-to-know-about-text-preprocessing-for-nlp-and-machine-learning-bcl c5765ff67.

Badreesh Shetty, "Natural Language Processing (NPL) for Machine Learning," pp. 1-13, published Nov. 24, 2018, retrieved on Feb. 1, 2022 from https://towardsdatascience. com/natural-language-processing-nlp-for-machine-learning-d44498845d5b.

Gerbild et al., "Physical Activity to Improve Erectile Dysfunction: A Systematic Review of Intervention Studies," Sexual Medicine, 2018, 15 pages.

Website for "Pedal Exerciser", p. 1, retrieved on Sep. 9, 2022 from https://www.vivehealth.com/collections/physical-therapy-equipment/products/pedalexerciser.

Website for "Functional Knee Brace with ROM", p. 1, retrieved on Sep. 9, 2022 from http://medicalbrace.gr/en/product/functional-knee-brace-with-goniometer-mbtelescopicknee/.

Website for "ComfySplints Goniometer Knee", pp. 1-5, retrieved on Sep. 9, 2022 from https://www.comfysplints.com/product/knee-splints/.

Website for "BMI FlexEze Knee Corrective Orthosis (KCO)", pp. 1-4, retrieved on Sep. 9, 2022 from https://orthobmi.com/products/bmi-flexeze%C2%AE-knee-corrective-orthosis-kco.

Website for "Neoprene Knee Brace with goniometer—Patella Rom MB.4070", pp. 1-4, retrieved on Sep. 9, 2022 from https://www.fortuna.com.gr/en/product/neoprene-knee-brace-with-goniometer-patella-rom-mb-4070/.

Kuiken et al., "Computerized Biofeedback Knee Goniometer: Acceptance and Effect on Exercise Behavior in Post-total Knee Arthroplasty Rehabilitation," Biomedical Engineering Faculty Research and Publications, 2004, pp. 1-10.

Ahmed et al., "Artificial intelligence with multi-functional machine learning platform development for better healthcare and precision medicine," Database, 2020, pp. 1-35.

Davenport et al., "The potential for artificial intelligence in healthcare," Digital Technology, Future Healthcare Journal, 2019, pp. 1-5, vol. 6, No. 2.

Website for "OxeFit XS1", pp. 1-3, retrieved on Sep. 9, 2022 from https://www.oxefit.com/xs1.

Website for "Preva Mobile", pp. 1-6, retrieved on Sep. 9, 2022 from https://www.precor.com/en-us/resources/introducing-preva-mobile.

Website for "J-Bike", pp. 1-3, retrieved on Sep. 9, 2022 from https://www.magneticdays.com/en/cycling-for-physical-rehabilitation.

Website for "Excy", pp. 1-12, retrieved on Sep. 9, 2022 from https://excy.com/portable-exercise-rehabilitation-excy-xcs-pro/.

Website for "OxeFit XP1", p. 1, retrieved on Sep. 9, 2022 from https://www.oxefit.com/xp1.

Barrett et al., "Artificial intelligence supported patient self-care in chronic heart failure: a paradigm shift from reactive to predictive, preventive and personalised care," EPMA Journal (2019), pp. 445-464.

Oerkild et al., "Home-based cardiac rehabilitation is an attractive alternative to no cardiac rehabilitation for elderly patients with coronary heart disease: results from a randomised clinical trial," BMJ Open Accessible Medical Research, Nov. 22, 2012, pp. 1-9.

Bravo-Escobar et al., "Effectiveness and safety of a home-based cardiac rehabilitation programme of mixed surveillance in patients with ischemic heart disease at moderate cardiovascular risk: A randomised, controlled clinical trial," BMC Cardiovascular Disorders, 2017, pp. 1-11, vol. 17:66.

Thomas et al., "Home-Based Cardiac Rehabilitation," Circulation, 2019, pp. e69-e89, vol. 140.

Thomas et al., "Home-Based Cardiac Rehabilitation," Journal of the American College of Cardiology, Nov. 1, 2019, pp. 133-153, vol. 74.

Thomas et al., "Home-Based Cardiac Rehabilitation," HHS Public Access, Oct. 2, 2020, pp. 1-39.

Dittus et al., "Exercise-Based Oncology Rehabilitation: Leveraging the Cardiac Rehabilitation Model," Journal of Cardiopulmonary Rehabilitation and Prevention, 2015, pp. 130-139, vol. 35.

Chen et al., "Home-based cardiac rehabilitation improves quality of life, aerobic capacity, and readmission rates in patients with chronic heart failure," Medicine, 2018, pp. 1-5 Vol. 97:4.

Lima de Melo Ghisi et al., "A systematic review of patient education in cardiac patients: Do they increase knowledge and promote health behavior change?," Patient Education and Counseling, 2014, pp. 1-15.

(56) References Cited

OTHER PUBLICATIONS

Fang et al., "Use of Outpatient Cardiac Rehabilitation Among Heart Attack Survivors—20 States and the District of Columbia, 2013 and Four States, 2015," Morbidity and Mortality Weekly Report, vol. 66, No. 33, Aug. 25, 2017, pp. 869-873.

Beene et al., "AI and Care Delivery: Emerging Opportunities for Artificial Intelligence to Transform How Care Is Delivered," Nov. 2019, American Hospital Association, pp. 1-12.

Jeong et al., "Remotely controlled biking is associated with improved adherence to prescribed cycling speed," Technology and Health Care 23, 2015, 7 pages.

Laustsen et al., "Telemonitored exercise-based cardiac rehabilitation improves physical capacity and health-related quality of life," Journal of Telemedicine and Telecare, 2020, DOI: 10.1177/1357633X18792808, 9 pages.

Blasiak et al., "CURATE.AI: Optimizing Personalized Medicine with Artificial Intelligence,"SLAS TECHNOLOGY: Translating Life Sciences Innovation, 2020, 11 pages.

Alcaraz et al., "Machine Learning as Digital Therapy Assessment for Mobile Gait Rehabilitation," 2018 IEEE 28th International Workshop on Machine Learning for Signal Processing (MLSP), Aalborg, Denmark, 2018, 6 pages.

Androutsou et al., "A Smartphone Application Designed to Engage the Elderly in Home-Based Rehabilitation," Frontiers in Digital Health, Sep. 2020, vol. 2, Article 15, 13 pages.

Silva et al., "SapoFitness: A mobile health application for dietary evaluation," 2011 IEEE 13th International Conference on U e-Health Networking, Applications and Services, Columbia, MO, USA, 2011, 6 pages.

Wang et al., "Interactive wearable systems for upper body rehabilitation: a systematic review," Journal of NeuroEngineering and Rehabilitation, 2017, 21 pages.

Marzolini et al., "Eligibility, Enrollment, and Completion of Exercise-Based Cardiac Rehabilitation Following Stroke Rehabilitation: What Are the Barriers?," Physical Therapy, vol. 100, No. 1, 2019, 13 pages.

Nijjar et al., "Randomized Trial of Mindfulness-Based Stress Reduction in Cardiac Patients Eligible for Cardiac Rehabilitation," Scientific Reports, 2019, 12 pages.

Lara et al., "Human-Robot Sensor Interface for Cardiac Rehabilitation," IEEE International Conference on Rehabilitation Robotics, Jul. 2017, 8 pages.

Ishraque et al., "Artificial Intelligence-Based Rehabilitation Therapy Exercise Recommendation System," 2018 IEEE Mit Undergraduate Research Technology Conference (URTC), Cambridge, Ma, USA, 2018, 5 pages.

Zakari et al., "Are There Limitations to Exercise Benefits in Peripheral Arterial Disease?," Frontiers in Cardiovascular Medicine, Nov. 2018, vol. 5, Article 173, 12 pages.

You et al., "Including Blood Vasculature into a Game-Theoretic Model of Cancer Dynamics," Games 2019, 10, 13, 22 pages.

Jeong et al., "Computer-assisted upper extremity training using interactive biking exercise (iBikE) platform," Sep. 2012, 34th Annual International Conference of the IEEE Embs, 5 pages.

Ahmed et al., "Artificial Intelligence With Multi-Functional Machine Learning Platform Development for Better Healthcare and Precision Medicine," Database (Oxford), 2020, pp. 1-35, vol. 2020.

Davenport et al., "The Potential for Artificial Intelligence in Healthcare," Future Healthcare Journal, 2019, pp. 94-98, vol. 6, No. 2.

Marios et al., "The effect of tele-monitoring on exercise training adherence, functional capacity, quality of life and glycemic control in patients with type II diabetes," Journal of Sports Science and Medicine, Mar. 2012, vol. 11, 6 pages.

Abidi, Samina; A Knowledge-Modeling Approach to Integrate Multiple Clinical Practice Guidelines to Provide Evidence-Based Clinical Decision Support for Managing Comorbid Conditions; Journal of Medical Systems 41.12: 1-19. Springer Nature B.V. (Dec 2017) (Year: 2017).

Fuller, Carole G.; Diagnosis and treatment considerations with comorbid developmentally disabled populations; Journal of Clinical Psychology 54.1: 1-10. John Wiley and Sons Inc. (Jan 1998) (Year: 1998).

He, Jianxing et al. The practical implementation of artificial intelligence technologies in medicine. Nature Medicine; New York vol. 25, Iss. 1. Jan 2019. (Year: 2019).

cG. Acampora, D. J. Cook, P. Rashidi and A. V. Vasilakos, "A Survey on Ambient Intelligence in Healthcare," in Proceedings of the IEEE, vol. 101, No. 12, pp. 2470-2494, Dec. 2013, doi: 10.1109/JPROC20132262913. (Year: 2013).

H. Demirkan, "A Smart Healthcare Systems Framework," in IT Professional, vol. 15, No. 5, pp. 38-45, Sep.-Oct. 2013, doi: 10.1109/MITP.2013.35. (Year: 2013).

W. Rashwan, J. Fowler and A. Arisha, "A Multi-Method Scheduling Framework for Medical Staff," 2018 Winter Simulation Conference (WSC), Gothenburg, Sweden, 2018, pp. 1464-1475, doi: 10.1109/WSC.2018.8632247. (Year: 2018).

Fraass et al, "The impact of treatment complexity and computer-control delivery technology on treatment delivery errors," pp. 651-659, Oct. 1, 1998, International Journal of Radiation Oncology Biology Physics, vol. 42, Issue 3, https://doi.org/:10.1016/s0360-3016(98)00244-2. PMID: 9806527.

Marchal-Crespo et al, "Review of control strategies for robotic movement training after neurologic injury," pp. 1-15, Jun. 16, 2009, Journal of NeuroEngineering and Rehabilitation, vol. 6, No. 20, https://doi. org/10.1186/1743-0003-6-20.

Chrif et al, "Control design for a lower-limb paediatric therapy device using linear motor technology," pp. 119-127, Jun. 9, 2017, Biomedical Usignal Processing and Control, vol. 38, https://www.sciencedirect.com/science/article/pii/S1746809417301027.

International Preliminary Report on Patentability of International Application No. PCT/2024/022550, Date of Mailing Sep. 20, 2025, 7 pages.

Shen et al, "Intelligent inverse treatment planning via deep reinforcement learning, a proof-of-principle study in high dose-rate brachytherapy for cervical cancer," pp. 1-17, May 29, 2019, Phys. Med. Biol. Vol. 64, No. 115013.

Karboub et al, "A Machine Learning Based Discharge Prediction of Cardiovascular Diseases Patients in Intensive 6 Care Units.," pp. 1-23, May 24, 2022, Healthcare (Basel, Switzerland) MDPI, vol. 10(6), No. 966, https://doi.org/10.3390/healthcare10060966.

* cited by examiner

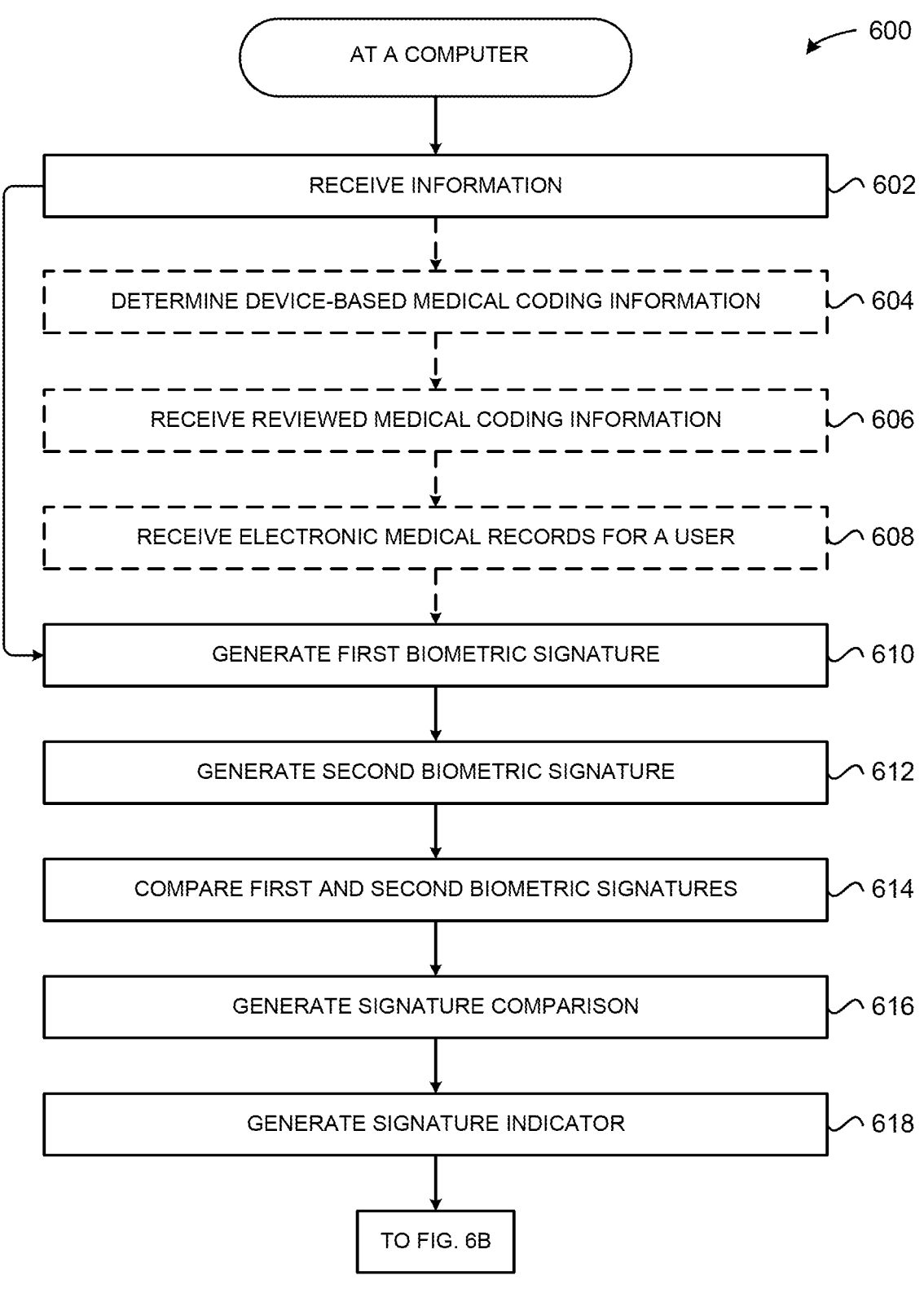

— 600

AT A COMPUTER

RECEIVE INFORMATION     602

DETERMINE DEVICE-BASED MEDICAL CODING INFORMATION     604

RECEIVE REVIEWED MEDICAL CODING INFORMATION     606

RECEIVE ELECTRONIC MEDICAL RECORDS FOR A USER     608

GENERATE FIRST BIOMETRIC SIGNATURE     610

GENERATE SECOND BIOMETRIC SIGNATURE     612

COMPARE FIRST AND SECOND BIOMETRIC SIGNATURES     614

GENERATE SIGNATURE COMPARISON     616

GENERATE SIGNATURE INDICATOR     618

SYSTEM AND METHOD FOR PROCESSING MEDICAL CLAIMS USING BIOMETRIC SIGNATURES

CROSS-REFERENCES TO RELATED APPLICATIONS

This application is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes. This application also claims priority to and the benefit of U.S. Provisional Patent Application Ser. No. 63/028,420, filed May 21, 2020, titled "System and Method for Processing Medical Claims Using Biometric Signatures," the entire disclosure of which is hereby incorporated by reference for all purposes.

TECHNICAL FIELD

This disclosure relates generally to systems and methods for processing medical claims using biometric signatures.

BACKGROUND

Electronic medical record (EMR) systems may be used to generate and maintain an electronic record of health-related information relating to or about individuals within a health care organization. The health-related information may be input by a variety of entities, e.g., the individuals' health care providers, where such entries may be made by any medically-related entity or its representatives, for example: administrators, nurses, doctors, or other authorized individuals; insurance companies; billing companies; hospitals; testing centers, such as those related to radiologic services, blood and bodily fluid testing services; and psychological service providers, such as psychologists, social workers, addiction and other counselors, and psychiatrists. Each healthcare service may have one or more medical billing codes, for example, Diagnosis-Related Group (DRG) and/or International Classification of Diseases (ICD) codes, e.g., ICD-10, assigned for billing purposes. Some of the individual's EMRs, including the one or more medical billing codes, may be transferred to a third-party payor, such as an insurance company, for invoicing the individual's medical claims for the individual's healthcare services. A medical claim, or a claim, is a medical bill, or bill, submitted to a health insurance carrier, or other party responsible for payment, for services rendered and/or goods provided to patients by health care providers. After a medical claim is submitted to the insurance company, the insurance company determines its financial responsibility for the payment to the healthcare provider (i.e., claim adjudication). The insurance company may have procedures to ensure that no false medical claims are approved for payment, for example, by rejecting payment for medical billing codes inconsistent with the healthcare services provided. As a result of such procedures, the insurance company may decide to pay the medical claim in full, reduce the medical bill, deny the full medical claim, or revise the nature of the claim such that it becomes eligible for full or partial payment.

Medical billing may present difficulties in claim adjudication when using medical billing codes, often making it difficult for insurance companies to detect whether a particular medical claim is the result of fraud, waste, or abuse. Even if an insurance company has the ability to determine that a medical device has been used, the insurance company may have difficulty in determining whether the use of that medical device was properly billed (e.g., the medical device was not used by or for the patient stated in the medical claim). The use of telemedicine may result in additional risks related to fraud, waste, and abuse, risks which bad actors can exploit. For example, if, at a location other than a healthcare facility, the medical device is being used, a healthcare provider may not oversee the use (e.g., treatment, rehabilitation, or testing), and therefore, the healthcare provider may not be able to easily confirm or validate the accuracy of the medical billing.

SUMMARY

In general, the present disclosure provides a system and method for processing medical claims using biometric signatures.

An aspect of the disclosed embodiments includes a computer-implemented system for processing medical claims. The computer-implemented system includes a medical device configured to be manipulated by a user while the user performs a treatment plan; a patient interface associated with the medical device, the patient interface comprising an output configured to present telemedicine information associated with a telemedicine session; and a processor. The processor is configured to, during the telemedicine session, receive device-generated information from the medical device; generate a first biometric signature; using the device-generated information, generate a second biometric signature; using the first and second biometric signatures, generate a signature comparison; using the signature comparison, generate a signature indicator; and transmit the signature indicator.

An aspect of the disclosed embodiments includes a system for processing medical claims. The system includes a processor configured to receive device-generated information from a medical device; to generate a first biometric signature; to use the device-generated information to generate a second biometric signature; to use the first biometric signature and the second biometric signature to generate a signature comparison; to use the signature comparison to generate a signature indicator; and to transmit the signature indicator.

An aspect of the disclosed embodiments includes a method for processing medical claims. The method includes receiving device-generated information from a medical device. The method further includes generating a first biometric signature; using the device-generated information to generate a second biometric signature; using the first biometric signature and the second biometric signature to generate a signature comparison; using the signature comparison to generate a signature indicator; and transmitting the signature indicator.

An aspect of the disclosed embodiments includes a tangible, non-transitory computer-readable storage medium. The tangible, non-transitory computer-readable storage medium stores instructions that, when executed, cause a processor to receive device-generated information from a medical device. The instructions further cause a processor to generate a first biometric signature; to use the device-generated information to generate a second biometric signature; to use the first biometric signature and the second biometric signature to generate a signature comparison; to use the signature comparison to generate a signature indicator; and to cause the processor to transmit the signature indicator.

Another aspect of the disclosed embodiments includes a system that includes a processing device and a memory communicatively coupled to the processing device and capable of storing instructions. The processing device executes the instructions to perform any of the methods, operations, or steps described herein.

Another aspect of the disclosed embodiments includes a tangible, non-transitory computer-readable medium storing instructions that, when executed, cause a processing device to perform any of the methods, operations, or steps disclosed herein.

Other technical features may be readily apparent to one skilled in the art from the following figures, descriptions, and claims.

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

FIGS. 6A and 6B generally illustrate a method of processing medical claims according to the principles of this disclosure.

NOTATION AND NOMENCLATURE

Figure 1:
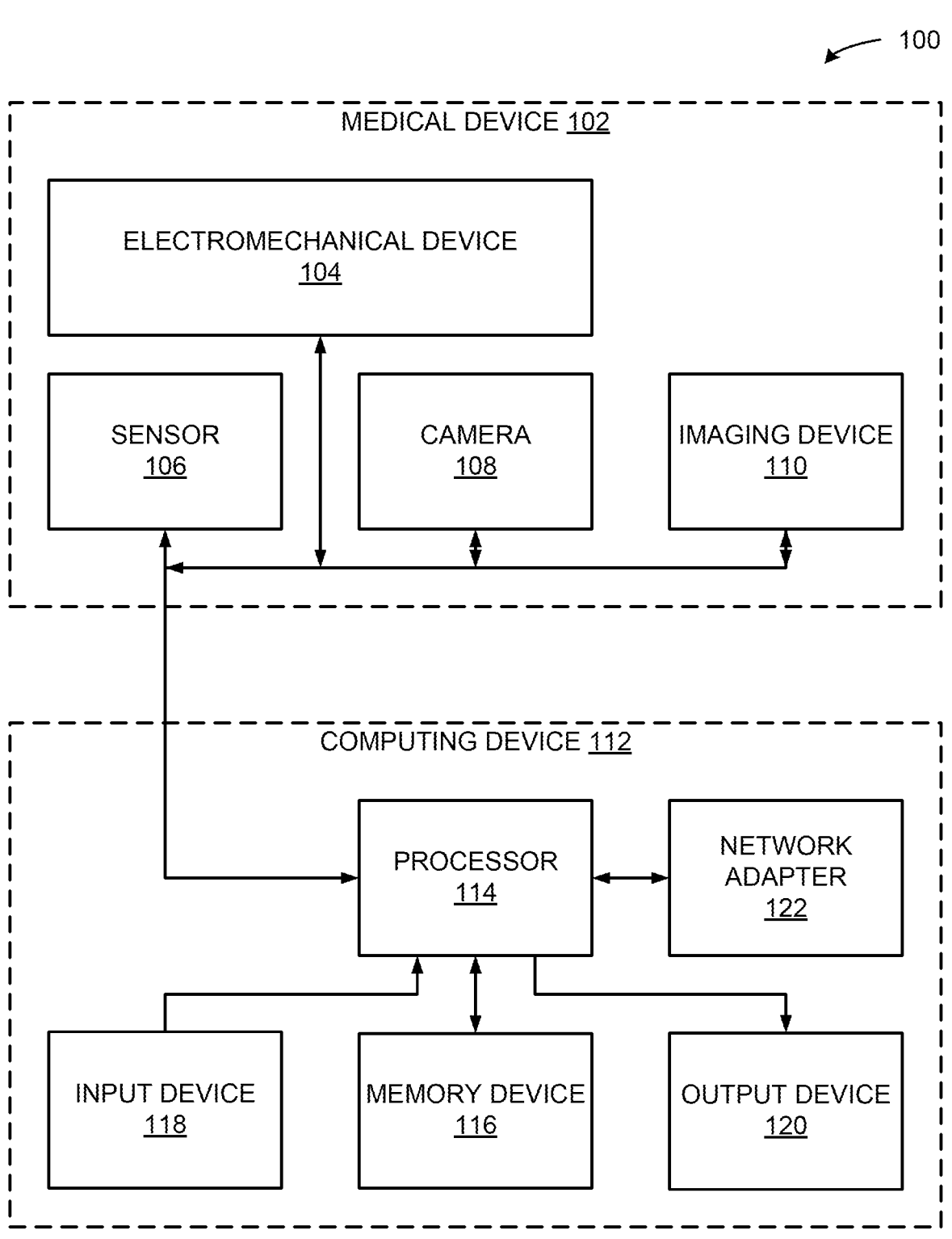
FIG. 1 generally illustrates a component diagram of an illustrative medical system according to the principles of this disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple"

or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

The terms telemedicine, telehealth, telemed, teletherapeutic, telemedicine, remote medicine, etc. may be used interchangeably herein.

The term "optimal treatment plan" may refer to optimizing a treatment plan based on a certain parameter or factors or combinations of more than one parameter or factor, such as, but not limited to, a measure of benefit which one or more exercise regimens provide to users, one or more probabilities of users complying with one or more exercise regimens, an amount, quality or other measure of sleep associated with the user, information pertaining to a diet of the user, information pertaining to an eating schedule of the user, information pertaining to an age of the user, information pertaining to a sex of the user, information pertaining to a gender of the user, an indication of a mental state of the user, information pertaining to a genetic condition of the user, information pertaining to a disease state of the user, an indication of an energy level of the user, information pertaining to a microbiome from one or more locations on or in the user (e.g., skin, scalp, digestive tract, vascular system, etc.), or some combination thereof.

As used herein, the term healthcare provider may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare provider" may be a human being, a robot, a virtual assistant, a virtual assistant in virtual and/or augmented reality, or an artificially intelligent entity, such entity including a software program, integrated software and hardware, or hardware alone.

Real-time may refer to less than or equal to 2 seconds. Near real-time may refer to any interaction of a sufficiently short time to enable two individuals to engage in a dialogue via such user interface, and will preferably but not determinatively be less than 10 seconds (or any suitably proximate difference between two different times) but greater than 2 seconds.

Any of the systems and methods described in this disclosure may be used in connection with rehabilitation. Rehabilitation may be directed at cardiac rehabilitation, rehabilitation from stroke, multiple sclerosis, Parkinson's disease, myasthenia gravis, Alzheimer's disease, any other neurodegenative or neuromuscular disease, a brain injury, a spinal cord injury, a spinal cord disease, a joint injury, a joint disease, post-surgical recovery, or the like. Rehabilitation can further involve muscular contraction in order to improve blood flow and lymphatic flow, engage the brain and nervous system to control and affect a traumatized area to increase the speed of healing, reverse or reduce pain (including arthralgias and myalgias), reverse or reduce stiffness, recover range of motion, encourage cardiovascular engagement to stimulate the release of pain-blocking hormones or to encourage highly oxygenated blood flow to aid in an overall feeling of well-being. Rehabilitation may be provided for individuals of average weight in reasonably good physical condition having no substantial deformities, as well as for individuals more typically in need of rehabilitation, such as those who are elderly, obese, subject to disease processes, injured and/or who have a severely limited range of motion. Unless expressly stated otherwise, is to be understood that rehabilitation includes prehabilitation (also referred to as "pre-habilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through, dissecting and/or harming numerous muscles and muscle groups in or about, without limitation, the skull or face, the abdomen, the ribs and/or the thoracic cavity, as well as in or about all joints and appendages. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. Performance of the one or more sets of exercises may be required in order to qualify for an elective surgery, such as a knee replacement. The patient may prepare an area of his or her body for the surgical procedure by performing the one or more sets of exercises, thereby strengthening muscle groups, improving existing muscle memory, reducing pain, reducing stiffness, establishing new muscle memory, enhancing mobility (i.e., improve range of motion), improving blood flow, and/or the like.

The phrase, and all permutations of the phrase, "respective measure of benefit with which one or more exercise regimens may provide the user" (e.g., "measure of benefit," "respective measures of benefit," "measures of benefit," "measure of exercise regimen benefit," "exercise regimen benefit measurement," etc.) may refer to one or more measures of benefit with which one or more exercise regimens may provide the user.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Determining optimal remote examination procedures to create an optimal treatment plan for a patient having certain characteristics (e.g., vital-sign or other measurements; performance; demographic; psychographic; geographic; diagnostic; measurement- or test-based; medically historic; behavioral historic; cognitive; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment device, an amount of force exerted on a portion of the treatment device, a range of motion achieved on the treatment device, a movement speed of a portion of the treatment device, a duration of use of the treatment device, an indication of a plurality of pain levels using the treatment device, or some combination thereof. The measurement information may include, e.g., a vital sign, a respiration rate, a heartrate, a temperature, a blood pressure, a glucose level or other biomarker, or some combination thereof. It may be desirable to process and analyze the characteristics of a multitude of patients, the treatment plans performed for those patients, and the results of the treatment plans for those patients.

Further, another technical problem may involve distally treating, via a computing device during a telemedicine session, a patient from a location different than a location at which the patient is located. An additional technical problem is controlling or enabling, from the different location, the control of a treatment device used by the patient at the patient's location. Oftentimes, when a patient undergoes rehabilitative surgery (e.g., knee surgery), a medical professional may prescribe a treatment device to the patient to use to perform a treatment protocol at their residence or at any mobile location or temporary domicile. A medical professional may refer to a doctor, physician assistant, nurse, chiropractor, dentist, physical therapist, acupuncturist, physical trainer, or the like. A medical professional may refer to any person with a credential, license, degree, or the like in the field of medicine, physical therapy, rehabilitation, or the like.

When the healthcare provider is located in a location different from the patient and the treatment device, it may be technically challenging for the healthcare provider to monitor the patient's actual progress (as opposed to relying on the patient's word about their progress) in using the treatment device, modify the treatment plan according to the patient's progress, adapt the treatment device to the personal characteristics of the patient as the patient performs the treatment plan, and the like.

Further, in addition to the information described above, determining optimal examination procedures for a particular ailment (e.g., injury, disease, any applicable medical condition, etc.) may include physically examining the injured body part of a patient. The healthcare provider, such as a physician or a physical therapist, may visually inspect the injured body part (e.g., a knee joint). The inspection may include looking for signs of inflammation or injury (e.g., swelling, redness, and warmth), deformity (e.g., symmetrical joints and abnormal contours and/or appearance), or any other suitable observation. To determine limitations of the injured body part, the healthcare provider may observe the injured body part as the patient attempts to perform normal activity (e.g., bending and extending the knee and gauging any limitations to the range of motion of the injured knee). The healthcare provide may use one or more hands and/or fingers to touch the injured body part. By applying pressure to the injured body part, the healthcare provider can obtain information pertaining to the extent of the injury. For example, the healthcare provider's fingers may palpate the injured body part to determine if there is point tenderness, warmth, weakness, strength, or to make any other suitable observation.

It may be desirable to compare characteristics of the injured body part with characteristics of a corresponding non-injured body part to determine what an optimal treatment plan for the patient may be such that the patient can obtain a desired result. Thus, the healthcare provider may examine a corresponding non-injured body part of the patient. For example, the healthcare provider's fingers may palpate a non-injured body part (e.g., a left knee) to determine a baseline of how the patient's non-injured body part feels and functions. The healthcare provider may use the results of the examination of the non-injured body part to determine the extent of the injury to the corresponding injured body part (e.g., a right knee). Additionally, injured body parts may affect other body parts (e.g., a knee injury may limit the use of the affected leg, leading to atrophy of leg muscles). Thus, the healthcare provider may also examine additional body parts of the patient for evidence of atrophy of or injury to surrounding ligaments, tendons, bones, and muscles, examples of muscles being such as quadriceps, hamstrings, or calf muscle groups of the leg with the knee injury. The healthcare provider may also obtain information as to a pain level of the patient before, during, and/or after the examination.

The healthcare provider can use the information obtained from the examination (e.g., the results of the examination) to determine a proper treatment plan for the patient. If the healthcare provider cannot conduct a physical examination of the one or more body parts of the patient, the healthcare provider may not be able to fully assess the patient's injury and the treatment plan may not be optimal. Accordingly, embodiments of the present disclosure pertain to systems and methods for conducting a remote examination of a patient. The remote examination system provides the healthcare provider with the ability to conduct a remote examination of the patient, not only by communicating with the patient, but by virtually observing and/or feeling the patient's one or more body parts.

In some embodiments, the systems and methods described herein may be configured for manipulation of a medical device. For example, the systems and methods may be configured to use a medical device configured to be manipulated by an individual while the individual is performing a treatment plan. The individual may include a user, patient, or other a person using the treatment device to perform various exercises for prehabilitation, rehabilitation, stretch training, e.g., pliability, medical procedures, and the like. The systems and methods described herein may be configured to use and/or provide a patient interface comprising an output device, wherein the output device is configured to present telemedicine information associated with a telemedicine session.

In some embodiments, the systems and methods described herein may be configured for processing medical claims. For example, the system includes a processor configured to receive device-generated information from a medical device. Using the device-generated information received, the processor is configured to determine device-based medical coding information. The processor is further configured to transmit the device-based medical coding information to a claim adjudication server. Any or all of the methods described may be implemented during a telemedicine session or at any other desired time.

In some embodiments, the medical claims may be processed, during a telemedicine or telehealth session, by a healthcare provider. The healthcare provider may select a particular treatment plan for the patient to cause that treatment plan to be transmitted to the patient and/or to control, based on the treatment plan, the treatment device. In some embodiments, to facilitate telehealth or telemedicine applications, including remote diagnoses, determination of treatment plans and rehabilitative and/or pharmacologic prescriptions, the artificial intelligence engine may receive data, instructions, or the like and/or operate distally from the patient and the treatment device.

In such cases, the recommended treatment plans and/or excluded treatment plans may be presented simultaneously with a video of the patient in real-time or near real-time during a telemedicine or telehealth session on a user interface of a computing device of a medical professional. The video may also be accompanied by audio, text and other multimedia information and/or other sensorial or perceptive (e.g., tactile, gustatory, haptic, pressure-sensing-based or electromagnetic (e.g., neurostimulation), and without limitation, gesture recognition, gesture control, touchless user interfaces (TUIs), kinetic user interfaces (KUIs), tangible user interfaces, wired gloves, depth-aware cameras, stereo cameras, and gesture-based controllers). Real-time may refer to less than or equal to 2 seconds. Near real-time may refer to any interaction of a sufficiently short time to enable two individuals to engage in a dialogue via such user interface, and will generally be less than 10 seconds (or any suitably proximate difference between two different times) but greater than 2 seconds.

FIGS. 1-10, discussed below, and the various embodiments used to describe the principles of this disclosure are by way of illustration only and should not be construed in any way to limit the scope of the disclosure.

Figure 2:
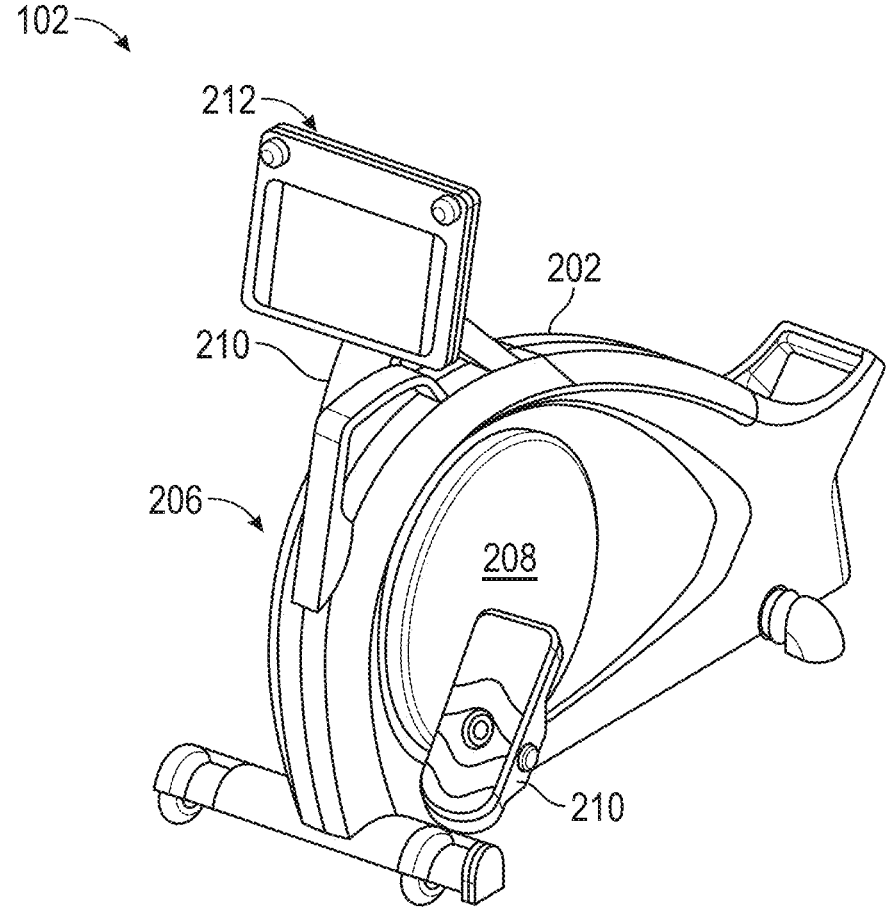
FIG. 2 generally illustrates an example medical device according to the principles of this disclosure.

FIG. 1 illustrates a component diagram of an illustrative medical system 100 in accordance with aspects of this disclosure. The medical system 100 may include a medical device 102. The medical device 102 may be a testing device, a diagnostic device, a therapeutic device, or any other suitable medical device. "Medical device" as used in this context means any hardware, software, mechanical, such as a treatment device (e.g., medical device 102, treatment device 10, or the like), that may assist in a medical service, regardless of whether it is FDA (or other governmental regulatory body of any given country) approved, required to be FDA (or other governmental regulatory body of any given country) approved or available commercially or to consumers without such approval. Non-limiting examples of medical devices include a thermometer, an MRI machine, a CT-scan machine, a glucose meter, an apheresis machine, and a physical therapy machine, such as a physical therapy cycle. Non-limiting examples of places where the medical device 102 may be located include a healthcare clinic, a physical rehabilitation center, and a user's home to allow for telemedicine treatment, rehabilitation, and/or testing. FIG. 2 illustrates an example of the medical device 102 where the medical device 102 is a physical therapy cycle.

As generally illustrated in FIG. 2, the medical device 102 may comprise an electromechanical device, such as a physical therapy device. FIG. 2 generally illustrates a perspective view of an example of a medical device 102 according to certain aspects of this disclosure. Specifically, the medical device 102 illustrated is an electromechanical device 202, such as an exercise and rehabilitation device (e.g., a physical therapy device or the like). The electromechanical device 202 is shown having pedal 210 on opposite sides that are adjustably positionable relative to one another on respective radially-adjustable couplings 208. The depicted electromechanical device 202 is configured as a small and portable unit so that it is easily transported to different locations at which rehabilitation or treatment is to be provided, such as at patients' homes, alternative care facilities, or the like. The patient may sit in a chair proximate the electromechanical device 202 to engage the electromechanical device 202 with the patient's feet, for example. The electromechanical device 202 includes a rotary device such as radially-adjustable couplings 208 or flywheel or the like rotatably mounted such as by a central hub to a frame or other support. The pedals 210 are configured for interacting with a patient to be rehabilitated and may be configured for use with lower body extremities such as the feet, legs, or upper body extremities, such as the hands, arms, and the like. For example, the pedal 210 may be a bicycle pedal of the type having a foot support rotatably mounted onto an axle with bearings. The axle may or may not have exposed end threads for engaging a mount on the radially-adjustable coupling 208 to locate the pedal on the radially-adjustable coupling 208. The radially-adjustable coupling 208 may include an actuator configured to radially adjust the location of the pedal to various positions on the radially-adjustable coupling 208.

Alternatively, the radially-adjustable coupling 208 may be configured to have both pedals 210 on opposite sides of a single coupling 208. In some embodiments, as depicted, a pair of radially-adjustable couplings 208 may be spaced apart from one another but interconnected to an electric motor 206. In the depicted example, the computing device 112 may be mounted on the frame of the electromechanical device 202 and may be detachable and held by the user while the user operates the electromechanical device 202. The computing device 112 may present the patient portal 212 and control the operation of the electric motor 206, as described herein.

In some embodiments, as described in U.S. Pat. No. 10,173,094 (U.S. application Ser. No. 15/700,293), which is incorporated by reference herein in its entirety for all purposes, the medical device 102 may take the form of a traditional exercise/rehabilitation device which is more or less non-portable and remains in a fixed location, such as a rehabilitation clinic or medical practice. The medical device 102 may include a seat and is less portable than the medical device 102 shown in FIG. 2. FIG. 2 is not intended to be limiting; the electromechanical device 202 may include more or fewer components than those illustrated in FIG. 2.

Figure 7:
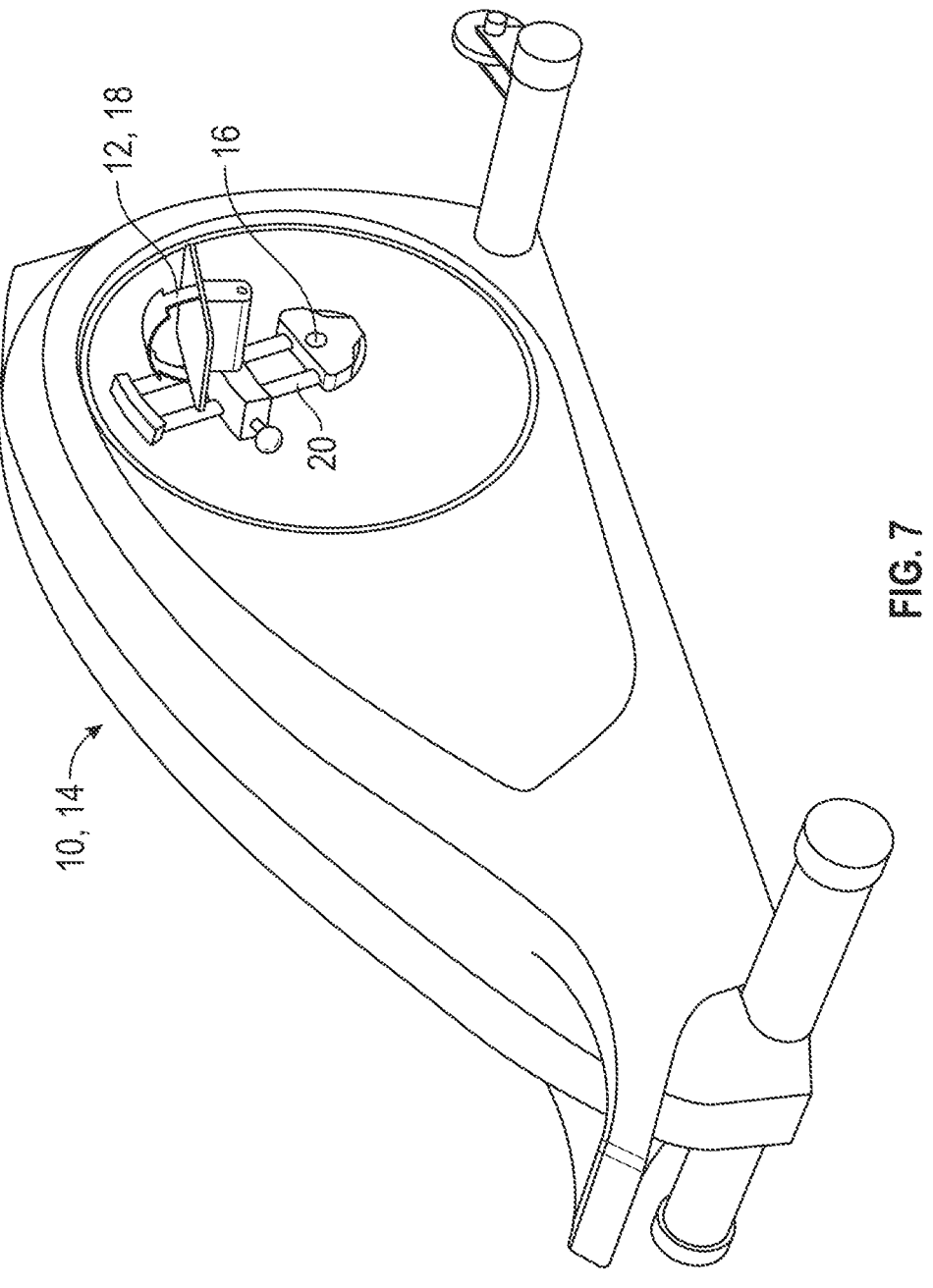
FIG. 7 generally illustrates a perspective view of an embodiment of the device, such as a treatment device according to certain aspects of this disclosure.
Figure 8:
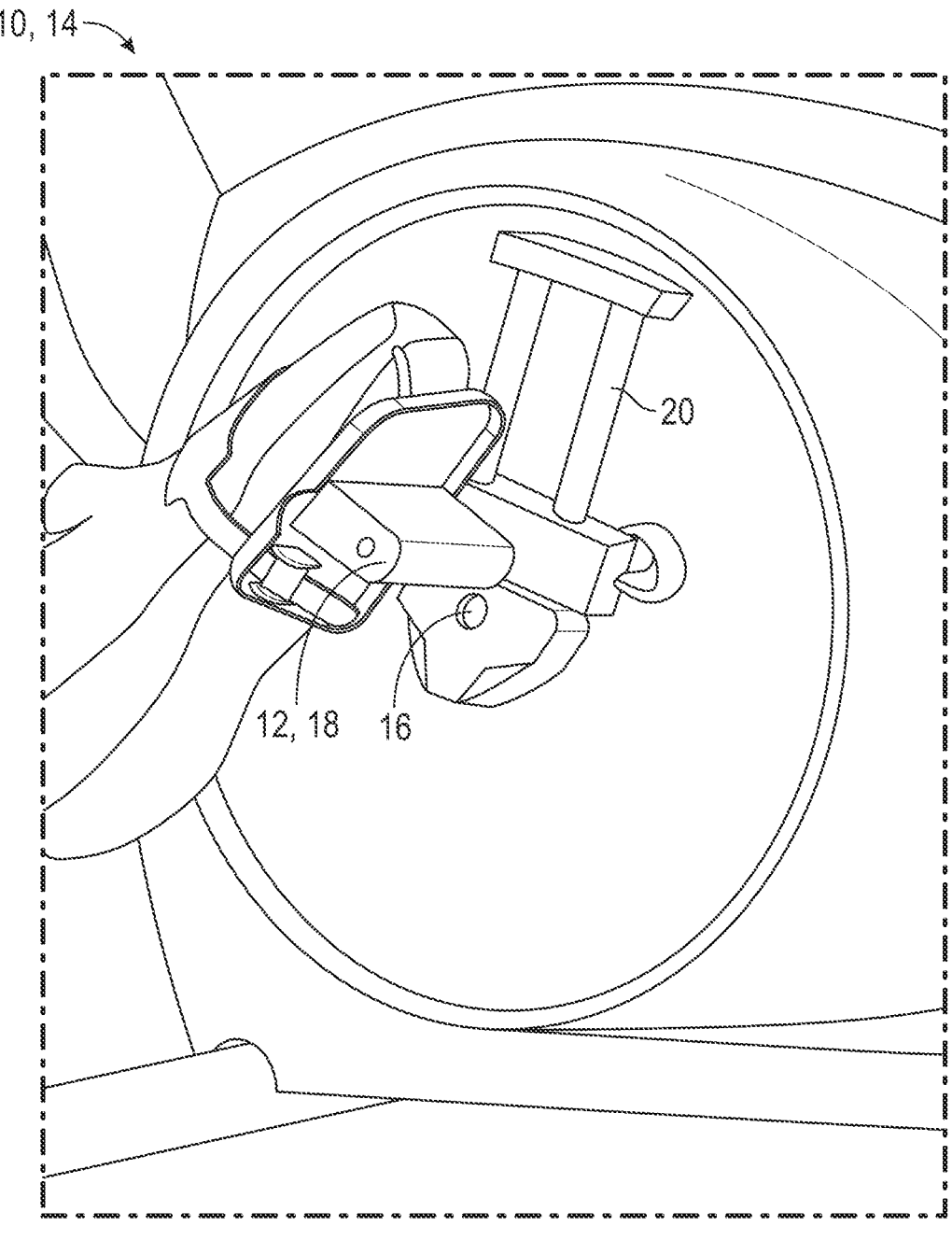
FIG. 8 generally illustrates a perspective view of a pedal of the treatment device of FIG. 7 according to certain aspects of this disclosure.

FIGS. 7-8 generally illustrate an embodiment of a treatment device, such as a treatment device 10. More specifically, FIG. 7 generally illustrates a treatment device 10 in the form of an electromechanical device, such as a stationary cycling machine 14, which may be called a stationary bike, for short. The stationary cycling machine 14 includes a set of pedals 12 each attached to a pedal arm 20 for rotation about an axle 16. In some embodiments, and as generally illustrated in FIG. 8, the pedals 12 are movable on the pedal arm 20 in order to adjust a range of motion used by the patient in pedaling. For example, the pedals being located inwardly toward the axle 16 corresponds to a smaller range of motion than when the pedals are located outwardly away from the axle 16. A pressure sensor 18 is attached to or embedded within one of the pedals 12 for measuring an amount of force applied by the patient on the pedal 102. The pressure sensor 18 may communicate wirelessly to the treatment device 10 and/or to the patient interface 26. FIGS. 7-8 are not intended to be limiting; the treatment device 10 may include more or fewer components than those illustrated in FIGS. 7-8.

Figure 9:
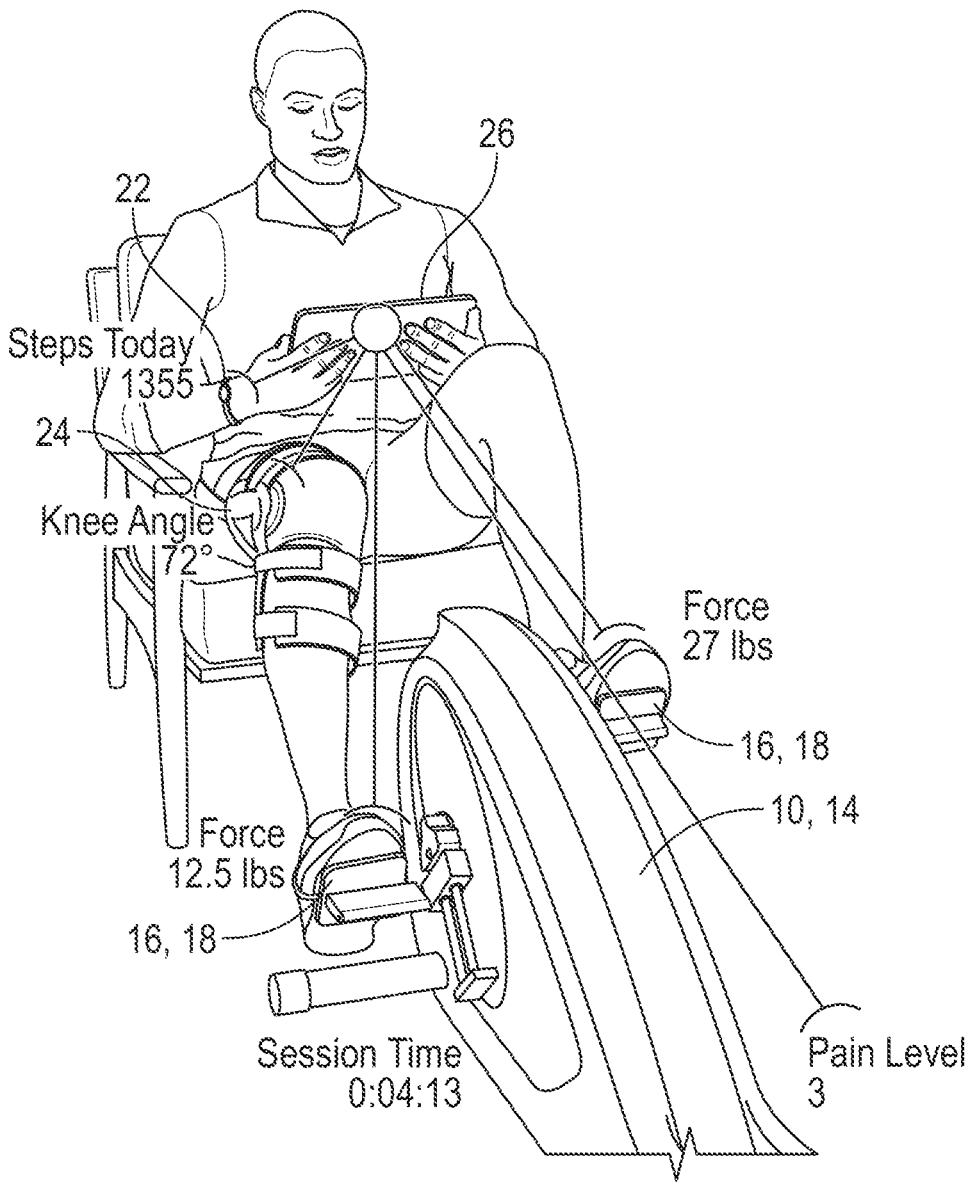
FIG. 9 generally illustrates a perspective view of a person using the treatment device of FIG. 7 according to certain aspects of this disclosure.

FIG. 9 generally illustrates a person (a patient) using the treatment device 10 of FIG. 7, and showing sensors and various data parameters connected to a patient interface 26. The example patient interface 26 is a tablet computer or smartphone, or a phablet, such as an iPad, an iPhone, an Android device, or a Surface tablet, which is held manually by the patient. In some other embodiments, the patient interface 26 may be embedded within or attached to the treatment device 10. FIG. 9 generally illustrates the patient wearing the ambulation sensor 22 on his wrist, with a note showing "STEPS TODAY 1355", indicating that the ambulation sensor 22 has recorded and transmitted that step count to the patient interface 26. FIG. 9 also generally illustrates the patient wearing the goniometer 24 on his right knee, with a note showing "KNEE ANGLE 72°", indicating that the goniometer 24 is measuring and transmitting that knee angle to the patient interface 26. FIG. 9 generally illustrates a right side of one of the pedals 12 with a pressure sensor 18 showing "FORCE 12.5 lbs.", indicating that the right pedal pressure sensor 18 is measuring and transmitting that force measurement to the patient interface 26. FIG. 9 also generally illustrates a left side of one of the pedals 12 with a pressure sensor 18 showing "FORCE 27 lbs.", indicating that the left pedal pressure sensor 18 is measuring and transmitting that force measurement to the patient interface 26. FIG. 9 also generally illustrates other patient data, such as an indicator of "SESSION TIME 0:04:13", indicating that the patient has been using the treatment device 10 for 4 minutes and 13 seconds. This session time may be determined by the patient interface 26 based on information received from the treatment device 10. FIG. 9 also generally illustrates an indicator showing "PAIN LEVEL 3". Such a pain level may be obtained from the patient in response to a solicitation, such as a question, presented upon the patient interface 26.

The medical device 102 may include an electromechanical device 104, such as pedals of a physical therapy cycle, a goniometer configured to attach to a joint and measure joint angles, or any other suitable electromechanical device 104. The electromechanical device 104 may be configured to transmit information, such as positioning information. A non-limiting example of positioning information includes information relating to the location of pedals of the physical therapy cycle 200. The medical device 102 may include a sensor 106. The sensor 106 can be used for obtaining information to be used in generating a biometric signature. A biometric signature, for the purpose of this disclosure, is a signature derived from certain biological characteristics of a user. The biometric signature can include information of a user, such as fingerprint information, retina information, voice information, height information, weight information, vital sign information (e.g., blood pressure, heart rate, etc.), response information to physical stimuli (e.g., change in heart rate while running on a treadmill), performance information (rate of speed on the electromechanical device 104), or any other suitable biological characteristic(s) of the user. The biometric signature may include and/or be determined by a kinesiological signature. A kinesiological signature, for the purpose of this disclosure, refers to a signature derived from human body movement, such as information about a range of motion of or about a user's joint, e.g., a knee, an elbow, a neck, a spine, or any other suitable joint, ligament, tendon, or muscle of a human. The sensor 106 may be a temperature sensor (such as a thermometer or thermocouple), a strain gauge, a proximity sensor, an accelerometer, an inclinometer, an infrared sensor, a pressure sensor, a light sensor, a smoke sensor, a chemical sensor, any other suitable sensor, a fingerprint scanner, a sound sensor, a microphone, or any combination thereof. The medical device 102 may include, for obtaining information to be used in generating a biometric signature, a camera 108, such as a still image camera, a video camera, an infrared camera, an X-ray camera, any other suitable camera, or any combination thereof. The medical device 102 may include, for obtaining information to be used in generating a biometric signature, an imaging device 110, such as an MM imaging device, an X-ray imaging device, a thermal imaging device, any other suitable imaging device, or any combination thereof.

The medical device 102 may include, be coupled to, or be in communication with a computing device 112. The computing device 112 may include a processor 114. The processor 114 can include, for example, computers, intellectual property (IP) cores, application-specific integrated circuits (ASICs), programmable logic arrays, optical processors, programmable logic controllers, microcode, microcontrollers, servers, microprocessors, digital signal processors, any other suitable circuit, or any combination thereof.

The computing device 112 may include a memory device 116 in communication with the processor 114. The memory device 116 can include any type of memory capable of being accessed by a computer, such as read only memory (ROM), random access memory (RAM), a hard disk drive, a flash drive, a compact disc (CD), a digital video disc (DVD), solid state drive (SSD), or any other suitable type of memory.

The computing device 112 may include an input device 118 in communication with the processor 114. Examples of the input device 118 include a keyboard, a keypad, a mouse, a microphone supported by speech-to-text software, or any other suitable input device. The input device 118 may be used by a medical system operator to input information, such as user-identifying information, observational notes, or any other suitable information. An operator is to be understood throughout this disclosure to include both people and computer software, such as programs or artificial intelligence.

The computing device 112 may include an output device 120 in communication with the processor 114. The output device 120 may be used to provide information to the medical device operator or a user of the medical device 102. Examples of the output device 120 may include a display screen, a speaker, an alarm system, or any other suitable output device, including haptic, tactile, olfactory, or gustatory ones, and without limitation, gesture recognition, gesture control, touchless user interfaces (TUIs), kinetic user interfaces (KUIs), tangible user interfaces, wired gloves, depth-aware cameras, stereo cameras, and gesture-based controllers. In some embodiments, such as where the computing device 112 includes a touchscreen, the input device 118 and the output device 120 may be the same device.

For communicating with remote computers and servers, the computing device 112 may include a network adapter 122 in communication with the processor 114. The network adapter 122 may include wired or wireless network adapter devices or a wired network port.

Any time information is transmitted or communicated, the information may be in EDI file format or any other suitable file format. In any of the methods or steps of the method, file format conversions may take place. By utilizing Internet of Things (IoT) gateways, data streams, ETL bucketing, EDI mastering, or any other suitable technique, data can be mapped, converted, or transformed into a carrier preferred state. As a result of the volume of data being transmitted, the data security requirements, and the data consistency requirements, enterprise grade architecture may be utilized for reliable data transfer.

FIG. 1 is not intended to be limiting; the medical system 100 and the computing device 112 may include more or fewer components than those illustrated in FIG. 1.

Figure 3:
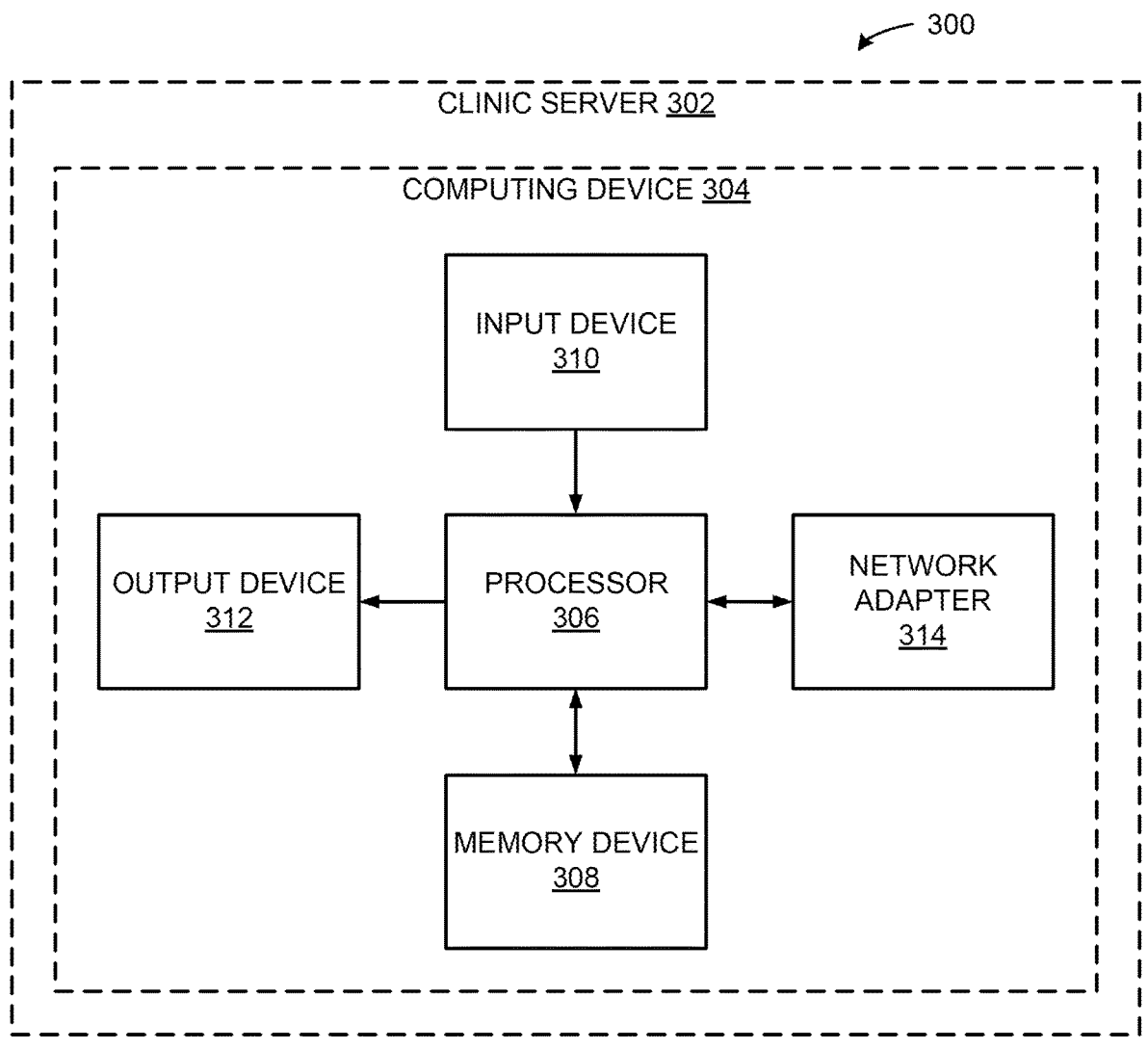
FIG. 3 generally illustrates a component diagram of an illustrative clinic server system according to the principles of this disclosure.

FIG. 3 illustrates a component diagram of an illustrative clinic server system 300 in accordance with aspects of this disclosure. The clinic server system 300 may include a clinic server 302. The clinic server system 300 or clinic server 302 may be servers owned or controlled by a medical clinic (such as a doctor's office, testing site, or therapy clinic) or by a medical practice group (such as a testing company, outpatient procedure clinic, diagnostic company, or hospital). The clinic server 302 may be proximate to the medical system 100. In other embodiments, the clinic server 302 may be remote from the medical system 100. For example, during telemedicine-based or telemedicine-mediated treatment, rehabilitation, or testing, the clinic server 302 may be located at a healthcare clinic and the medical system 100 may be located at a patient's home. The clinic server 302 may be a rackmount server, a router computer, a personal computer, a portable digital assistant, a smartphone, a laptop computer, a tablet computer, a netbook, a desktop computer, any other suitable computing device, or any combination of the above. The clinic server 302 may be cloud-based or be a real-time software platform, and it may include privacy (e.g., anonymization, pseudonymization, or other) software or protocols, and/or include security software or protocols. The clinic server 302 may include a computing device 304. The computing device 304 may include a processor 306. The processor 306 can include, for example, computers, intellectual property (IP) cores, application-specific integrated circuits (ASICs), programmable logic arrays, optical processors, programmable logic controllers, microcode, microcontrollers, servers, microprocessors, digital signal processors, any other suitable circuit, or any combination thereof.

The computing device 304 may include a memory device 308 in communication with the processor 306. The memory device 308 can include any type of memory capable of being accessed by a computer, such as read only memory (ROM), random access memory (RAM), a hard disk drive, a flash drive, a compact disc (CD), a digital video disc (DVD), a solid state drive (SSD), or any other suitable type of memory.

The computing device 304 may include an input device 310 in communication with the processor 306. Examples of the input device 310 include a keyboard, a keypad, a mouse, a microphone supported by speech-to-text software, or any other suitable input device.

The computing device 304 may include an output device 312 in communication with the processor 114. Examples of the output device 312 include a display screen, a speaker, an alarm system, or any other suitable output device, including haptic, tactile, olfactory, or gustatory ones, and without limitation, gesture recognition, gesture control, touchless user interfaces (TUIs), kinetic user interfaces (KUIs), tangible user interfaces, wired gloves, depth-aware cameras, stereo cameras, and gesture-based controllers. In some embodiments, such as where the computing device 304 includes a touchscreen, the input device 310 and the output device 312 may be the same device.

The computing device 304 may include a network adapter 314 in communication with the processor 306 for communicating with remote computers and/or servers. The network adapter 314 may include wired or wireless network adapter devices.

FIG. 3 is not intended to be limiting; the clinic server system 300, the clinic server 302, and the computing device 304 may include more or fewer components than those illustrated in FIG. 3.

Figure 4:
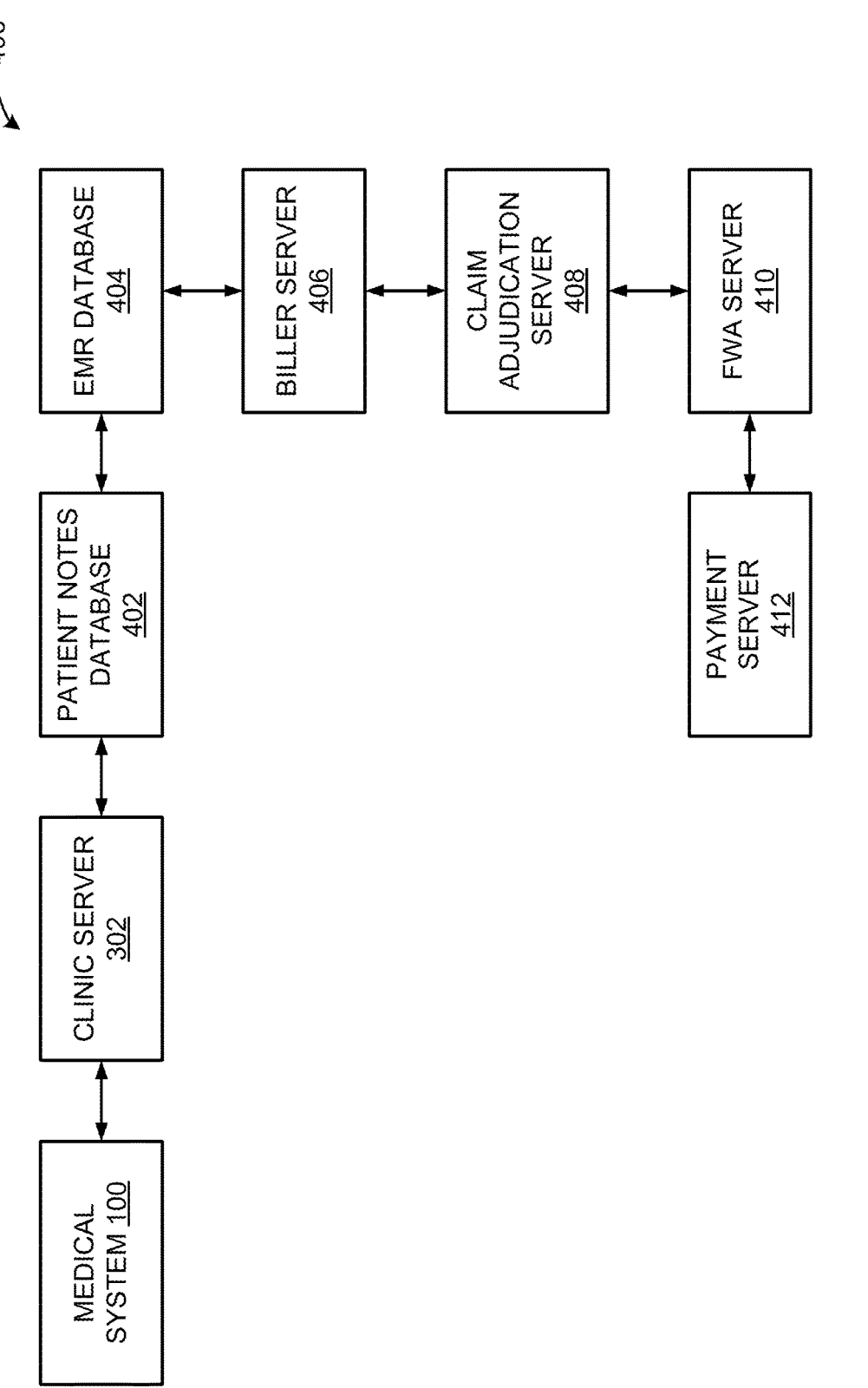
FIG. 4 generally illustrates a component diagram and method of an illustrative medical claim processing system according to the principles of this disclosure.

FIG. 4 illustrates a component diagram and method of an illustrative medical claim processing system 400 and information flow according to aspects of this disclosure. The medical claim processing system 400 may include the medical system 100. The medical claim processing system 400 may include a clinic server 302.

The medical claim processing system 400 may include a patient notes database 402. The patient notes database 402 may include information input by a clinic operator or information received from the clinic server 302. For example, the clinic operator may enter information obtained manually about a patient's height and weight and/or information received from the patient about a condition from which the patient is suffering. The medical claim processing system 400 may include an electronic medical records (EMR) database 404. The EMR database 404 may include information input by a clinic operator and/or information received from the clinic server 302 or the patient notes database 402. For example, the EMR database 404 may contain information received from the medical devices 102 or historical information obtained from patient notes database 402, such as historical height and weight information. One or both of the patient notes database 402 and the EMR database 404 may be located on the clinic server 302, on one or more remote servers, or on any other suitable system or server.

The medical claim processing system 400 may include a biller server 406. The biller server 406 may receive medical service information from the medical system 100; the clinic server 302; the patient notes database 402; the EMR database 404; any suitable system, server, or database; or any combination thereof. The medical service information may include medical coding information. By correlating the medical service information with an associated medical code, the biller server 406 may determine medical coding information. The biller server 406 may determine one or more responsible parties for payment of medical bills. Using the medical codes, the biller server 406 may generate an invoice. The biller server 406 may transmit the medical coding information and medical service information to the responsible party or parties. The biller server 406 may be owned or controlled by a medical practice group (such as a testing company, an outpatient procedure clinic, a diagnostic company, or a hospital), a health insurance company, a governmental entity, or any other organization (including third-party organizations) associated with medical billing procedures. The biller server 406 may be a rackmount server, a router computer, a personal computer, a portable digital assistant, a smartphone, a laptop computer, a tablet computer, a netbook, a desktop computer, any other suitable computing device, or any combination of the above. The biller server 406 may be cloud-based or be a real-time software platform, and it may include privacy (e.g., anonymization, pseudonymization, or other) software or protocols, and/or include security software or protocols. The biller server 406 may contain a computing device including any combination of the components of the computing device 304 as illustrated in FIG. 3. The biller server 406 may be proximate to or remote from the clinic server 302.

The medical claim processing system 400 may include a claim adjudication server 408. The claim adjudication server 408 may be owned or controlled by a health insurance company, governmental entity, or any other organization (including third-party organizations) associated with medical billing procedures. The claim adjudication server 408 may be a rackmount server, a router computer, a personal computer, a portable digital assistant, a smartphone, a laptop computer, a tablet computer, a netbook, a desktop computer, any other suitable computing device, or any combination of the above. The claim adjudication server 408 may be cloud-based or be a real-time software platform, and it may include privacy (e.g., anonymization, pseudonymization, or other) software or protocols, and/or include security software or protocols. The claim adjudication server 408 may contain a computing device including any combination of the components of the computing device 304 as illustrated in FIG. 3. The claim adjudication server 408 may be proximate to or remote from the biller server 406. The claim adjudication server 408 may be configured to make or receive a determination about whether a claim should be paid.

The medical claim processing system 400 may include a fraud, waste, and abuse (FWA) server 410. The FWA server 410 may be owned or controlled by a health insurance company, a governmental entity, or any other organization (including a third-party organization) associated with medical billing procedures. The FWA server 410 may be a rackmount server, a router computer, a personal computer, a portable digital assistant, a smartphone, a laptop computer, a tablet computer, a netbook, a desktop computer, any other suitable computing device, or any combination of the above. The FWA server 410 may be cloud-based or be a real-time software platform, and it may include privacy-enhancing, privacy-preserving, or privacy modifying software or protocols (e.g., anonymization, pseudonymization, or other), and/or include security software or protocols. The FWA server 410 may contain a computing device including any combination of the components of the computing device 304 as illustrated in FIG. 3. The FWA server 410 may be proximate to or remote from the claim adjudication server 408. The FWA server 410 may be configured to make or receive a determination about whether a medical claim should be paid. The FWA server 410 may be configured to make or receive a determination about whether a proposed payment for a medical claim is a result of fraud, waste, or abuse.

The medical claim processing system 400 may include a payment server 412. The payment server 412 may be owned or controlled by a health insurance company, a governmental entity, or any other organization (including a third-party organization) associated with medical billing procedures. The payment server 412 may be a rackmount server, a router computer, a personal computer, a portable digital assistant, a smartphone, a laptop computer, a tablet computer, a netbook, a desktop computer, any other suitable computing device, or any combination of the above. The payment server 412 may be cloud-based or be a real-time software platform, and it may include privacy-enhancing, privacy-preserving, or privacy modifying software or protocols (e.g., anonymization, pseudonymization, or other), and/or include security software or protocols. The payment server 412 may contain a computing device including any combination of the components of the computing device 304. The payment server 412 may be proximate to or remote from the biller server 406 and/or the FWA server 410. The payment server 412 may be configured to make or receive a determination about whether a claim should be paid. The payment server 412 may be configured to make or receive a determination about whether a proposed payment is, wholly or partially, a direct or indirect result of fraud, waste, or abuse. The payment server 412 may be configured to process or transmit a payment to the service provider.

FIG. 4 is not intended to be limiting; the medical claim processing system 400 and any sub-components thereof may include more or fewer components, steps, and/or processes than those illustrated in FIG. 4. Any of the components of the medical claim processing system 400 may be in direct or indirect communication with each other. Any or all of the methods described may be implemented during a telemedicine session or at any other desired time.

Figure 5:
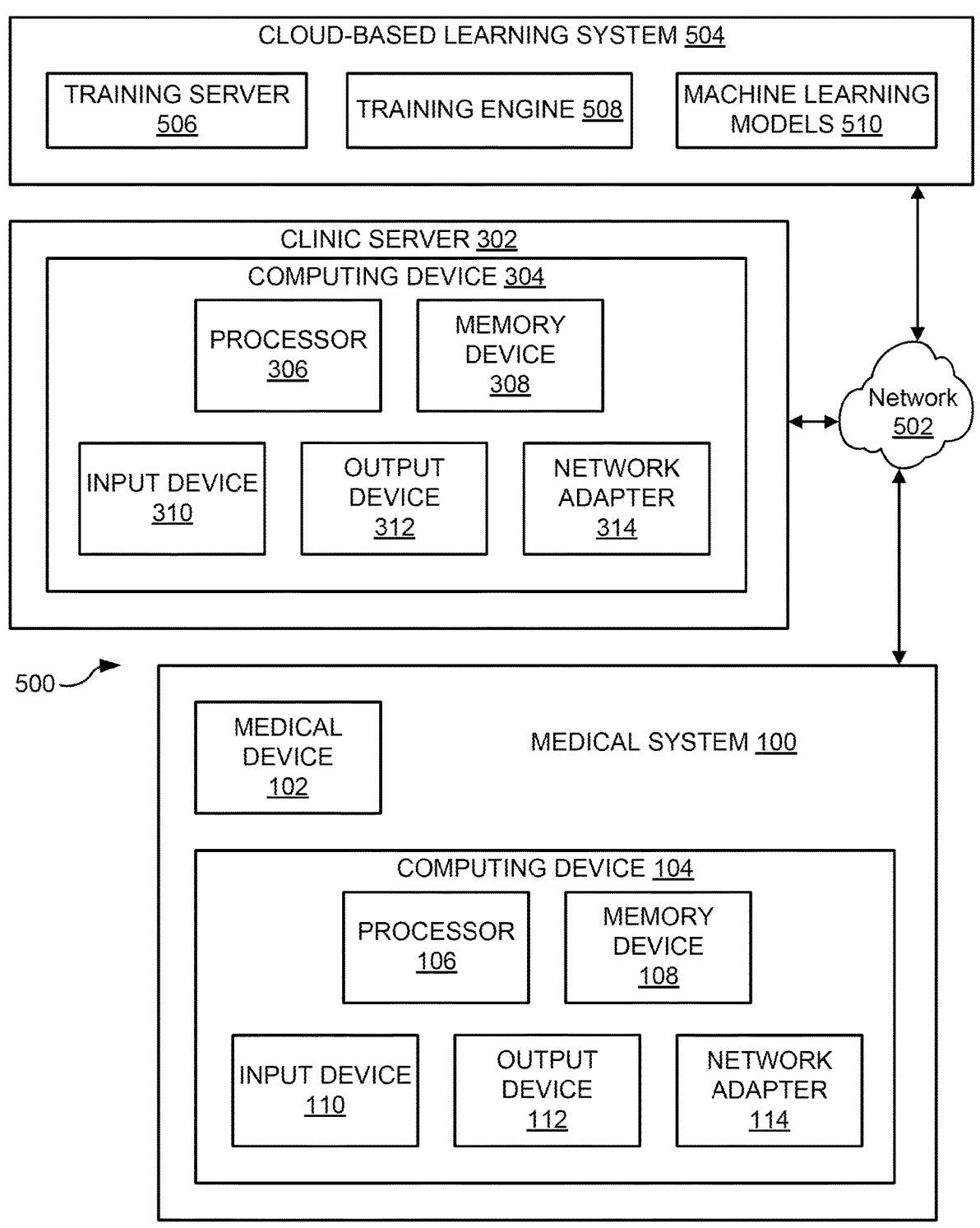
FIG. 5 generally illustrates a component diagram of an alternative arrangement of an illustrative medical claim processing system according to the principles of this disclosure.

FIG. 5 illustrates a component diagram of an illustrative medical claim processing system 500 according to aspects of this disclosure. The medical claim processing system 500 can include the medical system 100 of FIG. 1. The medical system 100 may be in communication with a network 502. The network 502 may be a public network (e.g., connected to the Internet via wired (Ethernet) or wireless (Wi-Fi)), a private network (e.g., a local area network (LAN) or a wide area network (WAN)), a combination thereof, or any other suitable network.

The medical claim processing system 500 can include the clinic server 302. The clinic server 302 may be in communication with the network 502. The clinic server 302 is shown as an example of servers that can be in communication with the network 502. In addition to or in place of the clinic server 302, the medical claim processing system 500 can include the biller server 406, the claim adjudication server 408, the FWA server 410, the payment server 412, or any combination thereof.

The medical claim processing system 500 can include a cloud-based learning system 504. For example, the cloud-based learning system 504 may be used to update or change a first biometric signature (i.e., a predicted biometric signature) of a user using historical device-based signature information relating to the user or other users, such as those with similar medical conditions, medical services provided, demographics, or any other suitable similarity. The cloud-based learning system 504 may be used to update or change an algorithm for generating a signature indicator. The signature indicator can include whether the first biometric signature (i.e., the predicted biometric signature) matches a second biometric signature (i.e., a device-based biometric signature). Examples of signature indicators include flags and computer-coded variables. The cloud-based learning system 504 may be in communication with the network 502. The cloud-based learning system 504 may include one or more training servers 506 and form a distributed computing architecture. Each of the training servers 506 may include a computing device, including any combination of one or more of the components of the computing device 304 as illustrated in FIG. 3, or any other suitable components. The training servers 506 may be in communication with one another via any suitable communication protocol. The training servers 506 may store profiles for users including, but not limited to, patients, clinics, practice groups, and/or insurers. The profiles may include information such as historical device-generated information, historical device-based medical coding information, historical reviewed medical coding information, historical electronic medical records (EMRs), historical predicted biometric signatures, historical device-based biometric signatures, historical signature comparisons, historical signature indicators, historical emergency biometric signatures, historical emergency comparisons, historical emergency indicators, and any other suitable historical information. Other non-limiting examples of suitable historical information can include any information relating to a specific patient, a condition, or a population that was recorded at a time prior to the interaction presently being billed as the medical claim.

In some aspects, the cloud-based learning system 504 may include a training engine 508 capable of generating one or more machine learning models 510. The machine learning models 510 may be trained to generate algorithms that aid in determining the device-based medical coding information, for example, by using the device generated information or generation of predicted biometric signatures, device-based biometric signatures, signature indicators, emergency biometric signatures, and/or emergency indicators. For example, if the medical device 102 is an MRI machine, the machine learning models 510 may use the device-generated information generated by the MRI machine (e.g., MRI images) to generate progressively more accurate algorithms to determine which type of medical procedure (e.g., MM scan) was performed and which type of medical coding information (e.g., 73720, 73723, and 74183) to associate with the medical procedure performed, predicted biometric signatures, and/or signature indicators. To generate the one or more machine learning models 510, the training engine 508 may train the one or more machine learning models 510. The training engine 508 may use a base data set of historical device-generated information (e.g., generated from the medical device), historical device-based medical coding information, historical reviewed medical coding information, historical electronic medical records (EMRs), historical predicted biometric signatures, historical device-based biometric signatures, historical signature comparisons, historical signature indicators, historical emergency biometric signatures, historical emergency comparisons, historical emergency indicators, and any other suitable historical information. The training engine 508 may be in communication with the training servers 506. The training engine 508 may be located on the training servers 506.

The training engine 508 may be a rackmount server, a router computer, a personal computer, a portable digital assistant, a smartphone, a laptop computer, a tablet computer, a netbook, a desktop computer, an Internet of Things (IoT) node or sensor, any other suitable computing device, or any combination of the above. The training engine 508 may be cloud-based or be a real-time software platform, and it may include privacy-enhancing, privacy-preserving, or privacy modifying software or protocols (e.g., anonymization, pseudonymization, or other), and/or include security software or protocols. Using training data that includes training inputs and corresponding target outputs, the one or more machine learning models 510 may refer to model artifacts created by the training engine 508. The training engine 508 may find patterns in the training data that map the training input to the target output and generate the machine learning models 510 that identify, store, or use these patterns. Although depicted separately from the medical system 100, the clinic server 302, the biller server 406, the claim adjudication server 408, the training engine 508, and the machine learning models 510 may reside on the medical system 100. Alternatively, the clinic server 302, the biller server 406, the claim adjudication server 408, the training engine 508, and the machine learning models 510 may reside on the clinic server 302, the biller server 406, the claim adjudication server 408, the FWA server 410, the payment server 412, any other suitable computer device or server, or any combination thereof.

The machine learning models 510 may include one or more neural networks, such as an image classifier, a recurrent neural network, a convolutional network, a generative adversarial network, a fully connected neural network, any other suitable network, or combination thereof. In some embodiments, the machine learning models 510 may be composed of a single level of linear or non-linear operations or may include multiple levels of non-linear operations. For example, the machine learning models 510 may include numerous layers and/or hidden layers that perform calculations (e.g., dot products) using various neural nodes.

Any of the medical system 100, the computing device 112 of the medical system 100, the clinic server 302, the biller server 406, the claim adjudication server 408, the FWA server 410, the payment server 412, the training server 506, the training engine 508, any other suitable computing device, or any combination thereof may be configured to receive device-generated information from a medical device. The device-generated information may be information generated by the medical device. The medical device may include the medical device 102. The medical device 102 may include the medical system 100. The device-generated information can include information obtained by the electromechanical device 104, the sensor 106, the camera 108, the imaging device 110, any other portion of the medical device 102, any separate or remote electromechanical device, any separate or remote sensor, any separate remote camera, any separate or remote imaging device, any other suitable device, or any combination thereof. The device-generated information may include vital sign information, such as heart rate, blood oxygen content, blood pressure, or any other suitable vital sign. The device-generated information may include images, such as MM images, X-ray images, video camera images, still camera images, infrared images, or any other suitable images. The device-generated information may also include performance information (i.e., information relating to the physical performance of the user while the user operates a medical device), such as a rate of pedaling of a physical therapy cycle, a slope of a treadmill, a force applied to a straingauge, a weight lifted, a (simulated) distance traveled on a treadmill, or any other suitable performance information. The device-generated information may include medical device use information, such as a location of the medical device 102, a healthcare provider associated with the medical device 102, a practice group associated with the medical device 102, a time of day that the medical device 102 was used, a date that the medical device 102 was used, a duration that the medical device 102 was used, or any other suitable medical device use information.

Any of the medical system 100, the computing device 112 of the medical system 100, the clinic server 302, the biller server 406, the claim adjudication server 408, the FWA server 410, the payment server 412, the training server 506, the training engine 508, any other suitable computing device, or any combination thereof may be configured to use the device-generated information to determine device-based medical coding information. Determining device-based medical coding information can include cross-referencing information about actions performed by or with the medical device 102 contained within the device-generated information with a reference list associating the actions performed by or with the medical device 102 with certain medical codes. The reference list can be stored on the clinic server 302, as part of the cloud-based learning system 504, or on any other suitable server, database, or system. Determining device-based medical coding information can include identifying a portion of the device-generated information containing medical coding information.

Any of the medical system 100, the computing device 112, the clinic server 302, the biller server 406, the claim adjudication server 408, the FWA server 410, the payment server 412, the training server 506, the training engine 508, any other suitable computing device, or any combination thereof, may be configured to receive reviewed medical coding information. The reviewed medical coding information can include medical coding information reviewed or entered by a clinic operator. Reviewed medical coding information can include information about previously performed medical processes, procedures, surgeries, or any other suitable reviewed coding information. The reviewed medical coding information can be medical coding information that a clinic operator has reviewed on a computing device or entered into a computing device. For example, a surgeon can review and revise, on a computing device, medical coding information about a surgery that the surgeon performed on a patient (user).

Any of the medical system 100, the computing device 112 of the medical system 100, the clinic server 302, the biller server 406, the claim adjudication server 408, the FWA server 410, the payment server 412, the training server 506, the training engine 508, any other suitable computing device, or any combination thereof may be configured to generate a predicted biometric signature (i.e., a first biometric signature). The predicted biometric signature may include and/or be determined by a kinesiological signature. For example, the predicted biometric signature can include a predicted movement such as a range of motion of a user's joint, such as a knee, an elbow, a neck, a spine, or any other suitable joint or muscle of a human. The predicted biometric signature may be based at least in part on historical information. In an example where a patient is using a physical therapy cycle 200, such cycle preferably located at the patient's home or residence, as part of telemedicine-enabled or -mediated rehabilitation therapy, then, using past camera images of the user taken by the device, the predicted biometric signature can include an expected image of the user. The predicted biometric signature may be based at least in part on the reviewed medical coding information. For example, where a user has undergone a specific back surgery, the predicted biometric signature may include an MM image of the user's upper back, such image showing evidence of that surgery. The predicted biometric signature may be based at least in part on the device-based medical coding information. For example, if the device-based medical coding information indicates that the user has undergone an upper-back MM, the predicted biometric signature may be based at least in part on how the image of the upper back is expected to appear based on other historical information, such as past surgeries identified using the reviewed medical coding information. The predicted biometric signature may be based at least in part on Electronic Medical Records (EMRs). For example, the predicted biometric signature may be based at least in part on a height value and a weight value entered into the EMRs. The predicted biometric signature may be based at least in part on historical performance information (i.e., performance information generated in the past relating to a specific user or other users). For example, the predicted biometric signature may be based at least in part on a determination that a patient's performance on the physical therapy cycle 200 should be within a certain range of the patient's last performance on the physical therapy cycle 200. The determination may be modified using the amount of time since the patient has last used the physical therapy cycle 200. The predicted biometric signature may be derived from any other suitable information, or any combination of any of the previous examples of information from which the predicted biometric signature is derived. Further, if the predicted biometric signature includes a kinesiological signature, the predicted biometric signature may be derived from any other suitable information, or any combination of any of the previous examples of information from which the predicted biometric signature is derived. For example, reviewed medical coding information relating to a knee surgery may be used to determine knee joint motion.

Any of the medical system 100, the computing device 112 of the medical system 100, the clinic server 302, the biller server 406, the claim adjudication server 408, the FWA server 410, the payment server 412, the training server 506, the training engine 508, any other suitable computing device, or any combination thereof may be configured to, using the device-generated information, generate a device-based biometric signature (i.e., a second biometric signature). The device-based biometric signature may be a kinesiological signature. For example, the device-based biometric signature can include the movement and joint range of a user's knee. The device-based biometric signature may be based at least in part on the device-based medical coding information. For example, where the device-based medical coding information suggests that the user has undergone an upper-back MM, the device-based biometric signature may be based at least in part on the device-generated information about the upper back. The device-based biometric signature may be based at least in part on the performance information. For example, the device-based biometric signature may be derived from a rate of pedaling of a physical therapy cycle 200, a slope of a treadmill, a force applied to a strain-gauge, a weight lifted, a (simulated) distance traveled on a treadmill, or any other suitable performance information. The device-based biometric signature may be derived from images included in the device-generated information, such as MM images, X-ray images, video camera images, still camera images, infrared images, or any other suitable images. The device-based biometric signature may be derived from any other suitable information, or any combination of any of the previous examples of information upon with the device-based biometric signature is based. Further, if the device-based biometric signature includes a kinesiological signature, the device-based biometric signature may be derived from any other suitable information, or any combination of any of the previous examples of information upon with the device-based biometric signature is based. For example, camera images may be used to determine knee joint motion as a kinesiological signature embodiment of the device-based biometric signature.

Any of the medical system 100, the computing device 112 of the medical system 100, clinic server 302, the biller server 406, the claim adjudication server 408, the FWA server 410, the payment server 412, the training server 506, the training engine 508, any other suitable computing device, or any combination thereof may be configured to use the predicted biometric signature and the device-based biometric signature to generate a signature comparison. The signature comparison can include differences in terms of degrees between the predicted biometric signature and the device-based biometric signature. For example, if the predicted biometric signature includes height information for a user with a value of 5 feet 4 inches and the device-based biometric signature includes height information for a user with a value of 5 feet 5 inches, the degree of difference between the predicted biometric signature and the device-based biometric signature may be indicated to be below a FWA threshold value. However, if the predicted biometric signature includes height information for a user with a value of 5 feet 4 inches and the device-based biometric signature includes height information for a user with a value of 5 feet 9 inches tall, the degree of difference between the predicted biometric signature and the device-based biometric signature may be noted to be above the FWA threshold value.

Any of the medical system 100, the computing device 112 of the medical system 100, the clinic server 302, the biller server 406, the claim adjudication server 408, the FWA server 410, the payment server 412, the training server 506, the training engine 508, any other suitable computing device, or any combination thereof may be configured to use the signature comparison to generate a signature indicator. To indicate an incorrect user, the signature indicator can include flagging when the signature comparison is outside an acceptable user threshold. For example, if the predicted biometric signature includes height information for a user with a height value of 5 feet 4 inches tall and the device-based biometric signature includes height information for a user with a value of 5 feet 9 inches tall, a signature indicator may be generated. The signature indicator may indicate that the difference between the predicted biometric signature and the device-based biometric signature is above the FWA threshold value. This difference may be the result of an incorrect user using the medical device. Another example includes generating a signature indicator in response to differences in between the predicted biometric signature and the device-based biometric signature, as derived from the performance metric information and the vital sign information, such that the processor 114 determines that the differences are above a FWA threshold. In response to this determination, the processor 114 generates the signature indicator. In this example, a post-knee surgery user walked a mile in 45 minutes on a treadmill with an average heartrate of 190 beats per minute (bpm) (i.e., the user struggled to walk a mile) and the same user later walked 5 miles on the treadmill in 45 minutes with a heartrate of 130 bpm (i.e., the user did not struggle to walk more than a mile in the same time). Another example includes a camera image displaying different images of users for the same billing user, as determined by using facial recognition software. Another example includes a user with a low range of movement in his knee joint on a first day and the same user with a high range of movement in his knee joint on a consecutive day (i.e., a kinesiological signature above the FWA threshold). The signature indicator can include flagging if the differences are determined to be the result of any errors or inconsistencies in the EMRs or reviewed medical coding information. For example, if the predicted biometric signature is based on a certain type of surgery, and the device-based biometric signature is not consistent with such surgery (i.e., consistent with a less-intense surgery—perhaps one not requiring as intense or expensive a physical therapy regimen), a signature indicator may be generated. The signature indicator may be transmitted to an operator to indicate that there is an error or an inconsistency in the EMRs or reviewed medical coding information.

Any of the medical system 100, the computing device 112, the clinic server 302, the biller server 406, the claim adjudication server 408, the FWA server 410, the payment server 412, the training server 506, the training engine 508, any other suitable computing device, or any combination thereof may be configured to transmit the signature indicator. For example, any of the medical system 100, the computing device 112 of the medical system 100, the clinic server 302, the biller server 406, the claim adjudication server 408, the FWA server 410, the payment server 412, the training server 506, the training engine 508, any other suitable computing device, or any combination thereof may transmit the signature indicator (e.g., a flag) to the medical system 100, the computing device 112 of the medical system 100, clinic server 302, the biller server 406, the claim adjudication server 408, the FWA server 410, the payment server 412, the training server 506, the training engine 508, any other suitable computing device, or any combination thereof.

The signature indicator may be used by the receiving system or the server. In one exemplary embodiment, at the medical system 100, the signature indicator can be used to validate information and/or to set a flag to inform an operator of the medical system 100 or medical device 102 that there is a biometric signature mismatch and, for example, the wrong therapy may have been prescribed to a patient. In another exemplary embodiment, the clinic server 302 can use the signature indicator to validate information and/or to determine whether to transmit a message to an operator or administrator. The message may include information indicating a biometric signature mismatch and/or information improperly entered into the EMR database 404. In another exemplary embodiment, the biller server 406 may use the signature indicator to validate information received or sent and/or to not send the medical coding information to the claim adjudication server 408 until the biometric signature is matched. In another exemplary embodiment, the claim adjudication server 408 may use the may use the signature indicator to (1) validate information received; (2) determine that a flag should be added to the medical coding information prior to transmitting the medical coding information to the FWA server 410 and/or the payment server 412; or (3) receive additional information from the FWA server 410. In another exemplary embodiment, the FWA server 410 can use the signature indicator to (1) validate information received, (2) determine whether to transmit a message, and/or (3) make a determination of whether to flag the medical coding information as fraudulent and transmit a message to initiate a FWA investigation. In another exemplary embodiment, the payment server 412 can use the signature indicator to validate information received and/or to determine whether to pay the medical service provider. In another exemplary embodiment, the training server 506 and/or the training engine 508 can use the signature indicator for further machine learning activities (i.e., by increasing the size of the dataset every time a signature indicator is generated).

Any of the medical system 100, the computing device 112 of the medical system 100, the clinic server 302, the biller server 406, the claim adjudication server 408, the FWA server 410, the payment server 412, the training server 506, the training engine 508, any other suitable computing device, or any combination thereof may be configured to generate an emergency biometric signature for use in detecting and responding to an emergency event. When a user is undergoing telemedicine-enabled or -mediated rehabilitation therapy without direct supervision by a trained medical professional, automatically (including, without limitation, through means of artificial intelligence and/or machine learning) recognizing and responding to emergency events may be desirable in the event that an emergency situation occurs. The emergency biometric signature can be derived from the predicted biometric signature. The emergency biometric signature may include vital sign information (a user's heart rate or blood pressure being too high or too low), imagery (a user's face turning purple), or any other suitable information. In an example where a patient is using a physical therapy cycle 200 located at the patient's home or residence to undergo telemedicine-enabled or -mediated rehabilitation therapy, the emergency biometric signature can include a value of a heart-rate of a user that is above an emergency threshold value. The emergency threshold may be derived from the predicted biometric signature. The value above the emergency threshold value may indicate an emergency condition. The emergency biometric signature can include a kinesiological signature, such as where the emergency biometric signature includes a knee joint having a range of greater than 180°. Non-limiting examples of emergency conditions include broken bones, heart attacks, and blood loss.

Any of the medical system 100, the computing device 112, the clinic server 302, the biller server 406, the claim adjudication server 408, the FWA server 410, the payment server 412, the training server 506, the training engine 508, any other suitable computing device, or any combination thereof may be configured to use the device-based biometric signature and/or an emergency biometric signature to generate an emergency comparison. The emergency comparison can be derived from vital sign information, imagery, or any other suitable information. For example, a device-based biometric signature including a heart rate value of 0 bpm can be compared to an emergency biometric signature including an emergency range of heart rate values of 0-40 bpm. In this example, the emergency comparison indicates that the device-based biometric signature heart rate is within the emergency range. As another example, a device-based biometric signature including a user's face being a shade of purple can be compared to an emergency biometric signature including an emergency range of shades of the user's face. In this example, the emergency comparison indicates that the shade of the user's face is within the emergency range. As yet another example, a device-based biometric signature in which the range of motion of the user's joint has extended to 270° can be compared to an emergency biometric signature in which an emergency range of knee joint extension includes values greater than 180°. In this example, the emergency comparison indicates that the knee joint range is in the emergency range.

Any of the medical system 100, the computing device 112, the clinic server 302, the biller server 406, the claim adjudication server 408, the FWA server 410, the payment server 412, the training server 506, the training engine 508, any other suitable computing device, or any combination thereof may be configured to use the emergency comparison to generate an emergency indicator. The emergency indicator can include whether an emergency biometric signature matches a device-based biometric signature. Examples of the emergency indicators include flags and saved variables. For example, the emergency indicator can be generated when the comparison indicates a similarity or overlap between the device-based biometric signature and the emergency biometric signature. For example, the emergency indicator can be derived from the emergency comparison if the emergency comparison indicates that the knee joint range is in the emergency range.

Any of the medical system 100, the computing device 112, the clinic server 302, the biller server 406, the claim adjudication server 408, the FWA server 410, the payment server 412, the training server 506, the training engine 508, any other suitable computing device, or any combination thereof may be configured to transmit the emergency indicator. For example, any of the medical system 100, the computing device 112 of the medical system 100, the clinic server 302, the biller server 406, the claim adjudication server 408, the FWA server 410, the payment server 412, the training server 506, the training engine 508, any other suitable computing device, or any combination thereof may transmit the emergency indicator to the medical system 100, the computing device 112 of the medical system 100, the clinic server 302, the biller server 406, the claim adjudication server 408, the FWA server 410, the payment server 412, the training server 506, the training engine 508, an emergency services system or computer, any other suitable computing device, or any combination thereof. Further, the biometric information may also be transmitted to provide emergency or clinic services with information about the nature of the emergency. Further, the medical system 100, the computing device 112 of the medical system 100, the clinic server 302, the biller server 406, the claim adjudication server 408, the FWA server 410, the payment server 412, the training server 506, the training engine 508, an emergency services system or computer, any other suitable computing device, or any combination thereof can activate an output device 120, such as an alarm system. The alarm system can include a speaker, a siren, a system that contacts emergency services (e.g., to summon an ambulance), a flashing light, any other suitable alarm component, or any combination thereof.

FIG. 5 is not intended to be limiting; the medical claim processing system 500, the medical system 100, computing device 112, the clinic server 302, the clinic server 302, the computing device 304, the cloud-based learning system 504, and any sub-components thereof may include more or fewer components than those illustrated in FIG. 5.

Figure 6B:
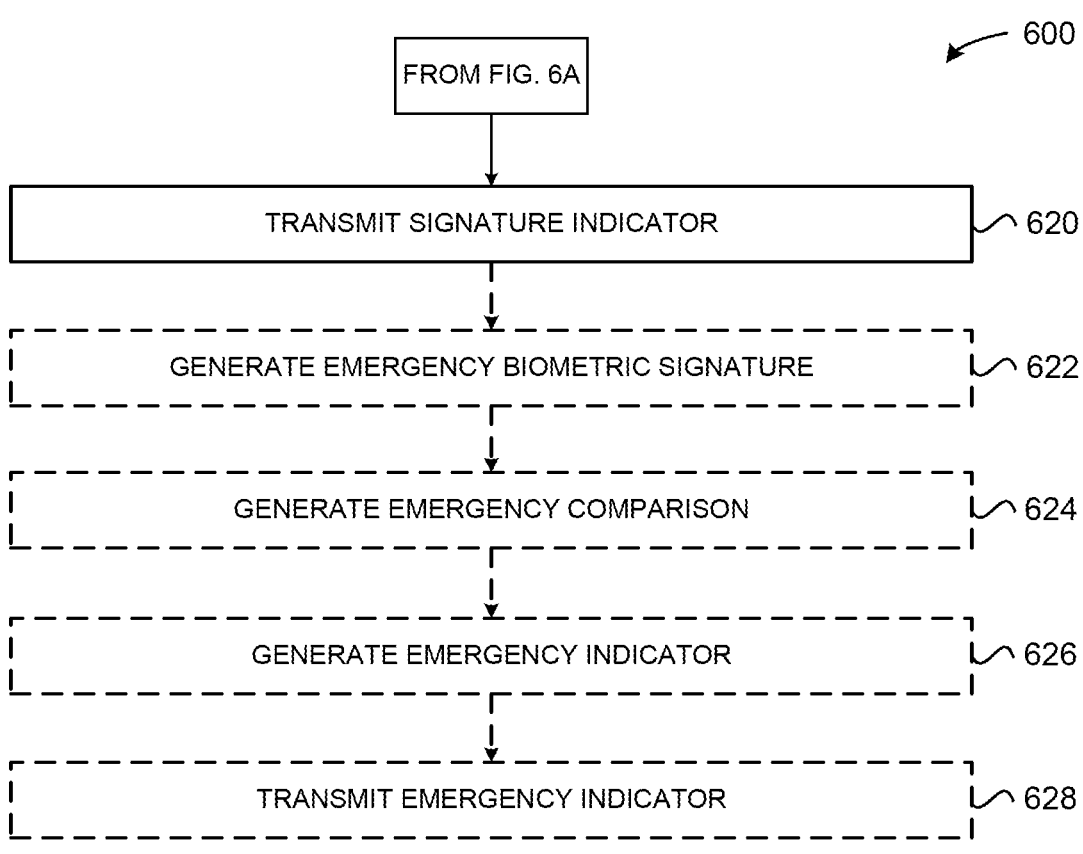

FIGS. 6A and 6B illustrate a computer-implemented method 600 for processing medical claims. The method 600 may be performed on the medical system 100, the computing device 112, the clinic server 302, the biller server 406, the claim adjudication server 408, the FWA server 410, the payment server 412, the training server 506, the training engine 508, any other suitable computing device, or any combination thereof. The method 600 may be implemented on a processor, such as the processor 306, configured to perform the steps of the method 600. The method 600 may be implemented on a system, such as the medical system 100 or the clinic server system 300, that includes a processor, such as the processor 306, and a memory device, such as the memory device 308. The method 600 may be implemented on the clinic server system 300. The method 600 may include operations that are implemented in instructions stored in a memory device, such as the memory device 308, and executed by a processor, such as the processor 306, of a computing device, such as the computing device 304. The steps of the method 600 may be stored in a non-transient computer-readable storage medium.

At step 602, the method 600 can include receiving device-generated information from a medical device, such as the medical device 102. For example, the clinic server 302 can receive (1) knee angle information from a goniometer attached to a knee of a user of the physical therapy cycle 200; and (2) pedal speed information and force information from the physical therapy cycle 200. After the clinic server 302 receives the device-generated information from the medical device 102, the clinic server 302 can proceed to step

604 or to step 610. Alternatively, the clinic server 302 can proceed to steps 604 and 610.

At step 604, the method 600 can include using the device-generated information to determine device-based medical coding information. For example, the clinic server 302 can use the pedal speed information and/or force information from the physical therapy cycle to determine that the user is undergoing a one-hour therapy session. The clinic server 302 can access the EMRs associated with the user to determine which information is relevant to the therapy session (e.g., that the user has a prior right knee injury). The clinic server 302 can determine medical coding information associated with one-hour therapy sessions for a right knee injury. After the clinic server 302 determines the device-based medical information, the clinic server 302 can proceed to step 606.

At step 606, the method 600 can include receiving reviewed medical coding information. For example, the clinic server 302 can receive information input by a doctor that the user has an injury to the user's left knee. After the clinic server 302 receives the reviewed medical coding information, the clinic server 302 can proceed to step 608.

At step 608, the method 600 can include receiving electronic medical records (EMRs) for a user of a medical device 102. For example, the clinic server 302 can receive information from the EMRs. The information can indicate that the user has an injury to the user's left knee. After the clinic server 302 receives the EMRs, the clinic server 302 can proceed to step 610.

At step 610, the method 600 can include generating a first biometric signature (i.e., a predicted biometric signature). The clinic server 302 can generate the first biometric signature. The first biometric signature may be a kinesiological signature of a user. For example, the clinic server 302 can use the injury and the past performance of the user to generate a first biometric signature, which may include a first kinesiological signature (i.e., an emergency kinesiological signature) having a predicted left knee joint range of motion between approximately 130°-140° and a predicted right knee joint range of motion between approximately 165-170°. After the clinic server 302 generates the first biometric signature, the clinic server 302 can proceed to step 612.

At step 612, the method 600 can include generating, using the device-generated information, a second biometric signature (i.e., a device-based biometric signature). The second biometric signature may be a kinesiological signature. For example, the clinic server 302 can generate, using the measurements from the goniometer, a second biometric signature including a second kinesiological signature (i.e., a device-based kinesiological signature) having a left knee joint range of motion of approximately 170° and a right knee joint range of motion of approximately 135°. After the clinic server 302 generates the second biometric signature, the clinic server 302 can proceed to step 614.

At step 614, the method 600 can include comparing the first and second biometric signatures. For example, the clinic server 302 can compare the predicted left knee joint range of motion (i.e., the first biometric signature having a predicted a range of motion of approximately) 130°-140° and the measured a left knee joint range of motion (i.e., the second biometric signature with a measured range of motion of approximately 170°). After the clinic server 302 generates compares the first and second biometric signatures, the clinic server 302 can proceed to step 616.

At step 616, the method 600 can include generating, using the first biometric signature and the second biometric signature, a signature comparison. For example, the clinic server 302 can generate a signature comparison showing that the user's left knee joint range of motion is outside of the expected range of motion for the user's left knee joint (e.g., approximately 30° above the expected maximum range of motion). The clinic server 302 can generate one or more signature comparisons. For example, the clinic server 302 can generate a second signal comparison that the user's right knee joint range of motion is outside of the expected range of motion for the user's right knee joint (e.g., approximately 30° below the expected minimum range of motion). After the clinic server 302 generates the signature comparison, the clinic server 302 can proceed to step 618.

At step 618, the method 600 can include generating, using the signature comparison, a signature indicator (e.g., a variable or flag that indicates whether the differences between the first and second biometric signatures exceed a FWA threshold value). The signature indicator can include flagging if the differences are determined to be the result of an incorrect user. For example, the clinic server 302 can use the left knee joint range of motion being outside of an expected range of motion threshold to generate a signature indicator flagging that the user may be an incorrect user, that there may be an error in the medical records, that the goniometer measurements may have been incorrect (e.g., another user's medical records) resulting from an operator error, or that any other suitable error has occurred. After the clinic server 302 generates the signature indicator, the clinic server 302 can proceed to step 620.

At step 620, the method 600 can include transmitting the signature indicator. For example, the clinic server 302 may transmit the signature indicator to the biller server 406. After the clinic server 302 transmits the signature indicator, the clinic server 302 can end the method or proceed to step 622.

At step 622, the method 600 can include generating an emergency biometric signature including information indicative of an emergency event (e.g., a heart attack, broken bone, blood loss, etc.). For example, the clinic server 302 can generate an emergency biometric signature having a knee joint range of motion in excess of 185°. After the clinic server 302 generates the emergency biometric signature, the clinic server 302 can proceed to step 624.

At step 624, the method 600 can include using the second biometric signature and the emergency biometric signature to generate an emergency comparison. For example, if the emergency biometric signature is generated when a knee joint range of motion of a user operating the physical therapy cycle 200 is greater than an emergency threshold of 185° and the second biometric signature determines that a knee joint range of motion of a user operating the physical therapy cycle 200 is approximately 270°, the user has exceeded the emergency threshold and the clinic server 302 can generate the emergency comparison. After the clinic server 302 generates the emergency comparison, the clinic server 302 can proceed to step 626.

At step 626, the method 600 can include, using the emergency comparison to generate an emergency indicator. For example, using the second biometric signature having a knee joint range of motion exceeding the emergency threshold of the emergency biometric signature (e.g., the user's range of motion is 85° greater than the emergency biometric signature), the clinic server 302 can determine that there is an emergency condition. After the clinic server 302 generates the emergency indicator, the clinic server 302 can proceed to step 628.

At step 628, the method 600 can include transmitting the emergency indicator. For example, in response to the generation of the emergency indicator, the clinic server 302 can transmit the emergency indicator to an on-site registered nurse. The emergency indicator may include information, device-generated information, EMRs, the emergency comparison, any other suitable information, or any combination thereof.

FIGS. 6A and 6B are not intended to be limiting; the method 600 can include more or fewer steps and/or processes than those illustrated in FIG. 6. Further, the order of the steps of the method 600 is not intended to be limiting; the steps can be arranged in any suitable order. Any or all of the steps of method 600 may be implemented during a telemedicine session or at any other desired time.

Figure 10:
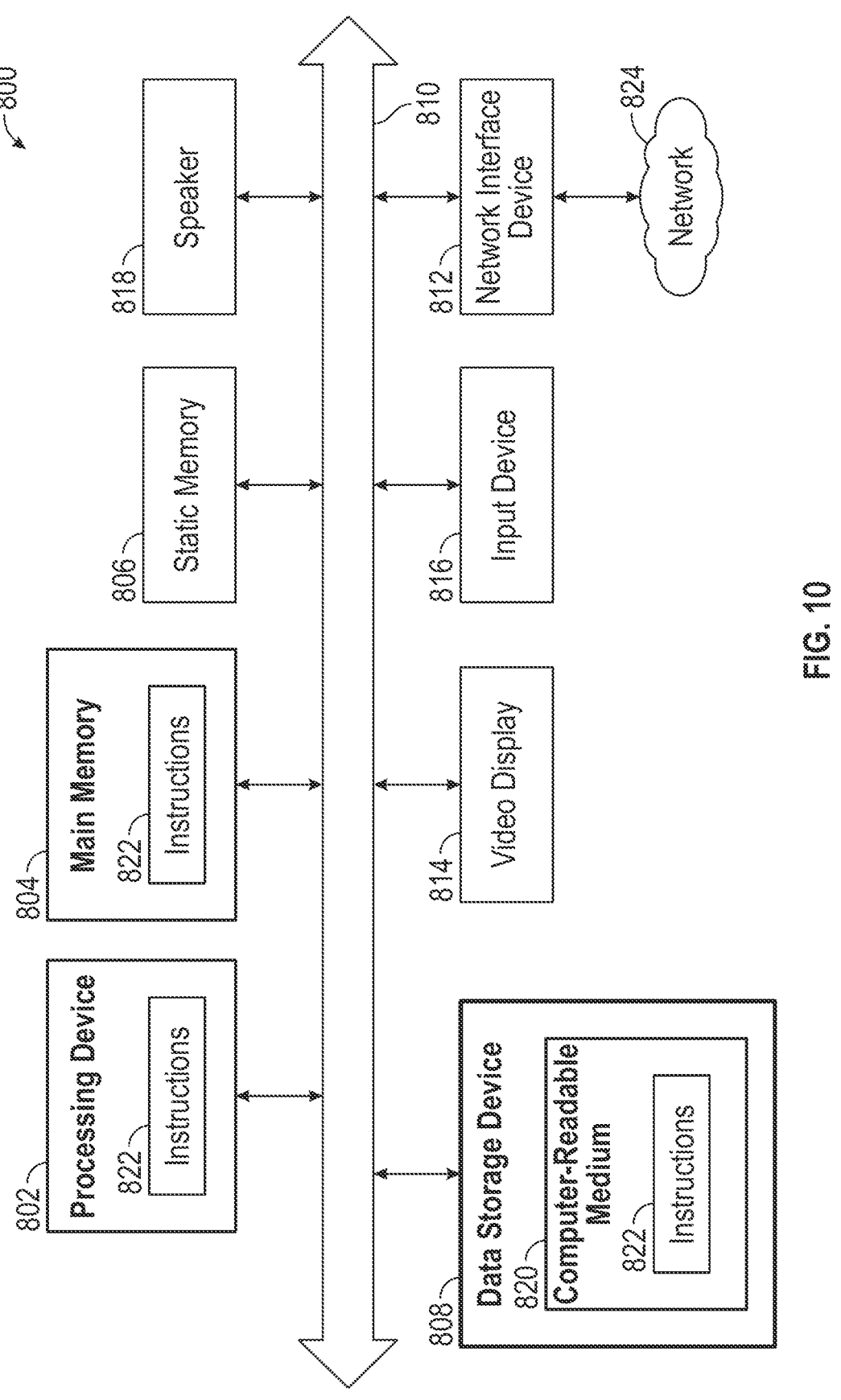
FIG. 10 generally illustrates an example computer system according to certain aspects of this disclosure.

FIG. 10 shows an example computer system 800 which can perform any one or more of the methods described herein, in accordance with one or more aspects of the present disclosure. In one example, computer system 800 may include a computing device and correspond to an assistance interface, a reporting interface, a supervisory interface, a clinician interface, a server (including an AI engine), a patient interface, an ambulatory sensor, a goniometer, a treatment device 10, a medical device 102, a pressure sensor, or any suitable component. The computer system 800 may be capable of executing instructions implementing the one or more machine learning models of the artificial intelligence engine. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 800 includes a processing device 802, a main memory 804 (e.g., read-only memory (ROM), flash memory, solid state drives (SSDs), dynamic random access memory (DRAM) such as synchronous DRAM (SDRAM)), a static memory 806 (e.g., flash memory, solid state drives (SSDs), static random access memory (SRAM)), and a data storage device 808, which communicate with each other via a bus 810.

Processing device 802 represents one or more general-purpose processing devices such as a microprocessor, central processing unit, or the like. More particularly, the processing device 802 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 802 may also be one or more special-purpose processing devices such as an application specific integrated circuit (ASIC), a system on a chip, a field programmable gate array (FPGA), a digital signal processor (DSP), network processor, or the like. The processing device 802 is configured to execute instructions for performing any of the operations and steps discussed herein.

The computer system 800 may further include a network interface device 812. The computer system 800 also may include a video display 814 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 816 (e.g., a keyboard and/or a mouse or a gaming-like control), and one or more speakers 818 (e.g., a speaker). In one illustrative example, the video display 814 and the input device(s) 816 may be combined into a single component or device (e.g., an LCD touch screen).

The data storage device 816 may include a computer-readable medium 820 on which the instructions 822 embodying any one or more of the methods, operations, or functions described herein is stored. The instructions 822 may also reside, completely or at least partially, within the main memory 804 and/or within the processing device 802 during execution thereof by the computer system 800. As such, the main memory 804 and the processing device 802 also constitute computer-readable media. The instructions 822 may further be transmitted or received over a network via the network interface device 812.

While the computer-readable storage medium 820 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

FIG. 10 is not intended to be limiting; the system 800 may include more or fewer components than those illustrated in FIG. 10.

The term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying a set of instructions for execution by the machine and causing the machine to perform any one or more of the methodologies of the present disclosure. The term "computer-readable storage medium" shall accordingly be taken to include, but not be limited to, solid-state memories, optical media, and magnetic media.

Any of the systems and methods described in this disclosure may be used in connection with rehabilitation. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. The patient may prepare an area of his or her body for the surgical procedure by performing the one or more sets of exercises, thereby strengthening muscle groups, improving existing and/or establishing new muscle memory, enhancing mobility, improving blood flow, and/or the like.

In some embodiments, the systems and methods described herein may use artificial intelligence and/or machine learning to generate a prehabilitation treatment plan for a user. Additionally, or alternatively, the systems and methods described herein may use artificial intelligence and/or machine learning to recommend an optimal exercise machine configuration for a user. For example, a data model may be trained on historical data such that the data model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the patient, a recommended health professional specialist to contact, and/or the like.

Consistent with the above disclosure, the examples of systems and method enumerated in the following clauses are specifically contemplated and are intended as a non-limiting set of examples.

Clause 1. A computer-implemented system for processing medical claims, comprising:
a medical device configured to be manipulated by a user while the user performs a treatment plan;
a patient interface associated with the medical device, the patient interface comprising an output configured to present telemedicine information associated with a telemedicine session; and
a processor configured to:
during the telemedicine session, receive device-generated information from the medical device;
generate a first biometric signature;
using the device-generated information, generate a second biometric signature;
using the first and second biometric signatures, generate a signature comparison;
using the signature comparison, generate a signature indicator; and
transmit the signature indicator.
Clause 2. The computer-implemented system of any clause herein, wherein:
the device-generated information is generated by the medical device;

using the device-generated information, the processor is further configured to determine device-based medical coding information; and
generating the second biometric signature uses the device-based medical coding information.
Clause 3. The computer-implemented system of any clause herein, wherein the processor is further configured to receive reviewed medical coding information; and
wherein generating the first biometric signature uses the reviewed medical coding information.
Clause 4. The computer-implemented system of any clause herein, wherein the processor is further configured to receive electronic medical records pertaining to the user of the medical device; and
wherein generating the first biometric signature uses the electronic medical records.
Clause 5. The computer-implemented system of any clause herein, wherein the processor is further configured to:
using the second biometric signature and an emergency biometric signature, generate an emergency comparison;
using the emergency comparison, generate an emergency indicator; and
transmit the emergency indicator.
Clause 6. A system for processing medical claims, comprising:
a processor configured to:
receive device-generated information from a medical device;
generate a first biometric signature;
using the device-generated information, generate a second biometric signature;
using the first biometric signature and the second biometric signature, compare the signatures;
using the first and second biometric signatures, generate a signature comparison;
using the signature comparison, generate a signature indicator; and
transmit the signature indicator.
Clause 7. The system of any clause herein, wherein the device-generated information is generated by the medical device.
Clause 8. The system of any clause herein, wherein, using the device-generated information, the processor is further configured to determine device-based medical coding information; and
wherein generating the second biometric signature uses the device-based medical coding information.
Clause 9. The system of any clause herein, wherein the processor is further configured to receive reviewed medical coding information; and
wherein generating the first biometric signature uses the reviewed medical coding information.
Clause 10. The system of any clause herein, wherein the processor is further configured to receive electronic medical records pertaining to a user of the medical device; and
wherein generating the first biometric signature uses the electronic medical records.
Clause 11. The system of any clause herein, wherein the processor is further configured to:
using the second biometric signature and an emergency biometric signature, generate an emergency comparison;
using the emergency comparison, generate an emergency indicator; and
transmit the emergency indicator.

Clause 12. The system of any clause herein, wherein the processor is further configured to generate the emergency biometric signature.

Clause 13. The system of any clause herein, wherein the device-generated information includes at least one of vital sign information, images, and medical device use information.

Clause 14. The system of any clause herein, wherein the device-generated information includes performance information; and wherein generating the second biometric signature uses the performance information.

Clause 15. The system of any clause herein, wherein generating the first biometric signature uses historical performance information.

Clause 16. The system of any clause herein, wherein the first biometric signature includes a first kinesiological signature; and wherein the second biometric signature includes a second kinesiological signature.

Clause 17. The system of any clause herein, further comprising a memory device operatively coupled to the processor, wherein the memory device stores instructions, and wherein the processor is configured to execute the instructions.

Clause 18. A method for processing medical claims, comprising:

receiving device-generated information from a medical device;

generating a first biometric signature;

using the device-generated information, generating a second biometric signature;

using the first biometric signature and the second biometric signature, generating a signature comparison;

using the signature comparison, generating a signature indicator; and transmitting the signature indicator.

Clause 19. The method of any clause herein, wherein the device-generated information is generated by the medical device.

Clause 20. The method of any clause herein, further comprising using the device-generated information to determine device-based medical coding information;

wherein generating the second biometric signature uses the device-based medical coding information.

Clause 21. The method of any clause herein, further comprising receiving reviewed medical coding information; wherein generating the first biometric signature uses the reviewed medical coding information.

Clause 22. The method of any clause herein, further comprising receiving electronic medical records pertaining to a user of the medical device; wherein generating the first biometric signature uses the electronic medical records.

Clause 23. The method of any clause herein, further comprising:

using the second biometric signature and an emergency biometric signature to generate an emergency comparison;

using the emergency comparison to generate an emergency indicator; and transmitting the emergency indicator.

Clause 24. The method of any clause herein, further comprising generating the emergency biometric signature.

Clause 25. The method of any clause herein, wherein the device-generated information includes at least one of vital sign information, images, and medical device use information.

Clause 26. The method of any clause herein, wherein the device-generated information includes performance information; and wherein generating the second biometric signature uses the performance information.

Clause 27. The method of any clause herein, wherein generating the first biometric signature uses historical performance information.

Clause 28. The method of any clause herein, wherein the first biometric signature includes a first kinesiological signature; and wherein the second biometric signature includes a second kinesiological signature.

Clause 29. A tangible, non-transitory computer-readable storage medium storing instructions that, when executed, cause a processor to:

receive device-generated information from a medical device;

generate a first biometric signature;

using the device-generated information, generate a second biometric signature;

using the first biometric signature and the second biometric signature, generate a signature comparison;

using the signature comparison, generate a signature indicator; and transmit the signature indicator.

Clause 30. The tangible, non-transitory computer-readable storage medium of any clause herein, wherein the device-generated information is generated by the medical device.

Clause 31. The tangible, non-transitory computer-readable storage medium of any clause herein, wherein using the device-generated information, the instructions further cause the processor to determine device-based medical coding information; and wherein generating the second biometric signature uses the device-based medical coding information.

Clause 32. The tangible, non-transitory computer-readable storage medium of any clause herein, wherein the instructions further cause the processor to receive electronic medical records pertaining to a user of the medical device; and wherein generating the first biometric signature uses the electronic medical records.

Clause 33. The tangible, non-transitory computer-readable storage medium of any clause herein, wherein the instructions further cause the processor to:

using the second biometric signature and an emergency biometric signature, generate an emergency comparison;

using the emergency comparison, generate an emergency indicator; and transmit the emergency indicator.

Clause 34. The tangible, non-transitory computer-readable storage medium of any clause herein, wherein the instructions further cause the processor to generate the emergency biometric signature.

Clause 35. The tangible, non-transitory computer-readable storage medium of any clause herein, wherein the device-generated information includes at least one of vital sign information, images, and medical device use information.

Clause 36. The tangible, non-transitory computer-readable storage medium of any clause herein, wherein the device-generated information includes performance information; and wherein generating the second biometric signature uses the performance information.

Clause 37. The tangible, non-transitory computer-readable storage medium of any clause herein, wherein the device-generated information includes performance information; and wherein generating the second biometric signature uses the performance information.

Clause 38. The tangible, non-transitory computer-readable storage medium of any clause herein, wherein generating the first biometric signature uses historical performance information.

Clause 39. The tangible, non-transitory computer-readable storage medium of any clause herein, wherein the first biometric signature includes a first kinesiological signature; and wherein the second biometric signature includes a second kinesiological signature.

No part of the description in this application should be read as implying that any particular element, step, or function is an essential element that must be included in the claim scope. The scope of patented subject matter is defined only by the claims. Moreover, none of the claims is intended to invoke 35 U.S.C. § 112(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A computer-implemented system, comprising:

an exercise device configured to be used by a user to perform a treatment plan and to generate device-generated information while the user performs the treatment plan using the exercise device, wherein the device-generated information includes performance information indicative of human body movements of the user that are obtained while the user uses the exercise device;

a user interface associated with the exercise device, the user interface comprising an output configured to present exercise information associated with an exercise session; and a processor configured to:

generate a first biometric signature derived from a biological characteristic of the user determined prior to the exercise session;

generate a second biometric signature derived from a kinesiological movement that is performed by the user while the user performs the treatment plan using the exercise device, wherein the second biometric signature is determined by a sensor included with the exercise device;

using the first biometric signature and historical medical information of the user, generate a predicted biometric signature identifying a range of motion of a joint or muscle of the user;

generate a signature comparison by comparing the second biometric signature and the predicted biometric signature;

in response to the signature comparison exceeding a fraud, waste, or abuse (FWA) threshold value, generate a signature indicator that indicates an error or an inconsistency between the biological characteristic of the user determined prior to the exercise session and the kinesiological movement of the user while the user performs the treatment plan using the exercise device;

transmit, to a claim adjudication server, the signature indicator; and based on the signature indicator, determine, by the claim adjudication server, to not pay a claim associated with the user performing the treatment plan by using the exercise device.

2. The computer-implemented system of claim 1, wherein:

the device-generated information is generated by the exercise device; and the processor is further configured to:

determine, using the device-generated information, device-based coding information; and generate, using the device-based coding information, the second biometric signature.

3. The computer-implemented system of claim 1, wherein the processor is further configured to receive reviewed coding information; and wherein generating the first biometric signature uses the reviewed coding information.

4. The computer-implemented system of claim 3, wherein the reviewed coding information comprises at least one of medical coding information and non-medical coding information.

5. The computer-implemented system of claim 1, wherein the processor is further configured to receive electronic records pertaining to the user of the exercise device; and wherein generating the first biometric signature uses the electronic records.

6. The computer-implemented system of claim 1, wherein the processor is further configured to:

using the second biometric signature and an emergency biometric signature, generate an emergency comparison;

using the emergency comparison, generate an emergency indicator; and transmit the emergency indicator.

7. The computer-implemented system of claim 1, wherein the exercise device comprises one of an electromechanical device, a treadmill, an electromechanical spin-wheel, an electromechanical bicycle, an exercise and rehabilitation device, a physical therapy device, or some combination thereof.

8. The computer-implemented system of claim 1, wherein the processor is further configured to:

generate a third biometric signature derived from a second kinesiological movement that is performed while the user performs the treatment plan using the exercise device, wherein the second kinesiological movement involves the range of motion of the joint or the muscle of the user;

compare the third biometric signature to an emergency biometric signature; and in response to the third biometric signature exceeding a threshold value that distinguishes the third biometric signature from the emergency biometric signature, transmit an emergency indicator that comprises the third biometric signature.

9. A method, comprising, using a processor:

receiving device-generated information from an exercise device during an exercise session in which a user uses the exercise device to perform a treatment plan, wherein the device-generated information includes performance information indicative of human body movements of the user that are obtained while the user uses the exercise device;

generating a first biometric signature derived from a biological characteristic of the user determined prior to the exercise session;

generating a second biometric signature derived from a kinesiological movement that is performed by the user while the user performs the treatment plan using the exercise device, wherein the second biometric signature is determined by a sensor included with the exercise device;

using the first biometric signature and historical medical information of the user, generating a predicted biometric signature identifying a range of motion of a joint or muscle of the user;

generating a signature comparison by comparing the second biometric signature and the predicted biometric signature;

in response to the signature comparison exceeding a fraud, waste, or abuse (FWA) threshold value, generating a signature indicator that indicates an error or an inconsistency between the biological characteristic of the user determined prior to the exercise session and the kinesiological movement of the user while the user performs the treatment plan using the exercise device;

transmitting, to a claim adjudication server, the signature indicator; and based on the signature indicator, determining, by the claim adjudication server, to not pay a claim associated with the user performing the treatment plan by using the exercise device.

10. The method of claim 9, wherein the device-generated information is generated by the exercise device.

11. The method of claim 9, further comprising using the device-generated information to determine device-based coding information, wherein generating the second biometric signature uses the device-based coding information.

12. The method of claim 9, further comprising receiving reviewed coding information, wherein generating the first biometric signature uses the reviewed coding information.

13. The method of claim 9, further comprising receiving electronic records pertaining to the user of the exercise device, wherein generating the first biometric signature uses the electronic records.

14. The method of claim 9, further comprising:

generating, using the second biometric signature and an emergency biometric signature, an emergency comparison;

generating, using the emergency comparison, an emergency indicator; and transmitting the emergency indicator.

15. The method of claim 14, further comprising generating the emergency biometric signature.

16. The method of claim 9, wherein the device-generated information includes at least one of vital sign information, images, exercise device use information, and performance information.

17. The method of claim 9, wherein the exercise device comprises one of an electromechanical device, a treadmill, an electromechanical spin-wheel, an electromechanical bicycle, an exercise and rehabilitation device, a physical therapy device, or some combination thereof.

* * * * *